(12) United States Patent
Basu et al.

(10) Patent No.: US 11,407,758 B2
(45) Date of Patent: Aug. 9, 2022

(54) TRICYCLIC COMPOUNDS, COMPOSITIONS AND MEDICINAL APPLICATIONS THEREOF

(71) Applicant: IMPETIS BIOSCIENCES LTD., Mumbia (IN)

(72) Inventors: Sujay Basu, Mumbia (IN); Sachin Thorat, Mumbia (IN); Yogesh Shejul, Mumbia (IN); Anil Panmand, Mumbia (IN); Meena Patel, Mumbia (IN); Goraksha Khose, Mumbia (IN); Rajesh Bonagiri, Mumbia (IN); Dinesh Barawkar, Mumbia (IN); Bheemashankar Kulkarni, Mumbia (IN); Kasim Mookhtiar, Mumbia (IN)

(73) Assignee: IMPETIS BIOSCIENCES LTD., Mumbia (IN)

( * ) Notice: Subject to any disclaimer, the term of this patent is extended or adjusted under 35 U.S.C. 154(b) by 0 days.

(21) Appl. No.: 16/959,543

(22) PCT Filed: Jan. 4, 2019

(86) PCT No.: PCT/IN2019/050009
§ 371 (c)(1),
(2) Date: Jul. 1, 2020

(87) PCT Pub. No.: WO2019/135259
PCT Pub. Date: Jul. 11, 2019

(65) Prior Publication Data
US 2021/0070764 A1 Mar. 11, 2021

(30) Foreign Application Priority Data

Jan. 4, 2018 (IN) .............................. 201821000484

(51) Int. Cl.
*C07D 487/14* (2006.01)
(52) U.S. Cl.
CPC .................................. *C07D 487/14* (2013.01)
(58) Field of Classification Search
CPC .................................................. C07D 487/14
USPC ....................................................... 514/267
See application file for complete search history.

(56) References Cited

U.S. PATENT DOCUMENTS

| 2008/0194593 A1 | 8/2008 | Kalla et al. |
| 2013/0324724 A1 | 12/2013 | Diep et al. |

FOREIGN PATENT DOCUMENTS

| EP | 0417790 A2 | 3/1991 |
| EP | 0884318 A1 | 12/1998 |
| EP | 1069126 A1 | 1/2001 |
| EP | 1902716 A1 | 3/2008 |
| WO | WO 2001/007441 A1 | 2/2001 |
| WO | WO 2001/058241 A2 | 8/2001 |
| WO | WO 2001/092264 A1 | 12/2001 |
| WO | WO 2002/044182 A1 | 6/2002 |
| WO | WO 2002/055083 A1 | 7/2002 |
| WO | WO 2003/022284 A1 | 3/2003 |
| WO | WO 2005/044245 A1 | 5/2005 |
| WO | WO 2006/009698 A2 | 1/2006 |

(Continued)

OTHER PUBLICATIONS

Toro et al.; "Development and validation of a capillary electrophoresis method with ultraviolet detection for the determination of the related substances in a pharmaceutical compound"; Journal of Chromatography A; vol. 1043; Jul. 2004; p. 303-315.

(Continued)

*Primary Examiner* — Taofiq A Solola
(74) *Attorney, Agent, or Firm* — BakerHostetler

(57) ABSTRACT

The present disclosure relates to a series of tricyclic compounds, their tautomers, polymorphs, stereoisomers, prodrugs, solvates, pharmaceutically acceptable salts, pharmaceutical compositions containing them and methods of treating conditions and diseases that are mediated by adenosine receptor (AR) activity. The disclosure also relates to process of preparation of these tricyclic compounds of Formula I. These compounds are useful in the treatment, prevention or suppression of diseases and disorders that may be susceptible to improvement by antagonism of the adenosine receptor. The disclosure also relates to the process of preparation of the tricyclic compounds, and to pharmaceutical compositions containing them. Formula (I) wherein D represents a tricyclic ring system selected from: Formula (II) or Formula (III).

D—A—B—Z  (I)

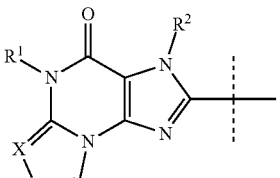

(II)

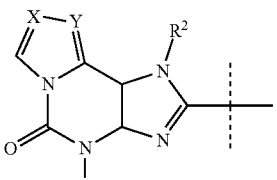

(III)

12 Claims, No Drawings

(56) References Cited

FOREIGN PATENT DOCUMENTS

| WO | WO 2006/132275 A1 | 12/2006 |
|---|---|---|
| WO | WO 2009/157938 A1 | 12/2009 |

OTHER PUBLICATIONS

International Patent Application No. PCT/IN2019/050009; Int'l Written Opinion and Search Report; dated Feb. 27, 2019; 13 pages.

Richardson et al.; "Adenosine A2A receptor antagonists as new agents for the treatment of Parkinson's disease"; Trends in Pharmacological Sciences; vol. 18; Jul. 1997; p. 338-344.

Gao et al.; "CGS 15943, An adenosine A2 receptor antagonist, reduces cerebral ischemic injury in the mongolian gerbil"; Life Sciences; vol. 55; 1994; p. 61-65.

Chan et al.; "Adenosine A2A Receptors in Diffuse Dermal Fibrosis"; Arthritis & Rheumatism; vol. 54; Aug. 2006; p. 2632-2642.

Xu et al.; "Therapeutic potential of adenosine A2A receptor antagonists in Parkinson's disease"; Pharmacology & Therapeutics; vol. 105; Mar. 2005; p. 267-310.

Fuxe et al.; "Adenosine A2A and Dopamine D2 Heteromeric Receptor Complexes and Their Function"; Journal of Molecular Neuroscience; vol. 26; 2005; p. 209-219.

Hauben et al.; "Therapeutic vaccination for spinal cord injury: helping the body to cure itself"; Trends in Pharmacological Sciences; vol. 24; Jan. 2003; p. 7-12.

Feoktistov et al.; "Adenosine A2B Receptors"; Pharmacological Reviews; vol. 49; Dec. 1997; p. 381-402.

Borea et al.; "The A3 Adenosine Receptor: History and Perspectives"; Pharmacological Reviews; vol. 67; Jan. 2015; p. 74-102.

Fozard Jr.; "Adenosine receptor ligands: potential as therapeutic agents in asthma and COPP."; Pulmonary Pharmacology & Therapeutics; vol. 12; 1999; p. 111-114.

Polosa et al.; "Adenosine Receptors as Promising Therapeutic Targets for Drug Development in Chronic Airway Inflammation"; Current Drug Targets; vol. 7; 2006; p. 699-706.

Rothen-Rutishauser et al.; "A Three-Dimensional Cellular Model of the Human Respiratory Tract to Study the Interaction with Particles"; American Journal of Respiratory Cell and Molecular Biology; vol. 32; 2005; p. 281-289.

Feoktistov et al.; "Differential Expression of Adenosine Receptors in Human Endothelial Cells Role of A2B Receptors in Angiogenic Factor Regulation"; Circulation Research; vol. 90; Mar. 2002; p. 531-538.

Chen et al.; "Functional effects of enhancing or silencing adenosine A2b receptors in cardiac fibroblasts"; Am. J. Physiol. Heart Circ. Physiol.; vol. 287; Jul. 2004; p. H2478-H2486.

Rollins et al.; "A2B Adenosine Receptors Regulate the Mucus Clearance Component of the Lung's Innate Defense System"; American Journal of Respiratory Cell and Molecular Biology; vol. 39; 2008; p. 190-197.

Abo-Salem et al.; "Antinociceptive Effects of Novel A2B Adenosine Receptor Antagonists"; The Journal of Pharmacology and Experimental Therapeutics; vol. 308; 2004; p. 358-366.

Rusing et al.; "The impact of adenosine and A2B receptors on glucose homoeostasis"; Journal of Pharmacy and Pharmacology; vol. 58; Dec. 2006; p. 1639-1645.

Muller; "General Synthesis and Properties of 1-Monosubstituted Xanthines"; Synthesis; Jan. 1993; p. 125-128.

Beavis et al.; "Blockade of A2A receptors potently suppresses the metastasis of CD73+ tumors"; PNAS; vol. 110 No. 36; Sep. 2013; p. 14711-14716.

TRICYCLIC COMPOUNDS, COMPOSITIONS AND MEDICINAL APPLICATIONS THEREOF

REFERENCE TO RELATED APPLICATIONS

This application is a National Stage of International Application No. PCT/IN2019/050009, filed on Jan. 4, 2019, which claims priority to Indian patent application no. 201821000484, filed on Jan. 4, 2018, the disclosures of which are incorporated by reference in their entirety.

FIELD OF THE INVENTION

The present disclosure relates a series of tricyclic compounds, their tautomers, polymorphs, stereoisomers, prodrugs, solvates, pharmaceutically acceptable salts, pharmaceutical compositions containing them and methods of treating conditions and diseases that are mediated by adenosine receptor (AR) activity. These compounds are useful in the treatment, prevention or suppression of diseases and disorders that may be susceptible to improvement by antagonism of the adenosine receptor. The disclosure also relates to the process of preparation of the tricyclic compounds, and to pharmaceutical compositions containing them.

BACKGROUND OF INVENTION

Adenosine is an endogenous modulator of a wide range of physiological functions and is implicated in several pathologies. Recent advances in molecular biology coupled with several pharmacological studies have lead to identification of at least four subtypes of adenosine receptors, $A_1$, $A_{2A}$, $A_{2B}$ and $A_3$. The $A_1$ and $A_3$ receptors down-regulate cellular cAMP levels through their coupling to G protein, which inhibit adenylate cyclase. In contrast, $A_{2A}$ and $A_{2B}$ receptors couple to G protein that activate adenylate cyclase and increase intracellular levels of cAMP.

Advances in understanding the role of adenosine and its receptors in physiology and pathophysiology as well as new developments in medicinal chemistry of these receptors have identified potential therapeutic areas for drug development. With the combination of pharmacological data using selective ligands and genetically modified mice, important progress has been made towards understanding of the role of adenosine receptors (Ars) in a variety of diseases, such as inflammatory conditions, sepsis, heart attack, ischemia-reperfusion injury, vascular injury, spinal cord injury, chronic obstructive pulmonary disease (COPD), asthma, diabetes, obesity, inflammatory bowel disease, retinopathy, and Parkinson's Disease (PD).

In the central nervous system, $A_{2A}$ antagonists can have antidepressant properties and stimulate cognitive functions. Epidemiological evidence shows a protective role for caffeine in Parkinson's disease. Moreover, $A_{2A}$ receptor density is found to be very high in the basal ganglia which regulate motor control function. Hence, selective $A_{2A}$ antagonists can improve motor impairment due to neurodegenerative diseases, such as, Parkinson's disease (Trends Pharmacol. Sci. 1997, 18, 338-344), senile dementia as in Alzheimer's disease, psychoses, stroke and be potentially effective in the treatment of cerebral ischaemia (Life Sci. 1994, 55, 61-65). $A_{2a}$ antagonists may also be employed for the treatment or management of attention related disorders such as attention deficit disorder and attention deficit hyperactivity disorder, extra pyramidal syndrome, e.g., dystonia, akathisia, pseudoparkinsonism and tardive dyskinesia, and disorders of abnormal movement such as restless leg syndrome and periodic limb movement in sleep. Several of these indications have been disclosed in patent applications (eg. WO 02/055083, WO 05/044245 and WO 06/132275). Adenosine $A_{2A}$ antagonists could also be useful in the treatment of amyotrophic lateral sclerosis, cirrhosis, and fibrosis and fatty liver (US2007037033, WO 01/058241). $A_{2A}$ receptor antagonists are also useful for the mitigation of addictive behavior (WO 06/009698) and for the treatment and prevention of dermal fibrosis in diseases such as scleroderma (Arthritis & Rheumatism, 2006; 54(8), 2632-2642).

Parkinson's disease (PD) is a progressive, incurable disorder with no definite preventive treatment, although drugs are available to alleviate the symptoms and/or slow down the progress of the disease. Among the various strategies, $A_{2A}$ AR blockers are considered a potential approach to treatment of the disease. Within the brain $A_{2A}$ ARs are richly expressed in the striatum, nucleus accumbens, and olfactory tubercle. Co-expression of $A_{2A}$ with D2 dopamine receptors has been reported in the GABAergic striatopallidal neurons where adenosine and dopamine agonists exert antagonistic effects in the regulation of locomotor activity. Activation of $A_{2A}$ ARs in striatopallidal neurons decreases the affinity of D2 receptors for dopamine, antagonizing the effects of D2 receptors. The negative interaction between $A_{2A}$ and D2 receptors is at the basis of the use of $A_{2A}$ antagonists as a novel therapeutic approach in the treatment of PD (Pharmacol. Ther. 2005, 105, 267). The recent discovery that the $A_{2A}$ can form functional heteromeric receptor complexes with other G protein-coupled receptors such as D2 receptors and the mGlu5 receptors has also suggested new opportunities for the potential of $A_{2A}$ antagonists in PD (J. Mol. Neurosci. 2005, 26, 209).

Adenosine signaling is known to serve apoptotic, angiogenic and proinflammatory functions and might be relevant to the pathogenesis of asthma and chronic obstructive pulmonary disease (Trends in Pharmacol. Sci., 2003, 24, 8). Extracellular adenosine acts as a local modulator with a generally cytoprotective function in the body. Its effects on tissue protection and repair fall into four categories: increasing the ratio of oxygen supply to demand; protecting against ischaemic damage by cell conditioning; triggering anti-inflammatory responses; and the promotion of angiogenesis.

The $A_{2B}$ adenosine receptor subtype (I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation.

$A_{2B}$ receptors have been implicated in mast cell activation and asthma, control of vascular tone, cardiac myocyte contractility, cell growth and gene expression, vasodilation, regulation of cell growth, intestinal function, and modulation of neurosecretion (Pharmacol. Rev., 2003, 49, 4).

$A_{2B}$ receptors modulate mast cell function. Adenosine activates adenylate cyclase and protein kinase C and potentiates stimulated mediator release in mouse bone marrow derived mast cells. Activation of $A_{2B}$ receptors in HMC-1 augments IL-8 release and potentiates PMA-induced secretion of IL-8. Thus, adenosine would contribute to the asthmatic response by acting on the mast cell to enhance the release of proinflammatory mediators. (Pulmonary Pharmacology & Therapeutics 1999, 12, 111-114). In COPD, transformation of pulmonary fibroblasts into myofibroblasts is considered a major mechanism. Activation of the $A_{2B}$ AR is involved in this process. Selective $A_{2B}$ antagonists are expected to have beneficial effect on pulmonary fibrosis (Curr. Drug Targets, 2006, 7, 699-706; Am. J. Resper. Cell. Mol. Biol., 2005, 32, 228). $A_{2B}$ antagonists can be used as wound healing agents. Activation of the $A_{2B}$ AR promotes angiogenesis by increasing the release of angiogenic factors and $A_{2B}$ antagonists are useful to block angiogenesis (Circ. Res., 2002, 90, 531-538). $A_{2B}$ AR may be involved in the inhibition cardiac fibroblast (CF) proliferation (Am. J. Physiol. Heart Circ. Physiol., 2004, 287, H2478-H2486). Adenosine stimulates Cl-secretion in the intestinal epithelia pointing towards a possible treatment for cystic fibrosis patients with CFTR mutation (Am. J. Respir. Cell Mol. Biol., 2008, 39, 190-197). High affinity $A_{2B}$ antagonists are effective in hot plate model suggestive of the role of $A_{2B}$ in nociception and can be used as potential analgesic agents (The J. of Pharmacol. and Exp. Ther., 2004, 308, 358-366).

$A_{2B}$ receptor is involved in release of IL-6. Increasing evidence suggests that IL-6 plays a role in Alzheimer's disease in the context of inflammatory process associated with disease. Hence $A_{2B}$ receptor antagonist might be useful for Alzheimer's disease.

The $A_{2B}$ ARs are involved in the stimulation of nitric oxide production during $Na^+$-linked glucose or glutamine absorption. They are involved in glucose production in hepatocytes upon agonist stimulation. $A_{2B}$-receptor antagonists showed an anti-diabetic potential mainly by increasing plasma insulin levels under conditions when the adenosine tonus was elevated in-vivo and increased insulin release in-vitro (J Pharm. Pharmacol. 2006 December; 58(12); 1639-45). Thus, $A_{2B}$ antagonists may serve as a novel target for the treatment of this metabolic disease.

It has been demonstrated that adenosine activation of the $A_{2B}$ adenosine receptor increase cAMP accumulation, cell proliferation and VEGF expression in human retinal endothelial cells. Activation of $A_{2B}$AdoR increased vascular endothelial cell growth factor mRNA and protein expression in human retinal endothelial cells. Adenosine also has a synergistic effect with VEGF on retinal endothelial cell proliferation and capillary morphogenesis in vitro. Such activity is necessary in healing wounds, but the hyperproliferation of endothelial cells promotes diabetic retinopathy. Also, an undesirable increase in blood vessels occurs in neoplasia. Accordingly, inhibition of binding of adenosine to $A_{2B}$ receptors in the endothelium will alleviate or prevent hypervasculation, thus preventing retinopathy and inhibiting tumor formation.

Adenosine generation in tumor microenvironment is an active metabolic mechanism used by cancer cells to avoid anti-tumor immunosurveillance and increase metastasis. Ectonucleotidase CD73 and CD39 (highly expressed on tumor cells and stromal cells) convert ATP released by dying tumor cells to adenosine. $A_{2B}$ receptors are expressed at low levels on multiple cell types under normal conditions, but significantly upregulated under hypoxic conditions that prevail in the tumor microenvironment. Activation of $A_{2B}$ receptors promotes angiogenesis and causes T cell and myeloid derived suppressor cell (MDSC) mediated immunosuppression in the tumor microenvironment. $A_{2B}$ antagonists could induce anti-tumoral responses in multiple types of cancer when used as stand alone or in combination with existing immunotherapies or radiotherapy or chemotherapy. Cancers that could benefit from $A_{2B}$ antagonist therapy include melanoma, triple negative breast cancer, colon cancer, colorectal cancer, lung cancer, prostate cancer, renal cell cancer, non-small cell lung cancer, bladder cancer, cervical, vulvar or anal cancer, esophageal cancer, metastatic head and neck cancer, liver cancer, lymphoma, multiple myeloma, ovarian cancer, pancreatic cancer, acute myeloid leukemia, Kaposi sarcoma.

EP417790 discloses compounds represented by the formula:

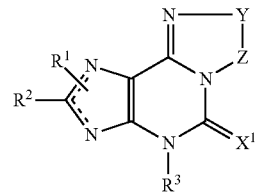

wherein each symbol is as defined in the specification, useful as bronchodilators, diuretics, renal protectants, and antiamnestic agents.

WO200107441 discloses compounds represented by the formula:

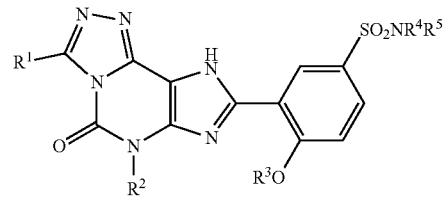

wherein each symbol is as defined in the specification, useful as PDE 5 inhibitors.

WO200244182 and WO200322284 disclose compounds represented by the formula:

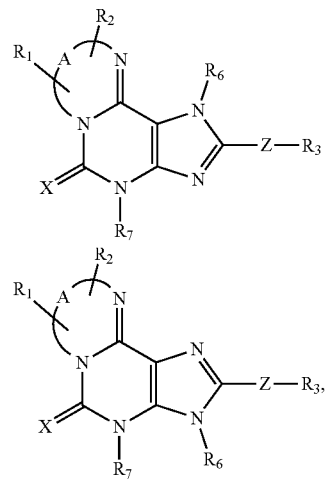

wherein each symbol is as defined in the specification, useful as Adenosine $A_1$ receptor antagonist.

While many of these biological effects of adenosine are necessary to maintain normal tissue homeostasis, under certain physiological changes it is desirable to modulate its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adenosine to $A_{2B}$ receptors in the endothelium will alleviate or prevent hypervasculation, thus preventing retinopathy and inhibiting tumor formation.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion and are thus useful in the treatment of inflammatory gastrointestinal tract disorders, including diarrhea. Another adverse biological effect of adenosine acting at the $A_{2B}$ receptor is the over-stimulation of cerebral IL-6, a cytokine associated with dementias and Alzheimer's disease.

Accordingly, it is desired to provide compounds that are potent $A_{2A}/A_{2B}$ dual antagonists (i.e., compounds that inhibit the $A_{2A}/A_{2B}$ adenosine receptor), fully or partially selective for the $A_{2A}/A_{2B}$ receptor, useful in the treatment of various disease states related to modulation of the $A_{2A}/A_{2B}$ receptor, for example cancer.

SUMMARY OF THE INVENTION

In an aspect of the present disclosure, there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof,

D-A-B-Z    (I)

wherein
D represents a tricyclic ring system selected from

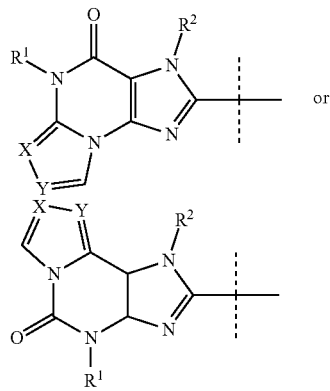

or wherein $R^1$ is selected from alkyl, cycloalkyl, cycloalkylalkyl, aryl, arylalkyl, heterocyclyl, heterocyclylalkyl, heteroaryl, or heteroarylalkyl;
$R^2$ is selected from hydrogen, alkyl, alkenyl, alkynyl, alkoxyalkyl, cycloalkyl, cycloalkylalkyl, aryl, arylalkyl, heteroaryl, or heteroarylalkyl;
wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^cR^c$, —$NR^cS(O)_2R^c$ or —$S(O)_p R^d$;
wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —$S(O)_pR^d$;
X and Y are independently selected from CR' or N, wherein R' is selected from hydrogen, halogen, alkyl and haloalkyl;
A is selected from an optionally substituted arylene or an optionally substituted heteroarylene;
B is selected from a bond, $(C_1-C_6)$alkylene, $(C_2-C_6)$alkenylene or $(C_2-C_6)$alkynylene group, wherein 1 to 4 methylene groups are optionally replaced by groups independently selected from O, —$S(O)_p$—, —$N(R^b)$—, or —$C(O)$—;
wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^cR^c$, —$NR^cS(O)_2R^c$ or —$S(O)_pR^d$;
Z is selected from hydrogen, heterocyclyl, cycloalkyl, aryl or heteroaryl;
wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —$S(O)_2NR^bR^b$, —$NR^bS(O)_2R^b$ or —$S(O)_pR^d$;
wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —$S(O)_pR^d$;
$R^a$ is selected from hydrogen, or alkyl;
$R^b$ is selected from hydrogen, alkyl, acyl, carboxyalkyl, carbonylamino, cycloalkyl, cycloalkylalkyl, aryl, arylalkyl, heteroaryl, heteroarylalkyl, heterocyclyl, or heterocyclylalkyl;
$R^c$ is selected from hydrogen, alkyl, aryl, heteroaryl, or heterocyclyl;
$R^d$ is selected from alkyl, cycloalkyl, aryl, heterocyclyl, or heteroaryl; and
p is 0, 1, or 2.

In an aspect of the present disclosure there is provided a method of using the pharmaceutical composition of the present disclosure comprising a compound of Formula I and their pharmaceutically acceptable salt, analog, tautomeric form, stereoisomer, geometrical isomer, polymorph, hydrate, solvate, metabolite, and prodrug thereof, in the treatment of a disease or condition in a mammal that is amenable to treatment with an $A_{2A}/A_{2B}$ receptor antagonist, the method comprising: administering to a mammal in need thereof a therapeutically effective dose of the pharmaceutical composition of the present disclosure.

In an aspect of the present disclosure there is provided a method of treatment of a disorder or condition ameliorated by antagonizing the $A_{2A}/A_{2B}$ receptor, the method comprising: administering an effective amount of the pharmaceutical composition of the present disclosure comprising a compound of Formula I and their pharmaceutically acceptable salts, analog, tautomeric form, stereoisomer, geometrical isomer, polymorph, hydrate, solvate, metabolite, and prodrug thereof, to a patient in need of such treatment.

In an aspect of the present disclosure there is provided use of the pharmaceutical composition of the present disclosure comprising compound of Formula I and their pharmaceutically acceptable salt, analog, tautomeric form, stereoisomer, geometrical isomer, polymorph, hydrate, solvate, metabolite, and prodrug thereof, for the preparation of a medicament for the treatment of a condition or disorder selected from prostate cancer, rectal cancer, renal cancer, ovarian cancer, endometrial cancer, thyroid cancer, pancreatic cancer, breast cancer, colon cancer, bladder cancer, brain cancer, glial cancer, melanoma cancer, pineal gland cancer, or lung cancer.

In an aspect of the present disclosure, there is provided a process of preparation of the compound of Formula I.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkyl" or "substituted alkylene" refers to:
1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulfur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or —$S(O)_pR^c$, in which $R^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo [2.2.1] heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is alkyl, aryl, or heteroaryl and p is 0, 1 or 2.

The term "cycloalkyl" refers to carbocyclic groups of from 3 to 20 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, 1,3,3-trimethylbicyclo[2.2.1]hept-2-yl, 2,3,3-trimethylbicyclo[2.2.1]hept-2-yl, or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cycloalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'''—O—, where R''' is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e. g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —$S(O)_pR^c$, where $R^c$ is alkyl, aryl, or heteroaryl and p is 0, 1 or 2.

The term "alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

The term "aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

The term "di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

The term "cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "aminoalkyl" refers to an amino group that is attached to ($C_{1-6}$) alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —$SO_3H$, aryl, aryloxy, heteroaryl, aminosulfonyl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$ where each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where $R^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_p R^c$ where $R^c$ is hydrogen, alkyl, aryl, or heteroaryl and p is 0, 1 or 2.

The term "arylalkyl" refers to an aryl group covalently linked to an alkylene group, where aryl and alkylene are defined herein.

The term "optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group —O-aryl, wherein the aryl group is as defined above and includes optionally substituted aryl groups as also defined above.

The term "arylthio" refers to the group —S-aryl, where aryl group is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "carboxyalkyl" refers to the group -alkylene-C(O)OH.

The term "alkylcarboxyalkyl" refers to the group -alkylene-C(O)O$R^d$ where $R^d$ is alkyl, cycloalkyl, where alkyl, cycloalkyl are as defined herein, and may be optionally further substituted by alkyl, halogen, $CF_3$, amino, substituted amino, cyano, or —$S(O)_pR^c$, in which $R^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

The term "optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cycloalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)$_p$R$^b$, where R$^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)R$^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

The term "optionally substituted heterocyclylalkyl" refers to an optionally substituted heterocyclyl group covalently linked to an optionally substituted alkylene group.

The term "heteroaryloxy" refers to the group —O-heteroaryl.

The term "thiol" refers to the group —SH.

The term "carboxy" refers to —C(O).

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

The term "substituted sulfoxide" refers to a group —S(O) R, in which R is substituted alkyl, substituted aryl, or substituted heteroaryl, as defined above.

The term "sulfone" refers to a group —S(O)$_2$R, where R is alkyl, aryl, or heteroaryl.

The term "substituted sulfone" refers to a group —S(O)$_2$R, in which R is alkyl, aryl, or heteroaryl.

The term "disorder or condition ameliorated by the inhibition of the $A_{2A}$ receptor" will be understood by those skilled in the art to include: cancer such as prostate, rectal, renal, ovarian, endometrial, thyroid, pancreatic, particularly breast, colon, bladder, brain, glia, melanoma, pineal gland and, more particularly, lung cancer (e.g. Lewis lung carcinoma).

The compounds of the present disclosure may have the ability to crystallize in more than one form, a characteristic known as polymorphism, and all such polymorphic forms ("polymorphs") are encompassed within the scope of the invention. Polymorphism generally can occur as a response to changes in temperature or pressure or both and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as "stereoisomers", such as double-bond isomers (i.e., "geometric isomers"), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof.

Accordingly, the chemical structures depicted herein encompass all possible tautomeric forms of the illustrated or identified compounds.

Compounds may exist in unsolvated forms as well as solvated forms, including hydrated forms. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

The term "prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

The term "therapeutically effective dose" means an amount of a compound or composition which is sufficient enough to significantly and positively modify the symptoms and/or conditions to be 10 treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge 15 and expertise of the attending physician.

The term "promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

The phrase "pharmaceutically acceptable excipient" refers to compounds or compositions that are physiologically tolerable and do not typically produce allergic or similar untoward reactions, including but not limited to gastric upset or dizziness when administered to mammal.

The term "pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X–) is associated with the positive charge of the N atom. X– may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X– is preferably an anion selected from chloride, bromide, iodide, sulphate, nitrate, acetate, maleate, oxalate, succinate or trifluoroacetate. More preferably X– is chloride, bromide, trifluoroacetate or methanesulphonate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents. The term "q.s." means adding a quantity sufficient to achieve a stated function, e.g., to bring a solution to the desired volume (i.e., 100%).

Furthermore, the compound of Formula I can be its derivatives, analogs, stereoisomer's, diastereomers, geometrical isomers, polymorphs, solvates, co-crystals, intermediates, hydrates, metabolites, prodrugs or pharmaceutically acceptable salts and compositions.

It is understood that included in the family of compounds of Formula I are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers and geometrical isomers can be separated by physical and/or chemical methods by those skilled in the art.

Compounds disclosed herein may exist as single stereoisomers, racemates and or mixtures of enantiomers and/or diastereomers. All such single stereoisomers, racemates and mixtures thereof are intended to be within the scope of the subject matter described.

Compounds disclosed herein include isotopes of hydrogen, carbon, oxygen, fluorine, chlorine, iodine and sulfur which can be incorporated into the compounds, such as, but not limited to, $^2$H (D), $^3$H (T), $^{11}$C, $^{13}$C, $^{14}$C, $^{15}$N, $^{18}$F, $^{35}$S, $^{36}$Cl, and $^{125}$I. Compounds of this disclosure wherein atoms were isotopically labeled, for example radioisotopes such as $^3$H, $^{13}$C, $^{14}$C, and the like can be used in metabolic studies, kinetic studies, and imaging techniques such as positron emission tomography used in understanding the tissue distribution of the drugs. Compounds of the disclosure where hydrogen is replaced with deuterium may improve the metabolic stability, and pharmacokinetics properties of the drug such as in vivo half-life.

In an embodiment of the present disclosure, there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof,

D-A-B-Z         (I)

Formula I wherein
D represents a tricyclic ring system selected from

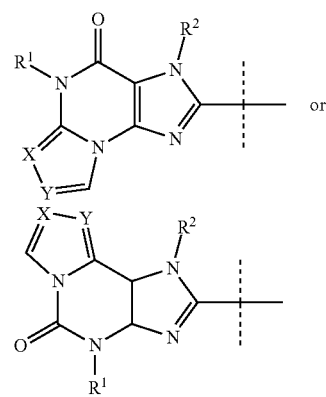

wherein R¹ is selected from alkyl, cycloalkyl, cycloalkylalkyl, aryl, arylalkyl, heterocyclyl, heterocyclylalkyl, heteroaryl, or heteroarylalkyl;

R² is selected from hydrogen, alkyl, alkenyl, alkynyl, alkoxyalkyl, cycloalkyl, cycloalkylalkyl, aryl, arylalkyl, heteroaryl, or heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO₃H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)₂NR$^c$R$^c$, —NR$^c$ S(O)₂R$^c$ or —S(O)$_p$ R$^d$;

wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;

X and Y are independently selected from CR' or N, wherein R' is selected from hydrogen, halogen, alkyl and haloalkyl;

A is selected from an optionally substituted arylene or an optionally substituted heteroarylene;

B is selected from a bond, (C₁-C₆)alkylene, (C₂-C₆)alkenylene or (C₂-C₆)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO₃H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)₂NR$^c$R$^c$, —NR$^c$ S(O)₂R$^c$ or —S(O)$_p$R$^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO₃H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)₂NR$^b$R$^b$, —NR$^b$S(O)₂R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

R$^a$ is selected from hydrogen, or alkyl;
R$^b$ is selected from hydrogen, alkyl, acyl, carboxyalkyl, carbonylamino, cycloalkyl, cycloalkylalkyl, aryl, arylalkyl, heteroaryl, heteroarylalkyl, heterocyclyl, or heterocyclylalkyl;
R$^c$ is selected from hydrogen, alkyl, aryl, heteroaryl, or heterocyclyl;
R$^d$ is selected from alkyl, cycloalkyl, aryl, heterocyclyl, or heteroaryl; and
p is 0, 1, or 2.

In an embodiment of the present disclosure there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof, wherein D represents a tricyclic ring system selected from

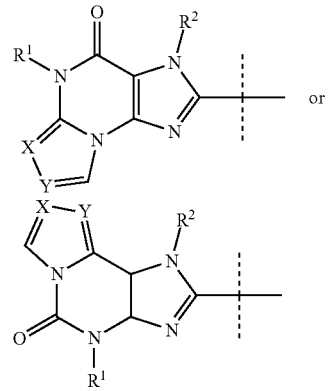

wherein R¹ is selected from alkyl, cycloalkyl, aryl, arylalkyl, heterocyclyl, heteroaryl, or heteroarylalkyl;

R² is selected from hydrogen, alkyl, alkenyl, alkynyl, cycloalkyl, aryl, arylalkyl, heteroaryl, or heteroarylalkyl, wherein alkyl, alkenyl, alkynyl, cycloalkyl, aryl, arylalkyl, heteroaryl, and heteroarylalkyl are unsubstituted or substituted independently with alkyl, alkenyl, alkynyl, cycloalkyl, cycloalkenyl, acyl, acylamino, amino, monoalkylamino, dialkylamino, arylamino, cycloalkylamino, heteroarylamino, heterocyclylamino, aminocarbonyl, azido, cyano, halogen, hydroxy, hydroxyalkyl, keto, thiocarbonyl, carboxy, alkylcarboxy, carboxyalkyl, —SO₃H, aryl, cycloalkyloxy, heteroaryl, aminocarbonylamino, heterocyclyl, heterocyclyloxy, hydroxyamino, nitro, S(O)₂NR$^c$R$^c$, —NR$^c$ S(O)₂ R$^c$ or —S(O)$_p$R$^d$; wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;

X and Y are independently selected from CR' or N, wherein R' is selected from hydrogen, halogen, or alkyl;

A is selected from an optionally substituted arylene or an optionally substituted heteroarylene;

B is selected from a bond, (C₁-C₆)alkylene, or (C₂-C₆) alkynylene group, wherein 1 to 3 methylene groups are optionally replaced by groups independently selected from O, —S(O)$_p$—, or —C(O)—;

wherein alkylene, and alkynylene are unsubstituted or substituted independently with alkyl, alkenyl, alkynyl, alkoxy, cycloalkyl, cycloalkenyl, acyl, acyloxy, azido, cyano, halogen, hydroxy, hydroxyalkyl, keto, thiocarbonyl, alkylcarboxy, carboxyalkyl, carboxyalkyloxy, alkylcarboxyalkyloxy —SO₃H, aryl, aryloxy, cycloalkyloxy, heteroaryl, heteroaryloxy, heterocyclyl, heterocyclyloxy, hydroxyamino, nitro, S(O)$_2$NR$^c$R$^c$, or —S(O)$_p$R$^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, cyano, halogen, hydroxy, hydroxyalkyl, keto, thiocarbonyl, carboxy, alkylcarboxy, carboxyalkyl, carboxyalkyloxy, alkylcarboxyalkyloxy, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;

R$^a$ is selected from hydrogen, or alkyl;

R$^b$ is selected from hydrogen, alkyl, acyl, carboxyalkyl, carbonylamino, cycloalkyl, cycloalkylalkyl, aryl, arylalkyl, heteroaryl, heteroarylalkyl, heterocyclyl, or heterocyclylalkyl;

R$^c$ is selected from hydrogen, alkyl, aryl, heteroaryl, or heterocyclyl;

R$^d$ is selected from alkyl, cycloalkyl, aryl, heterocyclyl, or heteroaryl; and p is 0, 1, or 2.

In an embodiment of the present disclosure there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof, wherein D represents a tricyclic ring system selected from

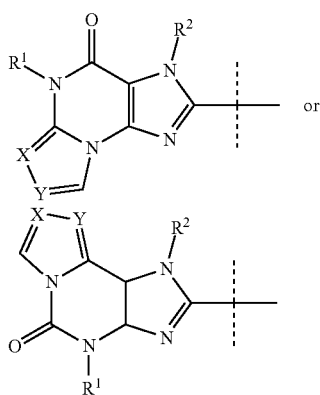

wherein R$^1$ is selected from alkyl, cycloalkyl, aryl, or arylalkyl,

R$^2$ is selected from hydrogen, alkyl, alkenyl, alkynyl, cycloalkyl, or aryl, wherein alkyl, alkenyl, alkynyl, cycloalkyl, aryl, are unsubstituted or substituted independently with alkyl, alkenyl, alkynyl, cycloalkyl, cycloalkenyl, acyl, acylamino, amino, monoalkylamino, dialkylamino, arylamino, cycloalkylamino, heteroarylamino, heterocyclylamino, aminocarbonyl, azido, cyano, halogen, hydroxy, hydroxyalkyl, keto, thiocarbonyl, carboxy, alkylcarboxy, carboxyalkyl, —SO$_3$H, aryl, cycloalkyloxy, heteroaryl, aminocarbonylamino, heterocyclyl, heterocyclyloxy, hydroxyamino, nitro, S(O)$_2$NR$^c$R$^c$, —NR$^c$ S(O)$_2$R$^c$ or —S(O)$_p$R$^d$; wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;

X and Y are independently selected from CR' or N, wherein R' is selected from hydrogen, halogen, or alkyl;

A is selected from an optionally substituted arylene or an optionally substituted heteroarylene;

B is selected from a bond, (C$_1$-C$_6$)alkylene, or (C$_2$-C$_6$) alkynylene group, wherein 1 to 3 methylene groups are optionally replaced by groups independently selected from O, —S(O)$_p$—, or —C(O)—;

wherein alkylene, and alkynylene are unsubstituted or substituted independently with alkyl, alkenyl, alkynyl, alkoxy, cycloalkyl, cycloalkenyl, acyl, acyloxy, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, heteroaryloxy, heterocyclyl, heterocyclyloxy, hydroxyamino, nitro, S(O)$_2$NR$^c$R$^c$, or —S(O)$_p$R$^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, cyano, halogen, hydroxy, hydroxyalkyl, keto, thiocarbonyl, carboxy, alkylcarboxy, carboxyalkyl, carboxyalkyloxy, alkylcarboxyalkyloxy, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;

R$^a$ is selected from hydrogen, or alkyl;

R$^b$ is selected from hydrogen, alkyl, aryl, arylalkyl, heteroaryl, or heterocyclylalkyl;

R$^c$ is selected from hydrogen, alkyl, aryl, heteroaryl, or heterocyclyl;

R$^d$ is selected from alkyl, cycloalkyl, aryl, heterocyclyl, or heteroaryl; and p is 1, or 2.

In an embodiment of the present disclosure there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof, wherein D represents a tricyclic ring system selected from

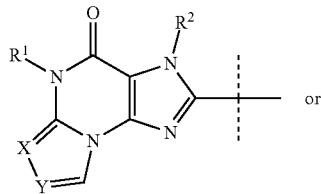

-continued

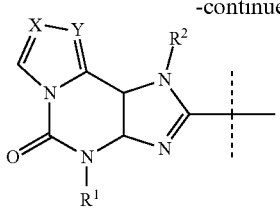

wherein R¹ is selected from alkyl;
R² is selected from hydrogen, or alkyl, wherein alkyl, is unsubstituted or substituted independently with alkyl, alkenyl, alkynyl, cycloalkyl, cycloalkenyl, acyl, acylamino, amino, monoalkylamino, dialkylamino, cycloalkylamino, heteroaryl, aminocarbonylamino, heterocyclyl, heterocyclyloxy, hydroxyamino, nitro, $S(O)_2NR^cR^c$, —$NR^c S(O)_2R^c$ or —$S(O)_pR^d$;
wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —$S(O)_pR^d$;
X and Y are independently selected from CR' or N, wherein R' is selected from hydrogen, halogen, or alkyl;
A is selected from an optionally substituted arylene or an optionally substituted heteroarylene;
B is selected from a bond, $(C_1-C_6)$alkylene, or $(C_2-C_6)$alkynylene group, wherein 1 to 3 methylene groups are optionally replaced by groups independently selected from O, —$S(O)_p$—, or —C(O)—;
wherein alkylene, and alkynylene are unsubstituted or substituted independently with alkyl, alkenyl, alkynyl, alkoxy, cycloalkyl, cycloalkenyl, acyl, acyloxy, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, heteroaryloxy, heterocyclyl, heterocyclyloxy, hydroxyamino, nitro, $S(O)_2NR^cR^c$, or —$S(O)_pR^d$;
Z is selected from hydrogen, heterocyclyl, aryl or heteroaryl; wherein heterocyclyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, halogen, hydroxy, hydroxyalkyl, keto, thiocarbonyl, carboxy, aryl, arylalkyl, aryloxy, cycloalkyloxy, heteroaryl, heteroarylalkyl, heteroaryloxy, heterocyclyl, heterocyclylalkyl, heterocyclyloxy, —$S(O)_2NR^bR^b$, —$NR^bS(O)_2R^b$ or —$S(O)_pR^d$;
wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;
$R^a$ is selected from hydrogen, or alkyl;
$R^b$ is selected from hydrogen, alkyl, aryl, arylalkyl, heteroaryl, or heterocyclylalkyl;
$R^c$ is selected from hydrogen, alkyl, aryl, heteroaryl, or heterocyclyl;
$R^d$ is selected from alkyl, cycloalkyl, aryl, heterocyclyl, or heteroaryl; and
p is 0, 1, or 2.
In an embodiment of the present disclosure there is provided a compound of Formula I, or its stereoisomers, pharmaceutically acceptable salts, complexes, hydrates, solvates, tautomers, polymorphs, prodrugs, racemic mixtures, optically active forms and pharmaceutically active derivatives thereof, wherein the compound of Formula I is selected from the group consisting of:
5-propyl-2-[1-[[3-(trifluoromethyl)phenyl]methyl]pyrazol-4-yl]-3H-imidazo[2,1-b]purin-4-one (A1),
2-(1-benzylpyrazol-4-yl)-5-propyl-3H-imidazo[2,1-b]purin-4-one (A2),
5-methyl-2-[1-[[3-(trifluoromethyl)phenyl]methyl]pyrazol-4-yl]-3H-imidazo[2,1-b]purin-4-one (A3),
5-propyl-2-[1-[2-[3-(trifluoromethyl)phenyl]ethyl]pyrazol-4-yl]-3H-imidazo[2,1-b]purin-4-one (A4),
2-[1-[2-(3-fluorophenyl)ethyl]pyrazol-4-yl]-5-propyl-3H-imidazo[2,1-b]purin-4-one (A5),
2-(1-methylpyrazol-4-yl)-5-propyl-3H-imidazo [2, 1-b] purin-4-one (A6),
2-[1-(1,1-dimethylpropyl)pyrazol-4-yl]-5-propyl-3H-imidazo[2,1-b]purin-4-one (A7),
N-isopropyl-3-[3-[4-(4-oxo-5-propyl-3H-imidazo[2,1-b]purin-2-yl)pyrazol-1-yl]prop-1-ynyl]benzamide (B1),
Ethyl 3-[3-[4-(4-oxo-5-propyl-3H-imidazo[2,1-b]purin-2-yl)pyrazol-1-yl]prop-1-ynyl]benzoate (B2),
5-propyl-2-[1-[3-[3-(trifluoromethoxy)phenyl]prop-2-ynyl]pyrazol-4-yl]-3H-imidazo[2,1-b]purin-4-one (B3),
Ethyl 4-methyl-3-[3-[4-(4-oxo-5-propyl-3H-imidazo[2,1-b]purin-2-yl)pyrazol-1-yl]prop-1-ynyl]benzoate (B6),
3-[[4-(4-oxo-5-propyl-3H-imidazo[2,1-b]purin-2-yl)pyrazol-1-yl]methyl]benzonitrile (B7),
2-(1-isopropylpyrazol-4-yl)-5-propyl-3H-imidazo[2,1-b]purin-4-one (B8),
2-(1-butylpyrazol-4-yl)-5-propyl-3H-imidazo[2,1-b]purin-4-one (B9),
2-(1-ethylpyrazol-4-yl)-5-propyl-3H-imidazo[2,1-b]purin-4-one (B10),
2-[1-(2-methoxyethyl)pyrazol-4-yl]-5-propyl-3H-imidazo[2,1-b]purin-4-one (B11),
2-[1-(2-dimethylaminoethyl)pyrazol-4-yl]-5-propyl-3H-imidazo[2,1-b]purin-4-one (B12),
5-propyl-2-(1-propylpyrazol-4-yl)-3H-imidazo[2,1-b]purin-4-one (B13),
N,N-dimethyl-2-[4-(4-oxo-5-propyl-3H-imidazo[2,1-b]purin-2-yl)pyrazol-1-yl]acetamide (B14),
2-[1-(2-morpholinoethyl)pyrazol-4-yl]-5-propyl-3H-imidazo[2,1-b]purin-4-one (B15),
2-[1-(cyclobutylmethyl)pyrazol-4-yl]-5-propyl-3H-imidazo[2,1-b]purin-4-one (B16),
2-(1-isobutylpyrazol-4-yl)-5-propyl-3H-imidazo[2,1-b]purin-4-one (B17),
2-[1-(cyclopropylmethyl)pyrazol-4-yl]-5-propyl-3H-imidazo[2,1-b]purin-4-one (B18),
2-[1-(2,2-dimethylpropyl)pyrazol-4-yl]-5-propyl-3H-imidazo[2,1-b]purin-4-one (B19),
5-propyl-2-(1-sec-butylpyrazol-4-yl)-3H-imidazo[2,1-b]purin-4-one (B20),
5-propyl-2-[1-(tetrahydrofuran-2-ylmethyl)pyrazol-4-yl]-3H-imidazo[2,1-b]purin-4-one (B21),
2-[1-[[5-oxo-1-[2-(trifluoromethyl)-4-pyridyl]pyrrolidin-3-yl]methyl]pyrazol-4-yl]-5-propyl-3H-imidazo[2,1-b]purin-4-one (C1),
2-[1-[[5-oxo-1-[5-(trifluoromethyl)-3-pyridyl]pyrrolidin-3-yl]methyl]pyrazol-4-yl]-5-propyl-3H-imidazo[2,1-b]purin-4-one (C2),
2-[1-[[5-oxo-1-[3-(trifluoromethyl)phenyl]pyrrolidin-3-yl]methyl]pyrazol-4-yl]-5-propyl-3H-imidazo[2,1-b]purin-4-one (C3),
2-[1-[2-(1-piperidyl)ethyl]pyrazol-4-yl]-5-propyl-3H-imidazo[2,1-b]purin-4-one (D1), 2-[1-[[3-(hydroxymethyl)phenyl]methyl]pyrazol-4-yl]-5-propyl-3H-imidazo[2,1-b]purin-4-one (E1),
2-[1-[[3-(1-hydroxy-1-methyl-ethyl)phenyl]methyl]pyrazol-4-yl]-5-propyl-3H-imidazo[2,1-b]purin-4-one (F1),
3-[[4-(4-oxo-5-propyl-3H-imidazo[2,1-b]purin-2-yl)pyrazol-1-yl]methyl]benzoic acid (G1),
2-[4-(4-oxo-5-propyl-3H-imidazo[2,1-b]purin-2-yl)pyrazol-1-yl]acetic acid (H1),
2-[1-(2-hydroxy-2-methyl-propyl)pyrazol-4-yl]-5-propyl-3H-imidazo[2,1-b]purin-4-one (I1),
2-[1-(2,3-dihydroxypropyl)pyrazol-4-yl]-5-propyl-3H-imidazo[2,1-b]purin-4-one (J1),
2-(3,4-dimethoxyphenyl)-5-propyl-3H-imidazo[2,1-b]purin-4-one (K1),
5-propyl-2-[3-(trifluoromethyl)phenyl]-3H-imidazo[2,1-b]purin-4-one (K2),
2-[1-[(3-fluorophenyl)methyl]pyrazol-4-yl]-5-propyl-3H-imidazo[2,1-b]purin-4-one (K3),
2-[1-[(3-methoxyphenyl)methyl]pyrazol-4-yl]-5-propyl-3H-imidazo[2,1-b]purin-4-one (K4),
2-[4-[2-(1-piperidyl)ethoxy]phenyl]-5-propyl-3H-imidazo[2,1-b]purin-4-one (K5),
2-(5-methoxy-2-pyridyl)-5-propyl-3H-imidazo[2,1-b]purin-4-one (K6),
2-(4-ethoxyphenyl)-5-propyl-3H-imidazo[2,1-b]purin-4-one (K7),
N-isopropyl-2-[4-(4-oxo-5-propyl-3H-imidazo[2,1-b]purin-2-yl)pyrazol-1-yl]acetamide (L1),
N-(oxetan-3-yl)-2-[4-(4-oxo-5-propyl-3H-imidazo[2,1-b]purin-2-yl)pyrazol-1-yl]acetamide (L2),
4-propyl-2-[1-[[3-(trifluoromethyl)phenyl]methyl] pyrazol-4-yl]-1H-imidazo[2,1-f]purin-5-one (II),
2-[1-(2-furylmethyl)pyrazol-4-yl]-5-propyl-3H-imidazo[2,1-b]purin-4-one (III),
5-propyl-2-[1-(2-thienylmethyl)pyrazol-4-yl]-3H-imidazo[2,1-b]purin-4-one (IV),
2-[1-(oxazol-2-ylmethyl)pyrazol-4-yl]-5-propyl-3H-imidazo[2,1-b]purin-4-one (V),
2-[1-(isoxazol-5-ylmethyl)pyrazol-4-yl]-5-propyl-3H-imidazo[2,1-b]purin-4-one (VI),
2-[1-[(5-methyl-2-thienyl)methyl]pyrazol-4-yl]-5-propyl-3H-imidazo[2,1-b]purin-4-one (VII),
2-[1-[(3,5-difluorophenyl)methyl]pyrazol-4-yl]-5-propyl-3H-imidazo[2,1-b]purin-4-one (VIII),
5-propyl-2-[1-(4-pyridylmethyl)pyrazol-4-yl]-3H-imidazo[2,1-b]purin-4-one (IX),
5-propyl-2-[1-(3-pyridylmethyl)pyrazol-4-yl]-3H-imidazo[2,1-b]purin-4-one (X),
5-propyl-2-[1-(2-pyridylmethyl)pyrazol-4-yl]-3H-imidazo[2,1-b]purin-4-one (XI),
5-propyl-2-[1-(pyrimidin-5-ylmethyl)pyrazol-4-yl]-3H-imidazo[2,1-b]purin-4-one (XII),
5-propyl-2-[1-(pyridazin-4-ylmethyl)pyrazol-4-yl]-3H-imidazo[2,1-b]purin-4-one (XIII),
2-[1-[(1-oxoisoindolin-5-yl)methyl]pyrazol-4-yl]-5-propyl-3H-imidazo[2,1-b]purin-4-one (XIV),
2-[1-[(2-methyl-1-oxo-isoindolin-5-yl)methyl]pyrazol-4-yl]-5-propyl-3H-imidazo[2,1-b]purin-4-one (XV),
2-[1-[(1-oxo-3,4-dihydro-2H-isoquinolin-6-yl)methyl]pyrazol-4-yl]-5-propyl-3H-imidazo[2,1-b]purin-4-one (XVI),
2-[1-[(2-oxo-3,4-dihydro-1H-quinolin-6-yl)methyl]pyrazol-4-yl]-5-propyl-3H-imidazo[2,1-b]purin-4-one (XVII),
5-propyl-2-[1-(quinoxalin-6-ylmethyl)pyrazol-4-yl]-3H-imidazo[2,1-b]purin-4-one (XVIII),
2-[1-(2-naphthylmethyl)pyrazol-4-yl]-5-propyl-3H-imidazo[2,1-b]purin-4-one (XIX),
2-[1-[[3-(azetidin-3-yl)phenyl]methyl]pyrazol-4-yl]-5-propyl-3H-imidazo[2,1-b]purin-4-one (XX),
2-[1-[[3-(2-methoxyethoxy)phenyl]methyl]pyrazol-4-yl]-5-propyl-3H-imidazo[2,1-b]purin-4-one (XXI),
2-[1-[[4-(2-methoxyethoxy)phenyl]methyl]pyrazol-4-yl]-5-propyl-3H-imidazo[2,1-b]purin-4-one (XXII),
5-propyl-2-[1-[3-[3-(trifluoromethyl)phenyl]prop-2-ynyl]pyrazol-4-yl]-3H-imidazo[2,1-b]purin-4-one (XXIII),
2-[1-[3-(3-fluorophenyl)prop-2-ynyl]pyrazol-4-yl]-5-propyl-3H-imidazo[2,1-b]purin-4-one (XXIV),
2-[1-[3-(4-fluorophenyl)prop-2-ynyl]pyrazol-4-yl]-5-propyl-3H-imidazo[2,1-b]purin-4-one (XXV),
5-propyl-2-[1-[3-[4-(trifluoromethyl)phenyl]prop-2-ynyl]pyrazol-4-yl]-3H-imidazo[2,1-b]purin-4-one (XXVI),
2-[1-[[1-(3-fluorophenyl)-5-oxo-pyrrolidin-3-yl]methyl]pyrazol-4-yl]-5-propyl-3H-imidazo[2,1-b]purin-4-one (XXVII),
2-[1-[[1-(m-tolyl)-5-oxo-pyrrolidin-3-yl]methyl]pyrazol-4-yl]-5-propyl-3H-imidazo[2,1-b]purin-4-one (XXVIII),
2-[1-[(3-chloro-5-fluoro-phenyl)methyl]pyrazol-4-yl]-5-propyl-3H-imidazo[2,1-b]purin-4-one (XXIX),
2-[[4-(4-oxo-5-propyl-3H-imidazo[2,1-b]purin-2-yl)pyrazol-1-yl]methyl]benzonitrile (XXX),
2-[1-[(2-fluorophenyl)methyl]pyrazol-4-yl]-5-propyl-3H-imidazo[2,1-b]purin-4-one (XXXI),
4-[[4-(4-oxo-5-propyl-3H-imidazo[2,1-b]purin-2-yl)pyrazol-1-yl]methyl]benzonitrile (XXXII),
2-[1-[[3-(4-methylpiperazin-1-yl)phenyl]methyl]pyrazol-4-yl]-5-propyl-3H-imidazo[2,1-b]purin-4-one (XXXIII),
2-[1-[1-(3-fluorophenyl)ethyl]pyrazol-4-yl]-5-propyl-3H-imidazo[2,1-b]purin-4-one (XXXIV),
2-[1-[(4-isopropylphenyl)methyl]pyrazol-4-yl]-5-propyl-3H-imidazo[2,1-b]purin-4-one (XXXV),
5-propyl-2-[1-(2,2,2-trifluoroethyl)pyrazol-4-yl]-3H-imidazo[2,1-b]purin-4-one (XXXVI),
2-[1-(2-aminoethyl)pyrazol-4-yl]-5-propyl-3H-imidazo[2,1-b]purin-4-one (XXXVII),
5-propyl-2-(1-tetrahydropyran-4-ylpyrazol-4-yl)-3H-imidazo[2,1-b]purin-4-one (XXXVIII),
2-(1-cyclopentylpyrazol-4-yl)-5-propyl-3H-imidazo[2,1-b]purin-4-one (XXXIX),
7-methyl-5-propyl-2-[1-[[3-(trifluoromethyl)phenyl]methyl]pyrazol-4-yl]-3H-imidazo[2,1-b]purin-4-one (XL),
8-methyl-5-propyl-2-[1-[[3-(trifluoromethyl)phenyl]methyl]pyrazol-4-yl]-3H-imidazo[2,1-b]purin-4-one (XLI),
7-methyl-5-propyl-2-(1-propylpyrazol-4-yl)-3H-imidazo[2,1-b]purin-4-one (XLII),
2-(1-ethylpyrazol-4-yl)-7-methyl-5-propyl-3H-imidazo[2,1-b]purin-4-one (XLIII),
7-methyl-2-(1-methylpyrazol-4-yl)-5-propyl-3H-imidazo[2,1-b]purin-4-one (XLIV),
5-propyl-2-(1-propylpyrazol-4-yl)-7-(trifluoromethyl)-3H-imidazo[2,1-b]purin-4-one (XXXXV),
5-propyl-7-(trifluoromethyl)-2-[1-[[3-(trifluoromethyl)phenyl]methyl]pyrazol-4-yl]-3H-imidazo[2,1-b]purin-4-one (XLVI),
2-[1-(m-tolylmethyl)pyrazol-4-yl]-4-propyl-1H-imidazo[2,1-f]purin-5-one (XLVII),
2-[1-[(3-fluorophenyl)methyl]pyrazol-4-yl]-4-propyl-1H-imidazo[2,1-f]purin-5-one (XLVIII),
3-[[4-(5-oxo-4-propyl-1H-imidazo[2,1-f]purin-2-yl)pyrazol-1-yl]methyl]benzonitrile (XLIX),
3-[[4-(4-ethyl-5-oxo-1H-imidazo[2,1-f]purin-2-yl)pyrazol-1-yl]methyl]benzonitrile (L), 3-[1-methyl-1-[4-(4-oxo-5-propyl-3H-imidazo[2,1-b]purin-2-yl)pyrazol-1-yl]ethyl]benzonitrile (LI), 5-propyl-2-[3-[[3-(trifluoromethyl)phenyl]methoxy]isoxazol-5-yl]-3H-imidazo[2,1-b]purin-4-one (LII).

In an embodiment of the present disclosure there is provided a compound of Formula I, or its stereoisomers, pharmaceutically acceptable salts, complexes, hydrates, solvates, tautomers, polymorphs, racemic mixtures, optically active forms and pharmaceutically active derivatives thereof for use as a medicament.

In an embodiment of the present disclosure there is provided a compound of Formula I, or its stereoisomers, pharmaceutically acceptable salts, complexes, hydrates, solvates, tautomers, polymorphs, racemic mixtures, optically active forms and pharmaceutically active derivatives thereof for use in treating conditions and diseases that are mediated by adenosine receptor (AR) activity.

In an embodiment of the present disclosure there is provided a compound of Formula I, or its stereoisomers, pharmaceutically acceptable salts, complexes, hydrates, solvates, tautomers, polymorphs, racemic mixtures, optically active forms and pharmaceutically active derivatives thereof, either alone or in combination with other therapeutic agents for use in methods for treating or lessening the severity of immunotherapies or radiotherapy or chemotherapy.

In an embodiment of the present disclosure there is provided a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier.

In an embodiment of the present disclosure there is provided a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivative thereof together with a pharmaceutically acceptable excipient or a pharmaceutically acceptable diluent.

In an embodiment of the present disclosure there is provided a pharmaceutical composition comprising a compound of Formula I, or its stereoisomers, pharmaceutically acceptable salts, complexes, hydrates, solvates, tautomers, polymorphs, racemic mixtures, optically active forms and pharmaceutically active derivative thereof together with a pharmaceutically acceptable carrier, and in combination with at least one compound and/or compositions having a like therapeutic effect.

In an embodiment of the present disclosure there is provided a pharmaceutical composition comprising a compound of Formula I, or its stereoisomers, pharmaceutically acceptable salts, complexes, hydrates, solvates, tautomers, polymorphs, racemic mixtures, optically active forms, and pharmaceutically active derivative thereof either alone or in combination with other therapeutic agents for use in methods for treating or lessening the severity of immunotherapies or radiotherapy or chemotherapy.

In an embodiment of the present disclosure there is provided a use of compound of Formula I, or its stereoisomers, pharmaceutically acceptable salts, complexes, hydrates, solvates, tautomers, polymorphs, racemic mixtures, optically active forms and pharmaceutically active derivative thereof, in killing or inhibiting the diseases that are mediated by adenosine receptor (AR) activity.

In an embodiment of the present disclosure there is provided a method for treatment of cancer in a subject comprising: administering to the subject an effective amount of the compound of Formula I, or its stereoisomers, pharmaceutically acceptable salts, complexes, hydrates, solvates, tautomers, polymorphs, racemic mixtures, optically active forms and pharmaceutically active derivative thereof.

In an embodiment of the present disclosure there is provided a method for treatment of disorder or condition selected from melanoma, triple negative breast cancer, colon cancer, colorectal cancer, lung cancer, prostate cancer, renal cell cancer, non-small cell lung cancer, bladder cancer, cervical, vulvar or anal cancer, esophageal cancer, metastatic head and neck cancer, liver cancer, lymphoma, multiple myeloma, ovarian cancer, pancreatic cancer, acute myeloid leukemia, or Kaposi sarcoma in a subject comprising: administering to the subject an effective amount of the compound of Formula I, or its stereoisomers, pharmaceutically acceptable salts, complexes, hydrates, solvates, tautomers, polymorphs, racemic mixtures, optically active forms and pharmaceutically active derivative thereof.

In an embodiment of the present disclosure there is provided a method for treatment of disorder or condition selected from melanoma, triple negative breast cancer, colon cancer, colorectal cancer, lung cancer, prostate cancer, renal cell cancer, non-small cell lung cancer, bladder cancer, cervical, vulvar or anal cancer, esophageal cancer, metastatic head and neck cancer, liver cancer, lymphoma, multiple myeloma, ovarian cancer, pancreatic cancer, acute myeloid leukemia, or Kaposi sarcoma in a subject comprising: administering to the subject an effective amount of the a pharmaceutical composition comprising a compound of Formula I, or its stereoisomers, pharmaceutically acceptable salts, complexes, hydrates, solvates, tautomers, polymorphs, racemic mixtures, optically active forms, and pharmaceutically active derivative thereof.

In an embodiment of the present disclosure there is provided a pharmaceutical composition comprising compounds selected from the compound of Formula I, for the manufacture of a medicament for the treatment of a condition or disorder ameliorated by inhibition of the $A_{2A}/A_{2B}$ receptor further comprising a therapeutically effective amount of at least one pharmaceutically acceptable excipient.

In an embodiment of the present disclosure, there is provided a process of preparation of compound of Formula I, the process is selected from Scheme 1, Scheme 2, Scheme 3, Scheme 4, or Scheme 5 as disclosed herein.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically acceptable salts are preferred, although other salts may be useful, such as in isolating or purifying the product.

In an embodiment of the present disclosure, the salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In an embodiment of the present disclosure, the compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

In an embodiment of the present disclosure, there is described a process of preparation of a composition comprising a compound of Formula I or its stereoisomers, pharmaceutically acceptable salts, complexes, hydrates, solvates, tautomers, polymorphs, racemic mixtures, optically active forms and pharmaceutically active derivative thereof together with a carrier.

The present disclosure relates to a process of preparation of pharmaceutical composition comprising a compound of Formula I or its stereoisomers, pharmaceutically acceptable salts, complexes, hydrates, solvates, tautomers, polymorphs, racemic mixtures, optically active forms and pharmaceutically active derivative thereof, together with a pharmaceutically acceptable carrier, optionally in combination with one or more other pharmaceutical compositions.

The compositions of the present disclosure may be obtained by conventional procedures using conventional pharmaceutical excipients well known in the art. Thus, compositions intended for oral use may contain, for example, one or more colouring, sweetening, flavouring and/or preservative agents Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents or procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid); coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the disclosure may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penetrate the cells of interest or stratum corneum, and fuse with the cell membrane, resulting in delivery of the contents of the liposome into the cell. Other suitable formulations can employ niosomes. Niosomes are lipid vesicles similar to liposomes, with membrane consisting largely of nonionic lipids, some forms of which are effective for transporting compounds across the stratum corneum.

Compositions for administration may also be formulated as a depot preparation, which may be administered by implantation or by intramuscular injection. The compositions may be formulated with suitable polymeric or hydrophobic material (as an emulsion in acceptable oil), ion exchange resins, or sparingly soluble derivatives.

The compound of the present disclosure can also be administered in sustained release forms or from sustained release drug delivery systems.

For further information on formulation, drug delivery as well as processing techniques the reader is referred to Remington's Pharmaceutical Sciences (21$^{st}$ Edition, 2005, University of the sciences in Philadelphia, Lippincott William & Wilkins)

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990 and Remington's Pharmaceutical Sciences (21$^{st}$ Edition, 2005, University of the sciences in Philadelphia, Lippincott William & Wilkins).

As stated above the size of the dose required for the therapeutic or prophylactic treatment of a particular disease state will necessarily be varied depending on the host treated, the route of administration and the severity of the illness being treated. Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the disclosure described herein also apply.

EXAMPLES

The following examples provide the details about the synthesis, activities and applications of the compounds of the present disclosure. It should be understood the following is representative only, and that the disclosure is not limited by the details set forth in these examples.

Materials and Methods:

Evaporations were carried out by rotary evaporation in vacuo and work up procedures were carried out after removal of residual solids by filtration; temperatures are quoted as "° C."; operations were carried out at room temperature, that is typically in the range 18 to 26° C. and without the exclusion of air unless otherwise stated, or unless the skilled person would otherwise work under an inert atmosphere; column chromatography (by the flash procedure) was used to purify compounds and was performed on Merck Kieselgel silica (Art. 9385) unless otherwise stated; in general, the course of reactions was followed by TLC, HPLC, or LC/MS and reaction times are given for illustration only; yields are given for illustration only and are not necessarily the maximum attainable; the structure of the end products of the disclosure was generally confirmed by NMR and mass spectral techniques. Proton magnetic resonance spectra were generally determined in DMSO d6 unless otherwise stated, using a Bruker DRX 300 spectrometer or a Bruker DRX-400 spectrometer, operating at a field strength of 300 MHz or 400 MHz, respectively. In cases where the NMR spectrum is complex, only diagnostic signals are reported. Chemical shifts are reported in parts per million downfield from tetramethylsilane as an external standard (δ scale) and peak multiplicities are shown thus: s, singlet; d, doublet; dd, doublet of doublets; dt, doublet of triplets; dm, doublet of multiplets; t, triplet; m, multiplet; br, broad. Fast atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS AQ (100×20 mmID, S 5 Å particle size, 12 nm pore size) on Agilent instruments; each intermediate was purified to the standard required for the subsequent stage and was characterized in sufficient detail to confirm that the assigned structure was correct; purity was assessed by HPLC, TLC, or NMR and identity was determined by infrared spectroscopy (IR), mass spectroscopy or NMR spectroscopy as appropriate.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature or could be made from commercially available compounds using adaptations of processes reported in the scientific literature. The reader is further referred to Advanced Organic Chemistry, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, published by John Wiley and Sons, 1991) and as described hereinabove.

Example 1

General Synthetic Routes for the Preparation of the Compound of Formula I

The compounds of Formula I, their tautomers, polymorphs, stereoisomers, prodrugs, solvates, pharmaceutically acceptable salts, may be prepared following independent general synthetic routes as outlined in the Schemes below:

Scheme 1

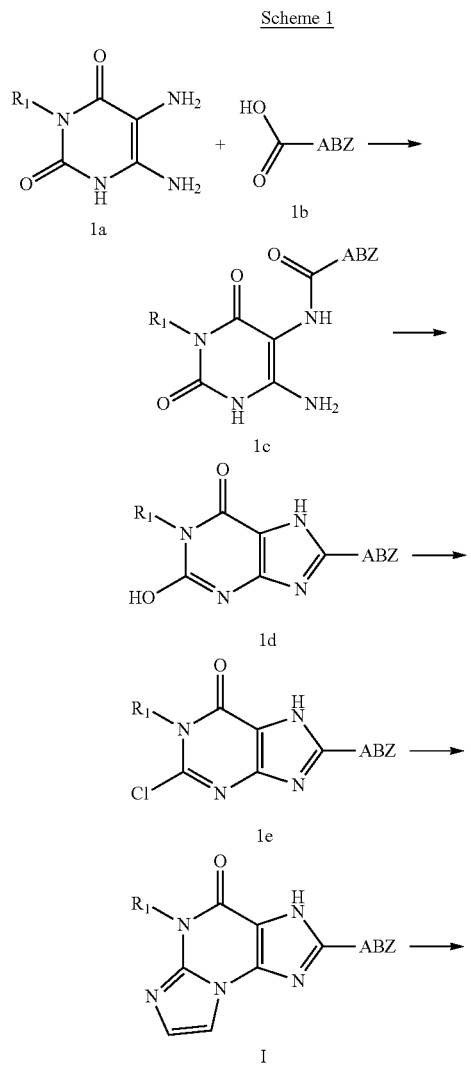

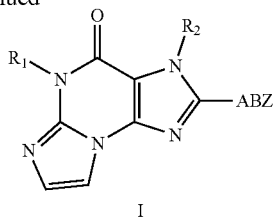

The compound of formula (1a) wherein all symbols are defined herein above, is either available commercially or may be prepared by methods well known in the art (US20080194593, Synthesis 1993, 125-128). The compound of formula (1c) can be prepared from (1a) by reaction with (1b) in presence of carbodimide, for example EDCI.HCl. Subsequently ring is closed with dehydrating reagents such as $P_2O_5$, NaOH to get compound (1d). The compound (1d) converted to (1e) by reaction with chlorinating reagents such as $POCl_3$, $PCl_5$, $SOCl_2$ and the like. The compound of formula (1e) can also be prepared directly by reaction with (1c) in presence of chlorinating reagents such as $POCl_3$, $PCl_5$, $SOCl_2$ and the like.

The compound of formula (1e) may be reacted with aminoacetaldehyde dimethyl acetal in presence of acid such as HCl, $H_2SO_4$, AcOH and the like, to obtain compound of formula (1), which is reacted with $R^2$-L to provide the compound of Formula I.

Scheme 2

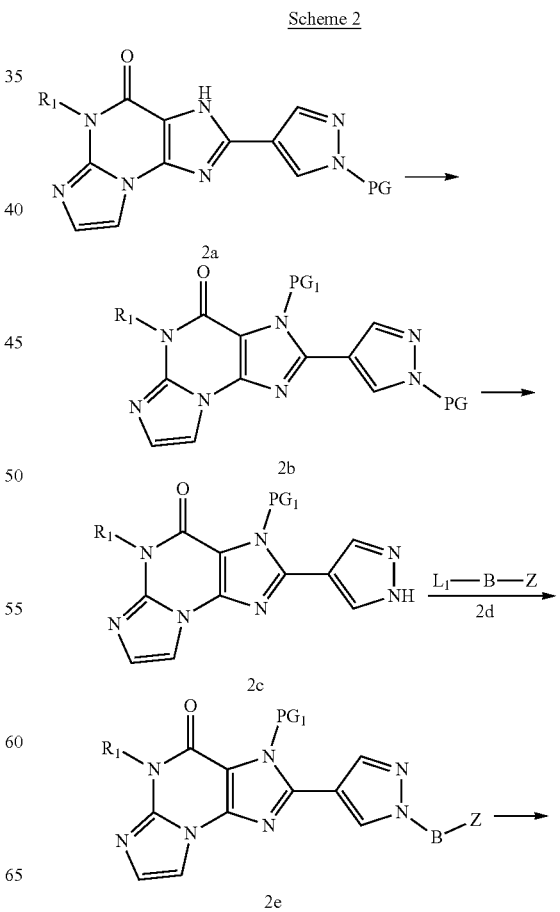

-continued

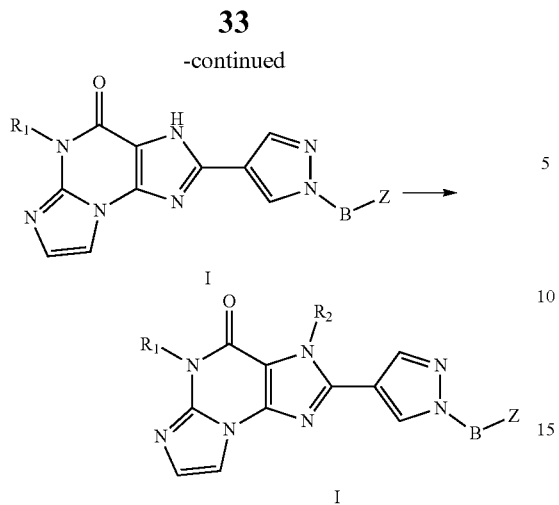

The compound of formula (2a) wherein PG is protecting group, such as benzyl and the like prepared by using scheme 1.

The compound of formula (2b) may be prepared from compound of formula (2a) by protection of —NH wherein PG1 may be SEM, and the like. The compound of formula (2b) can be converted to a formula (2c) by deprotection. The compound of formula (2c) reacted with (2d) where in L1 is leaving group and B and Z are defined above to provide compound of formula (2e) followed by deprotection to provide compound (I). Compounds of Formula I may further be reacted with $R^2$-L to provide compounds of Formula I wherein $R^2$ is other than hydrogen and is as defined herein above.

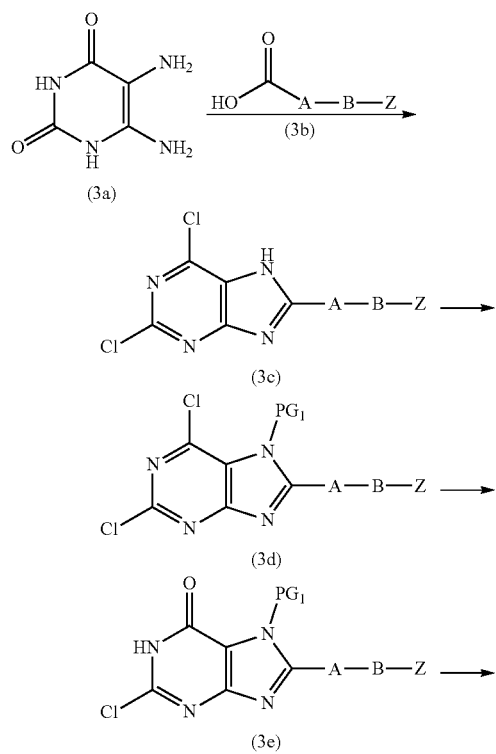

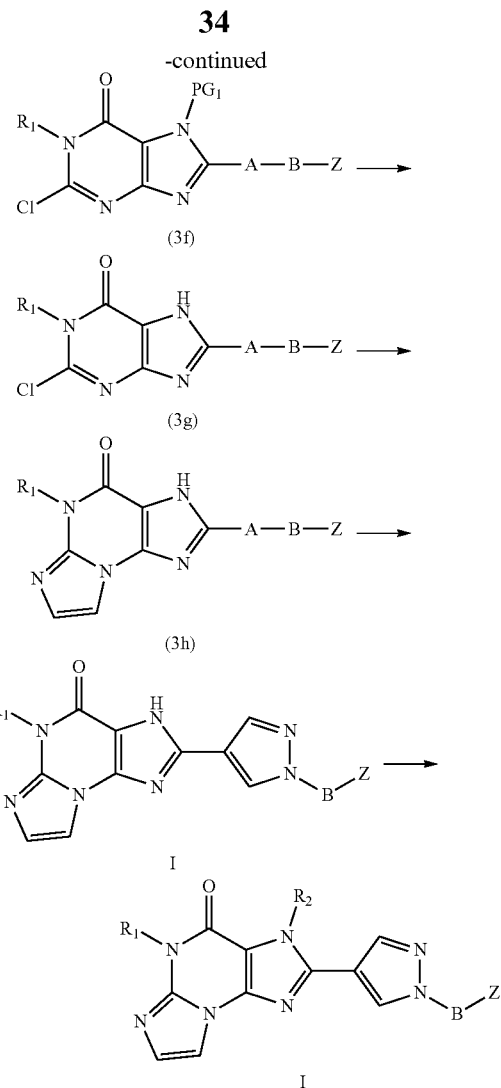

The compound of formula (3a) wherein all symbols are defined herein above is available commercially. Compound (3a) can be reacted with acid (3b) in presence of $POCl_3$ to get compound of formula (3c) which is further reacted with protecting groups to provide compound (3d).

The compound of formula (3d) can be converted to a formula (3e) by hydrolyzing with bases like $K_2CO_3$ or $Na_2CO_3$ or $Cs_2CO_3$ and the like in presence of inert solvents like $CH_3CN$ or EtOH or THF and the like. The compound of formula (3e) can be converted to a formula (3f) by reaction with R1-Hal wherein R1 is defined above and followed by deprotection to provide compound (3g). Then compound (I) can be obtained in a similar way as described above.

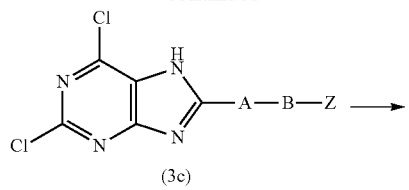

(3c)

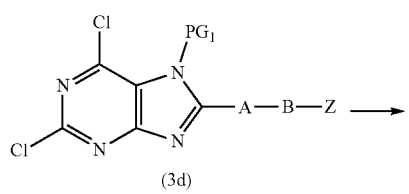

(3d)

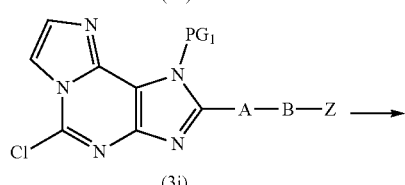

(3i)

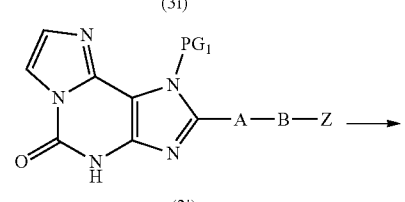

(3j)

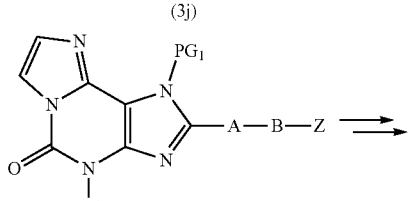

(3k)

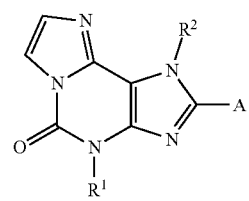

I

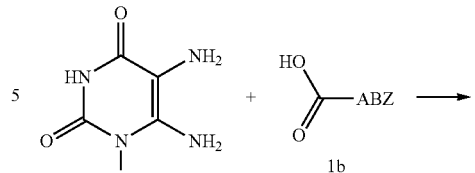

4a

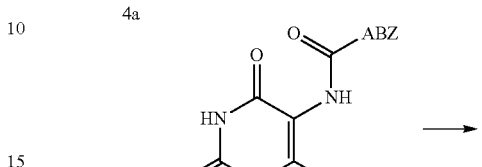

4c

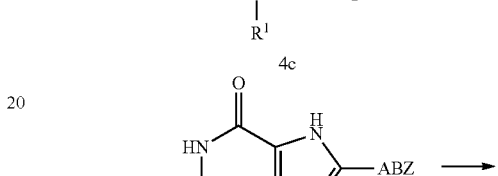

4d

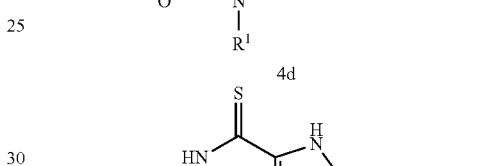

4e

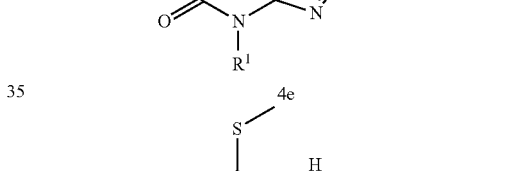

4f

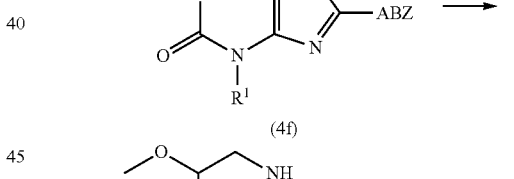

4g

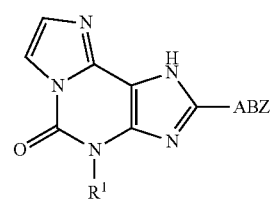

I

The compound of formula (3d) can be obtained in a similar way as described above. The compound of formula (3d) can be converted to a formula (3i) by reaction with aminoacetaldehyde dimethyl acetal in presence of base like Et$_3$N, DIPEA and the like and followed by reaction with acid such as HCl, H$_2$SO$_4$, AcOH and the like. The compound of formula (3i) can be converted to a formula (3j) by hydrolyzing with bases like K$_2$CO$_3$ or Na$_2$CO$_3$ or Cs$_2$CO$_3$ and the like in presence of inert solvents like CH$_3$CN or EtOH or THF and the like. The compound of formula (3j) can also be synthesized from (3i) by reaction with acid such as HCl, H$_2$SO$_4$, AcOH and the like. The compound of formula (3j) can be converted to a formula (3k) by reaction with R1-Hal wherein R1 is defined above and followed by deprotection to provide compound (I).

The compound of formula (4a) wherein all symbols are defined herein above, is either available commercially or may be prepared by methods well known in the art (WO2009157938, US 20130324724). The compound of formula (4d) can be obtained in a similar way as described above. The compound of formula (4e) can be obtained from (4d) by reaction with P₄S₁₀ and followed by alkylation to obtained (4f). The compound of formula (4f) can be converted to a formula (4g) by reaction with aminoacetaldehyde dimethyl acetal in presence of base like Et₃N, DIPEA and the like and followed by reaction with acid such as HCl, H₂SO₄, AcOH and the like to obtain compound of Formula I.

Wherever desired or necessary, in any of the above-mentioned processes, functional groups may be transformed to different functional groups such as an ester function being converted to an acid, amide, hydroxymethyl, keto, aldehyde as well as an ester. The said conversions may be carried out using reagents and conditions well documented in the literature.

Wherever desired or necessary, in any of the above-mentioned processes, any of the compounds of Formula I may be converted into a pharmaceutically acceptable salt or vice versa or converting one salt form into another pharmaceutically acceptable salt form.

Example 2

Example A1: 5-propyl-2-[1-[[3-(trifluoromethyl)phenyl]methyl]pyrazol-4-yl]-3H-imidazo[2,1-b]purin-4-one

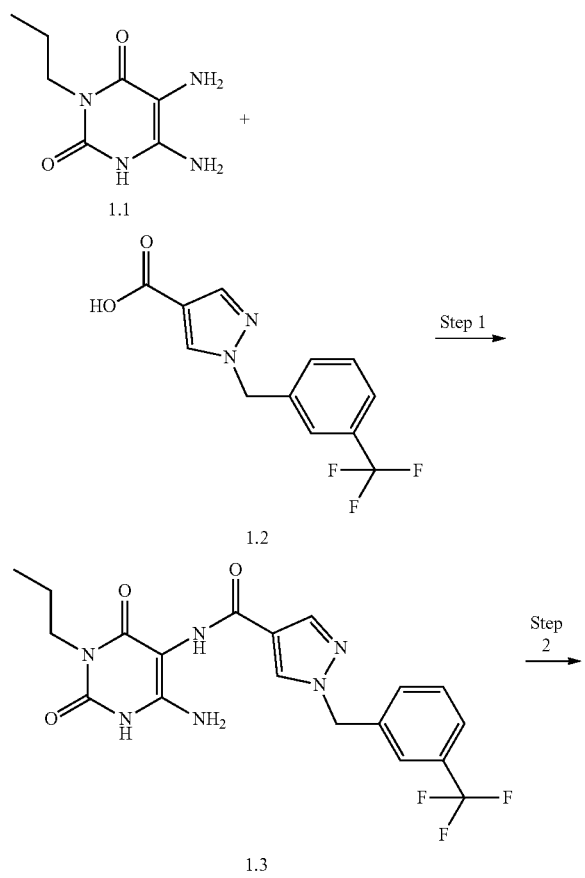

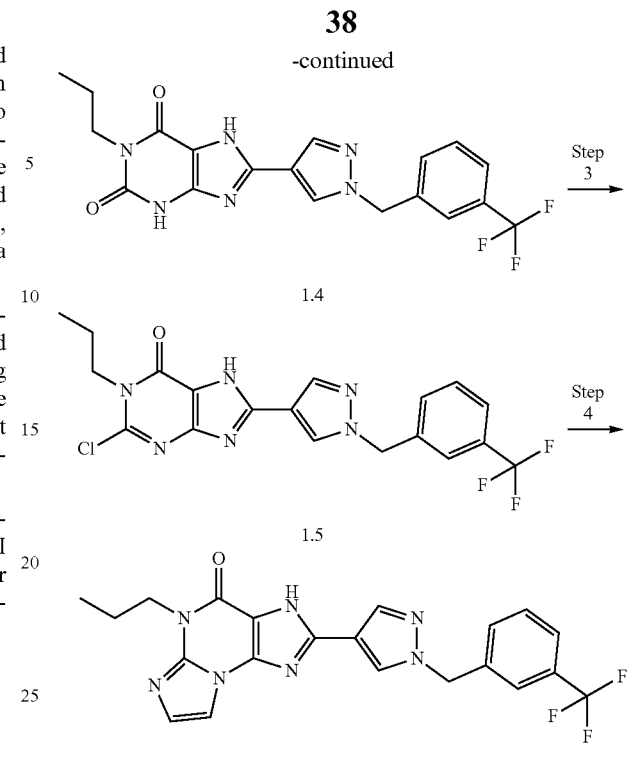

Step 1: Synthesis of N-(6-amino-2,4-dioxo-3-propyl-H-pyrimidin-5-yl)-1-[[3-(trifluoromethyl)phenyl]methyl]pyrazole-4-carboxamide A mixture of 1.1 (30 g, 163.04 mmol), 1.2 (44.0 g, 163.04 mmol) in methanol (1500 mL) were cooled to 0° C. and added EDCI.HCl (37.5 g, 195.65 mmol). The reaction mixture was stirred at 25° C. for 16 hours. Reaction completion was confirmed by TLC, and the organic volatiles were evaporated. To this residue water (2000 mL) was added and the precipitate was filtered off, and washed with cold water (500 mL), washed with n-hexane dried to obtain 1.3 as a pale yellow solid. (60.0 g, 84%).

ESI-MS (m/z): 437.2 (M+1); ¹H NMR (400 MHz, DMSO-d₆): δ 0.82 (t, J=7.6 Hz, 3H); 1.46-1.51 (m, 2H); 3.64 (t, J=7.6 Hz, 2H); 5.49 (s, 2H); 6.01 (s, 2H); 7.55-7.68 (m, 2H); 7.68-7.70 (m, 2H); 7.99 (s, 1H); 8.37 (s, 1H); 8.55 (s, 1H); 10.42 (s, 1H).

Step 2: Synthesis of 1-propyl-8-[1-[[3-(trifluoromethyl)phenyl]methyl]pyrazol-4-yl]-3,7-dihydropurine-2,6-dione In a mixture of 1.3 (60 g, 137.6 mmol) and DMF (600 mL), added P₂O₅ (68.4 g, 481.6 mmol) portion wise and heated at 100° C. for 30 minutes. Reaction completion was confirmed by TLC, and mixture was cooled to 20-25° C. The reaction mixture was slowly poured into water (2.5 L) with vigorous stirring. Solid material separated was filtered off, and washed with cold water (500 mL), washed with n-hexane dried to obtain 1.4 as a pale yellow solid (53 g, 93%).

ESI-MS (m/z): 419.2 (M+1); ¹H NMR (400 MHz, DMSO-d₆): δ 0.87 (t, J=7.2 Hz, 3H); 1.53-1.60 (m, 2H); 3.98 (t, J=7.2 Hz, 2H); 5.53 (s, 2H); 7.57-7.64 (m, 2H); 7.69-7.71 (m, 2H); 8.08 (s, 1H); 8.47 (s, 1H); 11.83 (s, 1H); 13.39 (br s, 1H).

Step 3: Synthesis of 2-chloro-1-propyl-8-[1-[[3-(trifluoromethyl)phenyl]methyl]pyrazol-4-yl]-7H-purin-6-one A mixture of 1.4 (35 g, 83.93 mmol), NH₄Cl (44.8 g, 83.7 mmol) and POCl₃ (1000 mL) were heated at 120-125° C. for 72 h. Reaction completion was confirmed by TLC, mixture was cooled to 20-25° C. It was then concentrated under vacuo and quenched with cold water slowly and solid material was separated. It was filtered off and washed with cold water, dried under vacuo. The crude product was purified by column chromatography using silica gel (230-400 mesh) and 0.5 to 4% methanol in chloroform as an eluent to obtain 1.5 as a pale yellow solid. (17 g, 47%)

ESI-MS (m/z): 437.1 (M+1); ¹H NMR (400 MHz, CD₃OD): δ 1.02 (t, J=7.2 Hz, 3H); 1.72-1.84 (m, 2H); 4.29 (t, J=7.6 Hz, 2H); 5.52 (s, 2H); 7.56-7.57 (m, 2H); 7.61-7.63 (m, 2H); 8.12 (s, 1H); 8.35 (s, 1H)

Step 4: Synthesis of 5-propyl-2-[1-[[3-(trifluoromethyl)phenyl]methyl]pyrazol-4-yl]-3H-imidazo[2,1-b]purin-4-one To a solution of 1.5 (0.2 g, 0.46 mmol) in NMP (5 mL) was added DIPEA (0.30 mL, 1.83 mmol), and aminoacetaldehyde dimethyl acetal (0.20 mL, 1.83 mmol). The mixture was stirred at 130° C. for 3 days. Reaction completion was confirmed by TLC, then cooled to room temperature and residue was dissolved in water (50 mL), and the mixture was extracted with ethyl acetate (3×20 mL). The combined organic layer was washed with brine (20 mL), dried over Na₂SO₄ and concentrated under vacuo to obtain a crude product. It was purified by combiflash column chromatography using 2-5% methanol in DCM as a mobile phase to obtain the title compound A1 as a white solid (0.075 g, 37%).

MS(ESI) m/z: 442.2 (M+1); ¹H NMR (400 MHz, DMSO-d₆): δ 0.90 (t, J=7.2 Hz, 3H); 1.71-1.74 (m, 2H); 4.13-4.16 (m, 2H); 5.52 (s, 2H); 7.15 (d, J=1.2 Hz, 1H); 7.59-7.69 (m, 5H); 8.16 (s, 1H); 8.55 (s, 1H); 13.80 (br s, 1H).

Following examples as shown in Table were prepared according to similar sequence of procedures as used for the synthesis of Example A1

| Ex.No. | Structure | IUPAC Name<br>¹H NMR (400 MHz) data | MS(ESI)<br>m/z: (M + 1) |
|---|---|---|---|
| A2 | 2-(1-benzylpyrazol-4-yl)-5-propyl-3H-imidazo[2,1-b]purin-4-one | DMSO-d₆: δ 0.92 (t, J = 7.2 Hz, 3H); 1.71-1.76 (m, 2H); 4.17 (t, J = 7.2 Hz, 2H); 5.42 (s, 2H); 7.16 (d, J = 1.6 Hz, 1H); 7.31-7.34 (m, 3H); 7.36-7.38 (m, 2H); 7.68 (d, J = 1.2 Hz, 1H); 8.15 (s, 1H); 8.49 (s, 1H); 13.86 (br s, 1H). | 374.2 |
| A3 | 5-methyl-2-[1-[[3-(trifluoromethyl)phenyl]methyl]pyrazol-4-yl]-3H-imidazo[2,1-b]purin-4-one | DMSO-d₆: δ 3.58 (s, 3H); 5.53 (s, 2H); 7.13 (d, J = 1.6 Hz, 1H); 7.60-7.65 (m, 3H); 7.69-7.71 (m, 2H); 8.11 (s, 1H); 8.50 (s, 1H) | 414.1 |
| A4 | 5-propyl-2-[1-[2-[3-(trifluoromethyl)phenyl]ethyl]pyrazol-4-yl]-3H-imidazo[2,1-b]purin-4-one | DMSO-d₆: δ 0.92 (t, J = 7.2 Hz, 3H); 1.71-1.77 (m, 2H); 3.24-3.26 (m, 2H); 4.15-4.19 (m, 2H); 4.48 (t, J = 7.2 Hz, 2H); 7.16 (s, 1H); 7.46-7.57 (m, 4H); 7.663-7.666 (m, 1H); 8.14 (s, 1H); 8.30 (s, 1H); 13.83 (br s, 1H). | 456.2 |

| Ex.No. | Structure | IUPAC Name<br>¹H NMR (400 MHz) data | MS(ESI)<br>m/z: (M + 1) |
|---|---|---|---|
| A5 | 2-[1-[2-(3-fluorophenyl)ethyl]pyrazol-4-yl]-5-propyl-3H-imidazo[2,1-b]purin-4-one | DMSO-d₆: δ 0.92 (t, J = 8.0 Hz, 3H); 1.71-1.77 (m, 2H); 3.17 (t, J = 7.2 Hz, 2H); 4.17 (t, J = 8.0 Hz, 2H); 4.46 (t, J = 7.2 Hz, 2H); 6.99-7.02 (m, 2H); 7.04-7.07 (m, 1H); 7.16 (d, J = 1.2 Hz, 1H); 7.27-7.33 (m, 1H); 7.66 (d, J = 1.6 Hz, 1H); 8.13 (s, 1H); 8.30 (s, 1H); 13.83 (br s, 1H). | 406.2 |
| A6 | 2-(1-methylpyrazol-4-yl)-5-propyl-3H-imidazo[2,1-b] purin-4-one | DMSO-d₆: δ 0.92 (t, J = 8.0 Hz, 3H); 1.74-1.76 (m, 2H); 3.92 (s, 3H); 4.18 (t, J = 7.2 Hz, 2H); 7.17 (s, 1H); 7.68 (s, 1H); 8.09 (s, 1H); 8.37 (s, 1H); 13.85 (s, 1H). | 298.2 |
| A7 | 2-[1-(1,1-dimethylpropyl)pyrazol-4-yl]-5-propyl-3H-imidazo[2,1-b]purin-4-one | DMSO-d₆: δ 0.64 (t, J = 7.6 Hz, 3H); 0.92 (t, J = 7.6 Hz, 3H); 1.55 (s, 6H); 1.72-1.78 (m, 2H); 1.84-1.90 (m, 2H); 4.17 (t, J = 7.6 Hz, 2H); 7.16 (d, J = 1.6 Hz, 1H); 7.68 (d, J = 1.6 Hz, 1H); 8.13 (s, 1H); 8.46 (s, 1H); 12.83 (br s, 1H). | 354.3 |

Example B1: N-isopropyl-3-[3-[4-(4-oxo-5-propyl-3H-imidazo[2,1-b]purin-2-yl)pyrazol-1-yl]prop-1-ynyl]benzamide

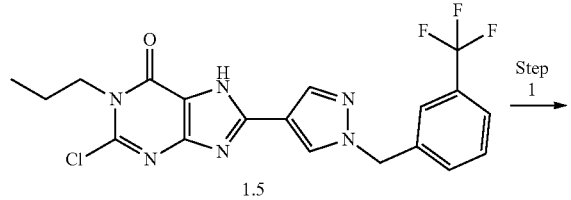

1.5

→ Step 1 →

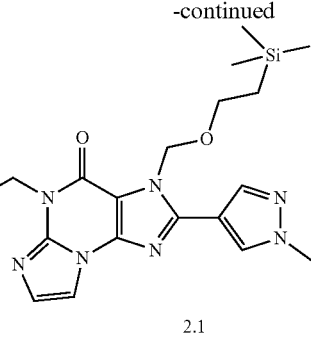

2.1

→ Step 3 →

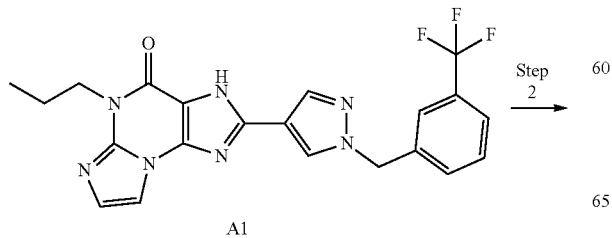

A1

→ Step 2 →

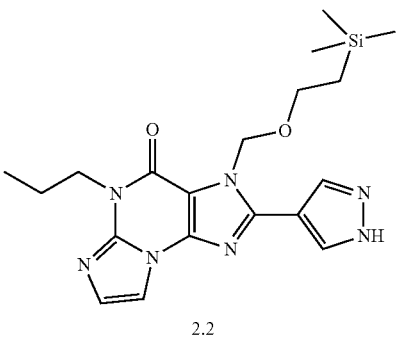

2.2

+

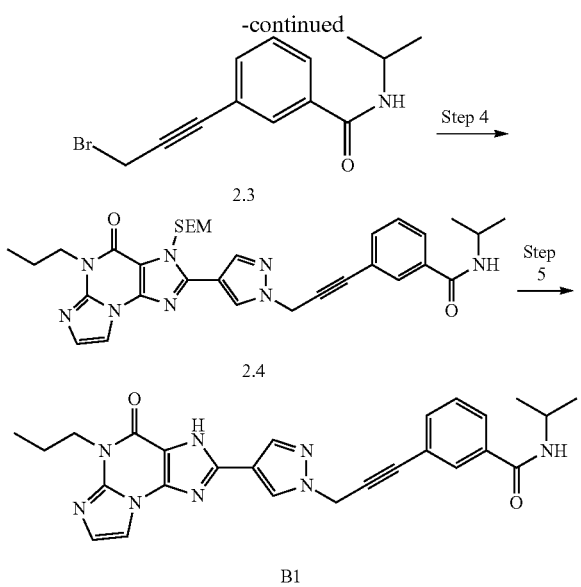

Step 1: Synthesis of 5-propyl-2-[1-[[3-(trifluoromethyl)phenyl]methyl]pyrazol-4-yl]-3H-imidazo[2,1-b]purin-4-one To a solution of 1.5 (9.0 g, 20.64 mmol) in NMP (45 mL) was added DIPEA (3.4 mL, 20.64 mmol), and aminoacetaldehyde dimethyl acetal (8.9 mL, 82.56 mmol). The mixture was stirred at 130° C. for 6 hours then reaction mixture was cooled to room temperature then added conc. HCl (27 mL) and stirred at 130° C. for 16 hours. Reaction completion was confirmed by TLC then cooled to room temperature and residue was dissolved in water (500 mL), and the mixture was extracted with ethyl acetate (3×200 mL). The combined organic layers were washed with brine (200 mL), dried over $Na_2SO_4$ and concentrated under vacuo to obtain a crude product. To the residue added cold methanol solid obtained was filtered and washed with n-hexane and dried to obtain A1 as a white solid (6.0 g, 66%).

MS(ESI) m/z: 442.2 (M+1); $^1$H NMR (400 MHz, DMSO-$d_6$): δ 0.90 (t, J=7.2 Hz, 3H); 1.71-1.74 (m, 2H); 4.13-4.16 (m, 2H); 5.52 (s, 2H); 7.15 (d, J=1.2 Hz, 1H); 7.59-7.69 (m, 5H); 8.16 (s, 1H); 8.55 (s, 1H); 13.80 (br s, 1H).

Step 2: Synthesis of 5-propyl-2-[1-[[3-(trifluoromethyl)phenyl]methyl]pyrazol-4-yl]-3-(2 trimethylsilylethoxymethyl)imidazo[2,1-b]purin-4-one To a solution of A1 (5.0 g, 11.33 mmol) in DMF (50 mL) was added $K_2CO_3$ (7.8 g, 56.70 mmol), and 2-(chloromethoxy)ethyl-trimethyl-silane (20 mL, 113.37 mmol). The mixture was stirred at room temperature for 2 days. Reaction completion was confirmed by TLC then dissolved in water (500 mL), and the mixture was extracted with ethyl acetate (3×200 mL). The combined organic layers were washed with brine (200 mL), dried over $Na_2SO_4$ and concentrated under vacuo to obtain a crude product. The residue was purified by column chromatography using 30-35% ethyl acetate in hexane as a mobile phase to obtain the title compound 2.1 as a white solid (6.0 g, 93%).

MS(ESI) m/z: 572.0 (M+1); $^1$H NMR (400 MHz, DMSO-$d_6$): δ −0.13 (s, 9H), 0.83-0.92 (m, 5H); 1.71-1.77 (m, 2H); 3.67-3.71 (m, 2H); 4.18 (t, J=6.8 Hz, 2H); 5.58 (s, 2H); 5.94 (s, 2H); 7.18 (d, J=1.6 Hz, 1H); 7.33-7.37 (m, 1H); 7.61-7.63 (m, 1H); 7.68-7.71 (m, 3H); 8.11 (s, 1H); 8.60 (s, 1H).

Step 3: Synthesis of 5-propyl-2-(1H-pyrazol-4-yl)-3-(2-trimethylsilylethoxymethyl)imidazo[2,1-b]purin-4-one To a solution of 2.1 (1.6 g, 2.84 mmol) in THF (2 mL) was added potassium tert butoxide (2.55 g, 22.76 mmol), and DMSO (2.3 g, 22.76 mmol). The mixture was cooled to ° C. and Oxygen was bubbled for 30 minutes. Reaction completion was confirmed by TLC then quenched with aqueous saturated solution of ammonium chloride (4 mL) at 0° C. extracted with ethyl acetate (150 mL), washed with water (30 mL), brine (30 mL), dried over $Na_2SO_4$ and concentrated under vacuo to obtain 2.2 as an Off white solid (1.1 g, 94%).

MS(ESI) m/z: 414.3; $^1$H NMR (400 MHz, DMSO-$d_6$): δ −0.087 (s, 9H), 0.86-0.93 (m, 5H); 1.72-1.78 (m, 2H); 3.70-3.74 (m, 2H); 4.19 (t, J=7.2 Hz, 2H); 5.94 (s, 2H); 7.19 (d, J=1.6 Hz, 1H); 7.74 (d, J=1.6 Hz, 1H); 8.10 (s, 1H); 8.39 (s, 1H); 13.52 (br s, 1H).

Step 4: Synthesis of N-isopropyl-3-[3-[4-[4-oxo-5-propyl-3-(2-trimethylsilylethoxymethyl)imidazo[2,1-b]purin-2-yl]pyrazol-1-yl]prop-1-ynyl]benzamide (2.4)

Synthesis of 3-iodo-N-isopropyl-benzamide

A mixture of 3-iodobenzoic acid (3.0 g, 12.09 mmol), isopropyl amine (1.2 mL, 14.51 mmol) in DMF (30 mL) were cooled to 0° C. and added EDCI.HCl (3.25 g, 16.93 mmol). The reaction mixture was stirred at 25° C. for 16 hours. Reaction completion was confirmed by TLC, residue was dissolved in water (150 mL), and the mixture was extracted with ethyl acetate (3×50 mL). The combined organic layers were washed with brine (50 mL), dried over $Na_2SO_4$ and concentrated under vacuo to obtain a crude product. The residue was purified by combiflash column chromatography using 10-15% ethyl acetate in hexane as a mobile phase to obtain the title compound 3-iodo-N-isopropyl-benzamide as white solid (1.0 g, 28%).

MS(ESI) m/z: 289.9 (M+1); $^1$H NMR (400 MHz, DMSO-$d_6$): δ 1.15 (d, J=6.4 Hz, 6H); 4.05-4.10 (m, 1H); 7.26 (d, J=8.0 Hz, 1H); 7.83-7.88 (m, 2H); 8.18 (d, J=2.0 Hz, 1H); 8.29-8.32 (m, 1H).

Synthesis of 3-(3-hydroxyprop-1-ynyl)-N-isopropyl-benzamide

A mixture of propargyl alcohol (0.26 mL, 4.15 mmol), 3-iodo-N-isopropyl-benzamide (1.0 g, 3.46 mmol), copper iodide (0.02 g, 0.1 mmol), dichlorobis (triphenylphosphine) palladium (II) (0.12 g, 0.17 mmol), 1,4-dioxane:triethylamine (1:1) (20 ml) was degassed for 10 min. and stirred for 2 hours at 60° C. Reaction completion was confirmed by TLC, residue was concentrated under vacuo to obtain a crude product. The residue was purified by combiflash column chromatography using 15-20% ethyl acetate in hexane as a mobile phase to obtain the title compound 3-(3-hydroxyprop-1-ynyl)-N-isopropyl-benzamide as white solid (0.5 g, 67%).

MS(ESI) m/z: 218.0 (M+1); $^1$H NMR (400 MHz, DMSO-$d_6$): δ 1.00 (d, J=6.4 Hz, 6H); 4.02-4.04 (m, 1H); 4.33 (d,

J=5.6 Hz, 2H); 5.36 (t, J=5.6 Hz, 1H); 7.46 (t, J=7.6 Hz, 1H); 5.54-7.55 (m, 1H); 7.83 (d, J=7.6 Hz, 1H); 7.92 (s, 1H); 8.30-8.40 (m, 1H).

Synthesis of 3-(3-bromoprop-1-ynyl)-N-isopropyl-benzamide

A mixture of 3-(3-hydroxyprop-1-ynyl)-N-isopropyl-benzamide (0.5 g, 2.30 mmol), and DCM (10 mL) was cooled to 0° C. added tribromo phosphine (0.11 mL, 1.15 mmol) slowly and stirred at room temperature for 1 hour. Reaction completion was confirmed by TLC, reaction mixture was quenched with saturated NaHCO$_3$ solution and extracted with DCM (3×15 mL), washed with saturated brine solution, dried over Na$_2$SO$_4$, and evaporated under vacuo to obtain 3-(3-bromoprop-1-ynyl)-N-isopropyl-benzamide as a white solid (2.3) (0.55 g, 86%).

MS(ESI) m/z: 279.9 & 282.9 (M+1); $^1$H NMR (400 MHz, DMSO-d$_6$): δ 1.27 (d, J=6.4 Hz, 6H); 4.16 (s, 2H); 4.25-4.29 (m, 1H); 5.88 (br s, 1H); 7.39 (t, J=8.0 Hz, 1H); 7.53-7.55 (m, 1H); 7.74-7.78 (m, 2H).

Synthesis of N-isopropyl-3-[3-[4-[4-oxo-5-propyl-3-(2-trimethylsilylethoxymethyl)imidazo[2,1-b]purin-2-yl]pyrazol-1-yl]prop-1-ynyl]benzamide (2.4)

To a solution 2.2 (0.1 g, 0.24 mmol) in acetone (10 mL) was added potassium carbonate (0.05 g, 0.36 mmol), and 2.3 (0.081 g, 0.29 mmol). The mixture was stirred at 60° C. for 2 days. Reaction completion was confirmed by TLC then cooled to room temperature and filtered through celite pad, washed with acetone (15 mL) and concentrated under vacuo to obtain a crude product. The residue was purified by combiflash column chromatography using 2-5% methanol in DCM as a mobile phase to give the title compound 2.4 as a white solid (0.14 g, 95%).

MS(ESI) m/z: 613.0 (M+1); $^1$H NMR (400 MHz, DMSO-d$_6$): δ −0.099 (s, 9H), 0.83-0.95 (m, 5H); 1.12-1.16 (m, 6H); 1.72-1.78 (m, 2H); 3.72 (t, J=8.4 Hz, 2H); 4.05-4.10 (m, 1H); 4.20 (t, J=6.8 Hz, 2H); 5.49 (s, 2H); 5.95 (s, 2H); 7.20 (d, J=1.6 Hz, 1H); 7.46-7.50 (m, 1H); 7.60-7.62 (m, 1H); 7.75 (d, J=1.6 Hz, 1H); 7.76-7.89 (m, 1H); 7.96 (d, J=1.6 Hz, 1H); 8.15 (s, 1H); 8.33 (d, J=7.2 Hz, 1H); 8.58 (s, 1H).

Step 5: Synthesis of N-isopropyl-3-[3-[4-(4-oxo-5-propyl-3H-imidazo[2,1-b]purin-2-yl)pyrazol-1-yl]prop-1-ynyl]benzamide A solution of 2.4 (0.14 g, 0.23 mmol) in ethanol, 2N HCl (10 mL) was heated at 80° C. for 8 hours. Reaction completion was confirmed by TLC then cooled to room temperature and concentrated under vacuo to obtain a crude product. The residue was basified by aqueous NaHCO$_3$ solution up to PH (7-8) then solid obtained was filtered, washed with n-hexane, dried and purified by combiflash column chromatography using 2-5% methanol in DCM as a mobile phase to give the title compound B1 as a white solid (0.060 g, 54%).

MS(ESI) m/z: 483.3 (M+1); $^1$H NMR (400 MHz, DMSO-d$_6$): δ 0.92 (t, J=7.2 Hz, 3H); (1.15 (d, J=6.4 Hz, 6H), 1.72-1.78 (m, 2H); 4.05-4.11 (m, 1H); 4.18 (t, J=7.6 Hz, 2H); 5.45 (s, 2H); 7.17 (d, J=1.6 Hz, 1H); 7.47-7.52 (m, 1H); 7.64 (d, J=7.6 Hz, 1H); 7.71 (d, J=1.6 Hz, 1H); 7.88 (d, J=8.0 Hz, 1H); 7.97 (br s, 1H); 8.19 (s, 1H); 8.34 (d, J=7.6 Hz, 1H); 8.60 (s, 1H); 13.95 (br s, 1H).

Following examples as shown in Table were prepared according to similar sequence of procedures as used for the synthesis of Example B1

| Ex. No. | Structure IUPAC Name | $^1$H NMR(400 MHz) data | MS(ESI) m/z: (M + 1) |
|---|---|---|---|
| B2 | Ethyl 3-[3-[4-(4-oxo-5-propyl-3H-imidazo[2,1-b]purin-2-yl)pyrazol-1-yl]prop-1-ynyl]benzoate | DMSO-d$_6$: δ 0.92 (t, J = 7.6 Hz, 3H); 1.32 (t, J = 7.2 Hz, 3H); 1.72-1.78 (m, 2H); 4.18 (t, J = 7.6 Hz, 2H); 4.33 (t, J = 6.8 Hz, 2H); 5.45 (s, 2H); 7.17 (d, J = 1.6 Hz, 1H); 7.58 (dd, J = 7.6, 8.0 Hz, 1H); 7.71 (d, J = 1.2 Hz, 1H); 7.78 (d, J = 7.6 Hz, 1H); 7.98-8.01 (m, 2H); 8.19 (s, 1H); 8.61 (s, 1H); 13.98 (br s, 1H) | 470.2 |
| B3 | 5-propyl-2-[1-[3-[3-(trifluoromethoxy)phenyl]prop-2-ynyl]pyrazol-4-yl]-3H-imidazo[2,1-b]purin-4-one | DMSO-d$_6$: δ 0.92 (t, J = 7.6 Hz, 3H); 1.72-1.78 (m, 2H); 4.18 (t, J = 7.2 Hz, 2H); 5.45 (s, 2H); 7.17 (d, J = 1.6 Hz, 1H); 7.46 (br s, 1H); 7.51 (br s, 1H); 7.55-7.56 (m, 2H); 7.70 (d, J = 1.6 Hz, 1H); 8.19 (s, 1H); 8.59 (s, 1H); 13.95 (br s, 1H) | 482.2 |
| B6 | | DMSO-d$_6$: δ.92 (t, J = 7.2 Hz, 3H); 1.31 (t, J = 7.2 Hz, 3H); 1.72-1.78 (m, 2H); 2.32 (s, 3H); 4.18 (t, J = 7.6 Hz, 2H); 4.30 (t, J = 6.8 Hz, 2H); 5.48 (s, 2H); 7.17 (d, J = 1.6 Hz, 1H); 7.48 (d, J = 7.6 Hz, 1H); 7.70 (d, J = 1.6 Hz, 1H); 7.88 (dd, J = 2.0, 8.0 Hz, 1H); 7.96 (d, J = 1.6 Hz, 1H); 8.19 (s, 1H), 8.61 (s, 1H); 13.95 (br s, 1H) | 484.2 |

| Ex. No. | Structure IUPAC Name | ¹H NMR(400 MHz) data | MS(ESI) m/z: (M + 1) |
|---|---|---|---|
| | Ethyl 4-methyl-3-[3-[4-(4-oxo-5-propyl-3H-imidazo[2,1-b]purin-2-yl)pyrazol-1-yl]prop-1-ynyl]benzoate | | |
| B7 | 3-[[4-(4-oxo-5-propyl-3H-imidazo[2,1-b]purin-2-yl)pyrazol-1-yl]methyl]benzonitrile | DMSO-$d_6$: δ 0.92 (t, J = 7.2 Hz, 3H); 1.70-1.76 (m, 2H); 4.17 (t, J = 6.8 Hz, 2H); 5.50 (s, 2H); 7.22 (s, 1H); 7.60-7.63 (m, 2H); 7.72 (s, 1H); 7.81 (s, 2H); 8.18 (s, 1H); 8.56 (s, 1H); 13.91 (br s, 1H). | 399.2 |
| B8 | 2-(1-isopropylpyrazol-4-yl)-5-propyl-3H-imidazo[2,1-b]purin-4-one | DMSO-$d_6$: δ 0.92 (t, J = 7.6 Hz, 3H); 1.46 (d, J = 6.8 Hz, 6H); 1.72-1.78 (m, 2H); 4.17 (t, J = 7.6 Hz, 2H); 4.58 (m, 1H); 7.17 (d, J = 1.6 Hz, 1H); 7.67 (d, J = 1.6 Hz, 1H); 8.12 (s, 1H); 8.45 (s, 1H); 13.92 (br s, 1H) | 326.2 |
| B9 | 2-(1-butylpyrazol-4-yl)-5-propyl-3H-imidazo[2,1-b]purin-4-one | DMSO-$d_6$: δ 0.88-0.94 (m, 5H); 1.23-1.29 (m, 3H); 1.74-1.80 (m, 4H); 4.15-4.20 (m, 4H); 7.16 (d, J = 1.6 Hz, 1H); 7.67 (s, 1H); 8.10 (s, 1H); 8.40 (s, 1H); 13.86 (br s, 1H) | 340.2 |
| B10 | 2-(1-ethylpyrazol-4-yl)-5-propyl-3H-imidazo[2,1-b]purin-4-one | DMSO-$d_6$: δ 0.94 (t, J = 7.2 Hz, 3H); 1.42 (t, J = 7.2 Hz, 3H); 1.71-1.77 (m, 2H); 4.15-4.25 (m, 4H); 7.34 (br s, 1H); 7.79 (br s, 1H); 8.12 (d, J = 0.8 Hz, 1H); 8.43 (s, 1H); 13.95 (br s, 1H). | 312.2 |
| B11 | 2-[1-(2-methoxyethyl)pyrazol-4-yl]-5-propyl-3H-imidazo[2,1-b]purin-4-one | DMSO-$d_6$: δ 0.94 (t, J = 7.6 Hz, 3H); 1.72-1.77 (m, 2H); 3.26 (s, 3H); 3.72 (t, J = 4.8 Hz, 2H); 4.18 (t, J = 7.2 Hz, 2H); 4.36 (t, J = 4.8 Hz, 2H); 7.33 (br s, 1H); 7.81 (s, 1H); 8.13 (s, 1H); 8.41 (s, 1H); 13.99 (s, 1H) | 342.2 |

| Ex. No. | Structure IUPAC Name | ¹H NMR(400 MHz) data | MS(ESI) m/z: (M + 1) |
|---|---|---|---|
| B12 | 2-[1-(2-dimethylaminoethyl)pyrazol-4-yl]-5-propyl-3H-imidazo[2,1-b]purin-4-one | DMSO-d$_6$: δ 0.96 (t, J = 7.2 Hz, 3H); 1.71-1.77 (m, 2H); 2.76 (s, 3H); 2.78 (s, 3H); 3.59-3.63 (m, 2H); 4.21 (t, J = 8.0 Hz, 2H); 4.72 (t, J = 6.4 Hz, 2H); 7.56 (s, 1H); 7.94 (d, J = 1.6 Hz, 1H); 8.26 (s, 1H); 8.58 (s, 1H); 14.32 (br s, 1H) | 355.3 |
| B13 | 5-propyl-2-(1-propylpyrazol-4-yl)-3H-imidazo[2,1-b]purin-4-one | DMSO-d$_6$: δ 0.85 (t, J = 7.6 Hz, 3H); 0.92 (t, J = 7.2 Hz, 3H); 1.74-1.78 (m, 2H); 1.80-1.84 (m, 2H); 4.13-4.20 (m, 4H); 7.17 (d, J = 1.6 Hz, 1H); 7.68 (d, J = 0.8 Hz, 1H); 8.13 (s, 1H); 8.41 (s, 1H); 13.84 (br s, 1H). | 326.2 |
| B14 | N,N-dimethyl-2-[4-(4-oxo-5-propyl-3H-imidazo[2,1-b]purin-2-yl)pyrazol-1-yl]acetamide | DMSO-d$_6$: δ 0.93 (t, J = 7.6 Hz, 3H); 1.75 (q, J = 7.2 Hz, 2H); 2.87 (s, 3H); 3.05 (s, 3H); 4.18 (t, J = 7.2 Hz, 2H); 5.22 (s, 2H); 7.17 (d, J = 1.6 Hz, 1H); 7.06 (d, J = 1.6 Hz, 1H); 8.10 (s, 1H); 8.33 (s, 1H); 13.90 (br s, 1H). | 369.0 |
| B15 | 2-[1-(2-morpholinoethyl)pyrazol-4-yl]-5-propyl-3H-imidazo[2,1-b]purin-4-one | DMSO-d$_6$: δ 0.97 (t, J = 7.2 Hz, 3H); 1.71-1.76 (m, 2H); 3.13-3.16 (m, 2H); 3.36-3.39 (m, 2H); 3.64-3.67 (m, 2H); 3.80-3.86 (m, 2H); 3.94-3.96 (m, 2H); 4.23 (t, J = 7.6 Hz, 2H); 4.80 (t, J = 6.8 Hz, 2H); 7.68 (s, 1H); 8.09 (s, 1H); 8.26 (s, 1H); 8.59 (s, 1H); 14.2 (br s, 1H) | 397.2 |
| B16 | 2-[1-(cyclobutylmethyl)pyrazol-4-yl]-5-propyl-3H-imidazo[2,1-b]purin-4-one | DMSO-d$_6$: δ 0.93 (t, J = 7.2 Hz, 3H); 1.71-1.90 (m, 6H); 1.97-2.01 (m, 2H); 2.76-2.82 (m, 1H); 4.15-4.22 (m, 4H); 7.31 (br s, 1H); 7.78 (br s, 1H); 8.11 (s, 1H); 8.40 (s, 1H); 13.95 (br s, 1H). | 352.2 |
| B17 | | DMSO-d$_6$: δ 0.87 (d, J = 6.4 Hz, 6H); 0.91 (t, J = 7.6 Hz, 3H); 1.69-1.75 (m, 2H); 2.10-2.17 (m, 1H); 3.97 (d, J = 6.8 Hz, 2H); 4.14 (t, J = 8.0 Hz, 2H); 7.08 (br s, 1H); 7.57 (br s, 1H); 7.96 (br s, 1H); 8.19 (br s, 1H). | 340.2 |

| Ex. No. | Structure IUPAC Name | ¹H NMR(400 MHz) data | MS(ESI) m/z: (M + 1) |
|---|---|---|---|
| | 2-(1-isobutylpyrazol-4-3/1)-5-propyl-3H-imidazo[2,1-b]purin-4-one | | |
| B18 | 2-[1-(cyclopropylmethyl)pyrazol-4-yl]-5-propyl-3H-imidazo[2,1-b]purin-4-one | DMSO-$d_6$: δ 0.39-0.43 (m, 2H); 0.55-0.60 (m, 2H); 0.92 (t, J = 7.6 Hz, 3H); 1.26-1.30 (m, 1H); 1.72-1.78 (m, 2H); 4.05 (d, J = 7.6 Hz, 2H); 4.18 (t, J = 7.2 Hz, 2H); 7.17 (d, J = 1.6 Hz, 1H); 7.69 (d, J = 1.6 Hz, 1H); 8.12 (s, 1H); 8.48 (s, 1H); 13.80 (br s, 1H). | 338.2 |
| B19 | 2-[1-(2,2-dimethylpropyl)pyrazol-4-yl]-5-propyl-3H-imidazo[2,1-b]purin-4-one | DMSO-$d_6$: δ 0.91-0.94 (m, 12H); 1.72-1.78 (m, 2H); 4.00 (s, 2H); 4.17 (t, J = 7.2 Hz, 2H); 7.25 (br s, 1H); 7.74 (br s, 1H); 8.12 (s, 1H); 8.37 (s, 1H); 13.95 (br s, 1H). | 354.3 |
| B20 | 5-propyl-2-(1-sec-butylpyrazol-4-yl)-3H-imidazo[2,1-b]purin-4-one | DMSO-$d_6$: δ 0.74 (t, J = 7.2 Hz, 3H); 0.92 (t, J = 7.2 Hz, 3H); 1.45 (d, J = 6.4 Hz, 3H); 1.72-1.86 (m, 4H); 4.18 (d, J = 7.6 Hz, 2H); 4.33-4.38 (m, 1H); 7.17 (d, J = 1.6 Hz, 1H); 7.67 (d, J = 1.2 Hz, 1H); 8.14 (s, 1H); 8.44 (s, 1H); 13.90 (br s, 1H). | 340.2 |
| B21 | 5-propyl-2-[1-sec-(tetrahydrofuran-2-ylmethyl)pyrazol-4-yl]-3H-imidazo[2,1-b]purin-4-one | DMSO-$d_6$: δ 0.92 (t, J = 7.2 Hz, 3H); 1.60-1.63 (m, 1H); 1.72-1.81 (m, 4H); 1.93-1.96 (m, 1H); 3.63-3.68 (m, 1H); 3.74-3.79 (m, 1H); 4.16-4.28 (m, 5H); 7.17 (d, J = 2.0 Hz, 1H); 7.69 (d, J = 1.6 Hz, 1H); 8.11 (s, 1H); 8.39 (s, 1H); 13.15 (br s, 1H). | 368.2 |

Example C1: 2-[1-[[5-oxo-1-[2-(trifluoromethyl)-4-pyridyl]pyrrolidin-3-yl]methyl]pyrazol-4-yl]-5-propyl-3H-imidazo[2,1-b]purin-4-one

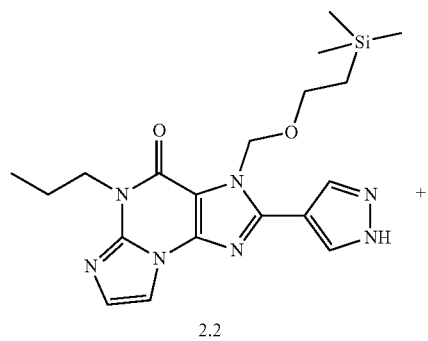

2.2

+

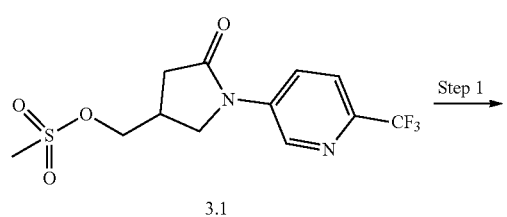

3.1

Step 1 →

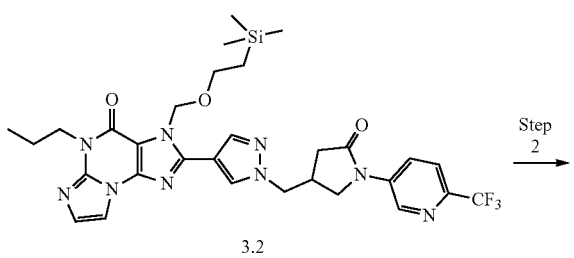

3.2

Step 2 →

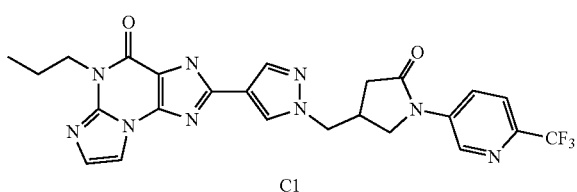

C1

Step 1: 2-[1-[[5-oxo-1-[6-(trifluoromethyl)-3-pyridyl]pyrrolidin-3-yl]methyl]pyrazol-4-yl]-5-propyl-3-(2-trimethylsilylethoxymethyl)imidazo[2,1-b]purin-4-one (3.2)

Synthesis of 5-oxo-1-[2-(trifluoromethyl)-4-pyridyl]pyrrolidine-3-carboxylic Acid A mixture of 2-(trifluoromethyl)pyridin-5-amine (1.12 g, 6.92 mmol) and itaconic acid (1.0 g, 7.69 mmol) was heated at 130-135° C. for 10 hours. Reaction completion was confirmed by TLC then cooled to room temperature, diluted with diethyl ether, solid was filtered off, dried to obtain 5-oxo-1-[6-(trifluoromethyl)-3-pyridyl]pyrrolidine-3-carboxylic acid as a off white solid (0.49 g, 23%).

MS(ESI) m/z: 275.1 (M+1); $^1$H NMR: Not recorded

Synthesis of ethyl 5-oxo-1-[2-(trifluoromethyl)-4-pyridyl]pyrrolidine-3-carboxylate A mixture of 5-oxo-1-[6-(trifluoromethyl)-3-pyridyl]pyrrolidine-3-carboxylic acid (0.4 g, 2.42 mmol), sulfuric acid (0.5 mL), and ethanol (20 mL) was heated at 80-85° C. for 10 hours. Reaction completion was confirmed by TLC and cooled to room temperature. The organic volatiles were evaporated under vacuo to obtain a crude product. The residue dissolved in ethyl acetate (20 mL) and washed with NaHCO$_3$ solution (2×20 mL). Organic layer was washed with brine, dried over Na$_2$SO$_4$ and evaporated under vacuo to obtain ethyl 5-oxo-1-[6-(trifluoromethyl)-3-pyridyl]pyrrolidine-3-carboxylate as yellow oil (0.43 g, 98%).

MS(ESI) m/z: 303.1 (M+1); $^1$H NMR: Not recorded

Synthesis of 4-(hydroxymethyl)-1-[6-(trifluoromethyl)-3-pyridyl]pyrrolidin-2-one A mixture of ethyl 5-oxo-1-[6-(trifluoromethyl)-3-pyridyl]pyrrolidine-3-carboxylate (0.41 g, 1.37 mmol) and methanol (20 mL) were cooled to 10-15° C. and sodium borohydride (0.10 g, 2.74 mmol) was added portion wise over a period of 5 min and the reaction mixture was stirred for 9 hours at room temperature. Reaction completion was confirmed by TLC and concentrated under vacuo to obtain a crude product. To the residue water (20 mL), was added and aqueous solution was extracted with ethyl acetate (3×20 ml). Combined organic layer was washed with brine, dried over Na$_2$SO$_4$ and evaporated to afford crude which was purified by combiflash column chromatography using 40-50% ethyl acetate in hexane as a mobile phase to obtain 4-(hydroxymethyl)-1-[6-(trifluoromethyl)-3-pyridyl]pyrrolidin-2-one as colorless oil (0.31 g, 88%).

MS(ESI) m/z: 261.0 (M+1); $^1$HNMR (400 MHz, DMSO-d6): δ 2.31-2.37 (m, 1H); 2.47-2.68 (m, 1H); 3.14-3.17 (m, 1H); 3.41-3.45 (m, 2H); 3.69-3.73 (m, 1H); 3.98-4.01 (m, 1H); 4.85-4.87 (m, 1H); 8.55 (br s, 1H); 8.70 (s, 1H); 9.06 (d, J=2.0 Hz, 1H)

Synthesis of [5-oxo-1-[6-(trifluoromethyl)-3-pyridyl]pyrrolidin-3-yl]methyl methanesulfonate (3.1)

A mixture of 4-(hydroxymethyl)-1-[6-(trifluoromethyl)-3-pyridyl]pyrrolidin-2-one (0.25 g, 0.96 mmol), dichloromethane (7 mL) and triethyl amine (0.27 mL, 1.92 mmol) was cooled to 0° C. To this solution methane sulfonyl chloride (0.089 mL, 1.15 mmol) was added over a period of 5 min and the reaction mixture was stirred for 2 hours at room temperature. Reaction completion was confirmed by TLC, added aqueous NaHCO$_3$ solution, and extracted by DCM (2×20 ml). Organic layer was washed with brine, dried over Na$_2$SO$_4$ and evaporated to obtain [5-oxo-1-[6-(trifluoromethyl)-3-pyridyl]pyrrolidin-3-yl]methyl methanesulfonate as yellow oil (0.30 g, 92%).

MS(ESI) m/z: (M+1) 339.1; $^1$HNMR (400 MHz, DMSO-d6): δ 2.43-2.47 (m, 1H); 2.74-2.82 (m, 1H); 2.93-2.96 (m, 1H); 3.32 (s, 3H); 3.74-3.78 (m, 1H); 4.07-4.12 (m, 1H); 4.28-4.34 (m, 2H); 7.93 (d, J=8.8 Hz, 1H); 8.6-8.39 (m, 1H); 9.04 (d, J=2.4 Hz, 1H)

Synthesis of 2-[1-[[5-oxo-1-[6-(trifluoromethyl)-3-pyridyl]pyrrolidin-3-yl]methyl]pyrazol-4-yl]-5-propyl-3-(2-trimethylsilylethoxymethyl)imidazo[2,1-b]purin-4-one To a solution 2.2 (0.25 g, 0.605 mmol) in DMF (7 mL) was added cesium carbonate (0.394 g, 1.21 mmol), 3.1 (0.244 g, 0.726 mmol). The mixture was stirred at 80° C. for 16 hours. Reaction completion was confirmed by TLC then cooled to room temperature and added water, solid obtained was filtered, washed with cold water then washed with n-hexane, dried to afford the title compound 3.2 as off white solid (0.1 g, 25%).

MS(ESI) m/z: 656.0 (M+1); $^1$H NMR: Not recorded

Step 2: Synthesis of 2-[1-[[5-oxo-1-[2-(trifluoromethyl)-4-pyridyl]pyrrolidin-3-yl]methyl]pyrazol-4-yl]-5-propyl-3H-imidazo[2,1-b]purin-4-one A solution of 3.2 (0.1 g, 0.15 mmol) in DCM (9 mL) was added TFA (1 mL) and stirred at room temperature for 4 hours. Reaction completion was confirmed by TLC then concentrated under vacuo to obtain a crude product. The residue was basified by aqueous NaHCO$_3$ solution up to PH (7-8) then solid obtained was filtered, washed with n-hexane, dried and purified by LCMS purification method to obtain the title compound C1 as a white solid (0.070 g, 87%).

MS(ESI) m/z: 526.2 (M+1); $^1$H NMR (400 MHz, DMSO-d$_6$): δ 0.92 (t, J=7.2 Hz, 3H); 1.71-1.78 (m, 2H); 2.51-2.53 (m, 1H); 2.72-2.79 (m, 1H); 3.08-3.09 (m, 1H); 3.77-3.82 (m, 1H); 4.04-4.08 (m, 1H); 4.19 (t, J=7.2 Hz, 2H); 4.38 (d, J=7.2 Hz, 2H); 7.16 (d, J=1.6 Hz, 1H); 7.65 (d, J=1.6 Hz, 1H); 7.89 (d, J=8.4 Hz, 1H); 8.14 (s, 1H); 8.27-8.30 (m, 1H); 8.48 (s, 1H); 9.01 (d, J=2.4 Hz, 1H); 13.9 (brs, 1H)

Following examples as shown in Table were prepared according to similar sequence of procedures as used for the synthesis of Example C1

| Ex. No. | Structure / IUPAC Name | $^1$H NMR (400 MHz) data | MS(ESI)m/z: (M + 1) |
|---|---|---|---|
| C2 | 2-[1-[[5-oxo-1-[5-(trifluoromethyl)-3-pyridyl]pyrrolidin-3-yl]methyl]pyrazol-4-yl]-5-propyl-3H-imidazo[2,1-b]purin-4-one | DMSO-d$_6$: δ 0.92 (t, J = 7.6 Hz, 3H); 1.72-1.78 (m, 2H); 2.51-2.53 (m, 1H); 2.75-2.79 (m, 1H); 3.07-3.09 (m, 1H); 3.79-3.82 (m, 1H); 4.07-4.09 (m, 1H); 4.19 (t, J = 7.2 Hz, 2H); 4.38 (d, J = 8.8 Hz, 2H); 7.16 (s, 1H); 7.65 (s, 1H); 8.15 (s, 1H); 8.49 (br s, 2H); 8.71 (s, 1H); 9.03 (s, 1H); 13.9 (br s, 1H). | 526.2 |
| C3 | 2-[1-[[5-oxo-1-[3-(trifluoromethyl)phenyl]pyrrolidin-3-yl]methyl]pyrazol-4-yl]-5-propyl-3H-imidazo[2,1-b]purin-4-one | DMSO-d$_6$: δ 0.90 (t, J = 7.2 Hz, 3H); 1.70-1.76 (m, 2H); 2.63-2.74 (m, 2H); 3.00-3.15 (m, 1H); 3.71-3.75 (m, 1H); 4.00 (t, J = 8.0 Hz, 1H); 4.16 (t, J = 6.8 Hz, 2H); 4.36 (d, J = 6.8 Hz, 2H); 7.15 (dd, J = 1.6 Hz, 1H); 7.45 (d, J = 8.0 Hz, 1H); 7.59 (dd, J = 8.0 Hz, 1H); 7.65 (dd, J = 1.6 Hz, 1H); 7.74 (d, J = 8.4 Hz, 1H); 8.11-8.15 (m, 2H); 8.49 (s, 1H); 13.88 (br s, 1H). | 525.2 |

Example D1: 2-[1-[2-(1-piperidyl)ethyl]pyrazol-4-yl]-5-propyl-3H-imidazo[2,1-b]purin-4-one

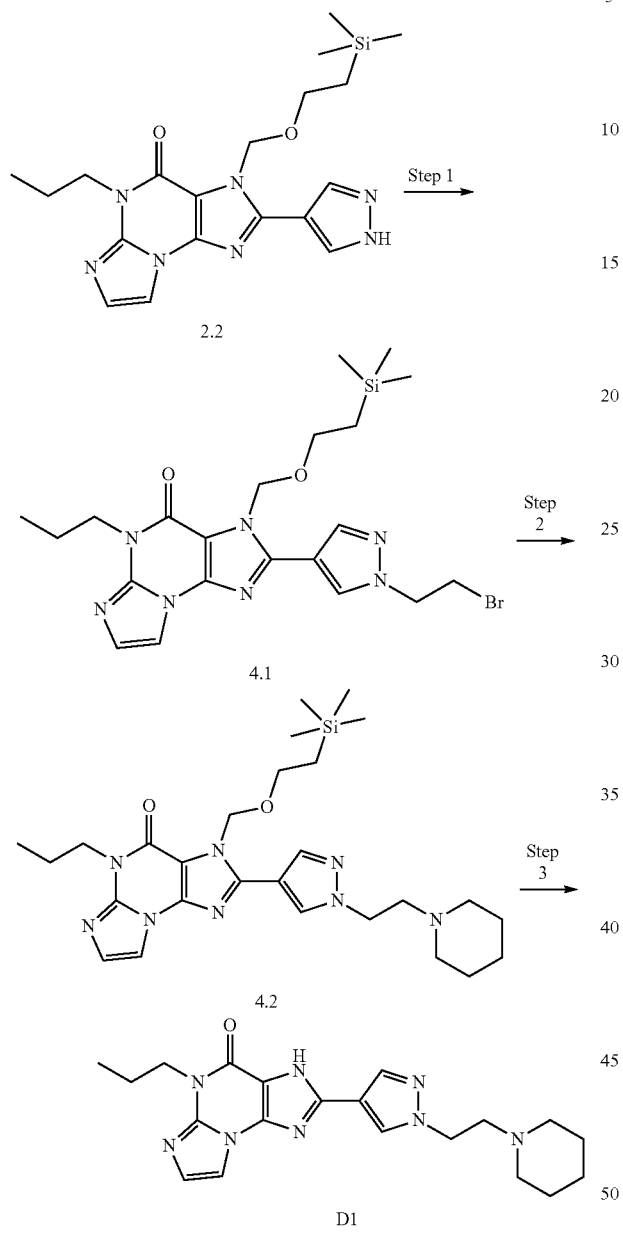

Step 1: Synthesis of 2-[1-(2-bromoethyl)pyrazol-4-yl]-5-propyl-3-(2-trimethylsilylethoxymethyl)imidazo[2,1-b]purin-4-one The title compound 4.1 was obtained as an off-white solid (0.35 g, 69%) in a similar manner to that of example B1 step 4 using the compound 2.2 (0.4 g, 0.97 mmol), potassium carbonate (0.4 g, 2.90 mmol) and 1,2-dibromoethane (0.33 mL, 3.87 mmol).

MS(ESI) m/z: 519.9, 522.9 (M+1); $^1$H NMR (400 MHz, DMSO-d$_6$): δ −0.086 (s, 9H); 0.86-0.92 (m, 5H); 1.72-1.76 (m, 2H); 3.70 (t, J=8.0 Hz, 2H); 3.92 (t, J=5.6 Hz, 2H); 4.18 (t, J=7.2 Hz, 2H); 4.64 (t, J=5.6 Hz, 2H); 5.92 (s, 2H); 7.19 (d, J=1.6 Hz, 1H); 7.72 (d, J=1.2 Hz, 1H); 8.10 (s, 1H); 8.48 (s, 1H)

Step 2: Synthesis of 2-[1-[2-(1-piperidyl)ethyl]pyrazol-4-yl]-5-propyl-3-(2-trimethylsilylethoxymethyl)imidazo[2,1-b]purin-4-one To a solution 4.1 (0.15 g, 0.29 mmol) in DMF (5 mL) was added DIPEA (0.14 mL, 0.86 mmol), and piperidine (0.085 mL, 0.86 mmol). The mixture was stirred at 60° C. for 16 hours. Reaction completion was confirmed by TLC then cooled to room temperature and added water (50 mL). Aqueous layer was extracted with ethyl acetate (3×20 mL), washed with brine (20 mL), dried over Na$_2$SO$_4$ and concentrated under vacuo to obtain a crude product. The residue was purified by LCMS purification method to obtain the title compound 4.2 as white solid. (0.05 g, 33%).

MS(ESI) m/z: 525.4 (M+1); $^1$H NMR (400 MHz, DMSO-d$_6$): δ −0.088 (s, 9H); 0.86-0.93 (m, 9H); 1.23-1.28 (m, 4H); 1.74-1.82 (m, 4H); 2.49-2.50 (m, 2H); 3.71 (t, J=7.2 Hz, 2H); 4.17-4.24 (m, 4H); 5.94 (s, 2H); 7.19 (d, J=1.6 Hz, 1H); 7.72 (d, J=1.6 Hz, 1H); 8.05 (s, 1H); 8.41 (s, 1H)

Step 3: Synthesis of 2-[1-[2-(1-piperidyl)ethyl]pyrazol-4-yl]-5-propyl-3H-imidazo[2,1-b]purin-4-one The title compound D1 was obtained as an off-white solid (0.02 g., 54%) in a similar manner to that of Example B1 step 5 using the compound 4.2 (0.05 g, 0.095 mmol) and ethanol: 2N HCl (10 mL)

MS(ESI) m/z: 395.3 (M+1); $^1$H NMR (400 MHz, DMSO-d$_6$): δ 0.93 (t, J=7.6 Hz, 3H); 1.63-1.72 (m, 3H); 1.74-1.1.84 (m, 4H); 2.93-2.96 (m, 3H); 3.45-3.48 (m, 2H); 3.60 (q, J=6.0 Hz, 2H); 4.18 (t, J=7.2 Hz, 2H); 4.65 (t, J=5.6 Hz, 2H); 7.18 (d, J=1.2 Hz, 1H); 7.66 (d, J=1.2 Hz, 1H); 8.24 (s, 1H); 8.54 (s, 1H); 13.95 (br s, 1H)

Example E1: 2-[1-[[3-(hydroxymethyl)phenyl]methyl]pyrazol-4-yl]-5-propyl-3H-imidazo[2,1-b]purin-4-one

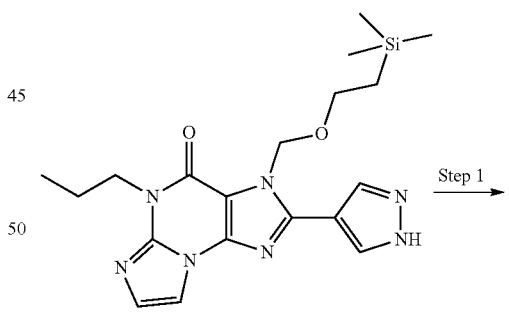

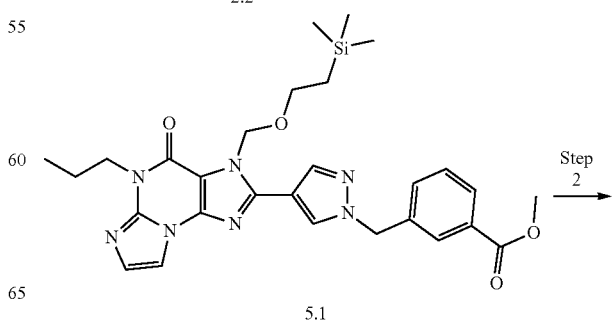

-continued

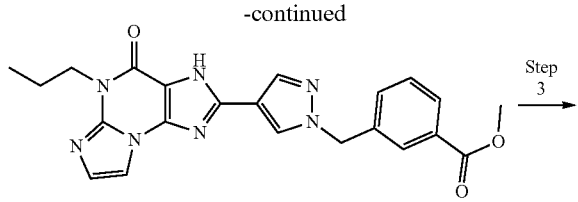

5.2

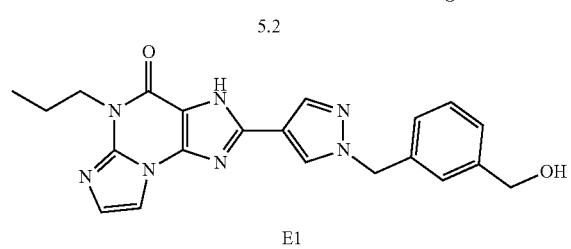

E1

Step 1: methyl 3-[[4-[4-oxo-5-propyl-3-(2-trimethylsilylethoxymethyl)imidazo[2,1-b]purin-2-yl]pyrazol-1-yl]methyl]benzoate The title compound 5.1 was obtained as an off-white solid (0.4 g, 98%) in a similar manner to that of example B1 step 4 using the compound 2.2 (0.3 g, 0.72 mmol), potassium carbonate (0.15 g, 1.09 mmol) and methyl 3-(bromomethyl)benzoate (0.18 g, 0.799 mmol).

MS(ESI) m/z: 562.0 (M+1); $^1$H NMR (400 MHz, DMSO-$d_6$): δ −0.117 (s, 9H); 0.84-0.93 (m, 5H); 1.72-1.78 (m, 2H); 3.69 (t, J=8.0 Hz, 2H); 3.85 (s, 3H); 4.19 (t, J=6.8 Hz, 2H); 5.56 (s, 2H); 5.93 (s, 2H); 7.20 (d, J=1.6 Hz, 1H); 7.54 (t, J=7.6 Hz, 1H); 7.63 (d, J=8.0 Hz, 1H); 7.73 (d, J=1.6 Hz, 1H); 7.92 (dd, J=1.6, 9.2 Hz, 1H); 7.96 (d, J=16 Hz, 1H); 8.10 (s, 1H); 8.59 (s, 1H).

Step 2: methyl 3-[[4-(4-oxo-5-propyl-3H-imidazo[2,1-b]purin-2-yl)pyrazol-1-yl]methyl]benzoate The title compound 5.2 was obtained as an off-white solid (0.3 g, 98%) in a similar manner to that of Example B1 step 5 using the compound 5.1 (0.4 g, 0.71 mmol) and ethanol:2N HCl (24 mL)

MS(ESI) m/z: 432.2 (M+1); $^1$H NMR (400 MHz, DMSO-$d_6$): δ 0.92 (t, J=7.6 Hz, 3H); 1.72-1.77 (m, 2H); 3.31 (s, 3H); 4.15-4.19 (m, 2H); 5.52 (s, 2H); 7.17 (d, J=1.6 Hz, 1H); 7.53-7.56 (m, 1H); 7.59-7.61 (m, 1H); 7.68 (d, J=1.6 Hz, 1H); 7.90-7.93 (m, 2H); 8.17 (s, 1H); 8.55 (s, 1H); 13.86 (s, 1H).

Step 3: 2-[1-[[3-(hydroxymethyl)phenyl]methyl]pyrazol-4-yl]-5-propyl-3H-imidazo[2,1-b]purin-4-one To a solution of 5.2 (0.05 g, 0.116 mmol) in DCM (10 mL) was added DIBAL (0.32 mL, 0.58 mmol, 25% solution in Toluene) at −50° C. and the reaction mixture was warm up to 0° C. Reaction completion was confirmed by TLC then reaction mixture was quenched with ammonium chloride solution and extracted with 5% MeOH in DCM (3×20 mL). The combined organic layer was washed with brine and dried over $Na_2SO_4$ and concentrated under vacuo to obtain a crude product. The residue was purified by preparative TLC to obtain the title compound E1 as off white solid (0.010 g, 21%).

MS(ESI) m/z: 404.2 (M+1); $^1$H NMR (400 MHz, DMSO-$d_6$): δ 0.92 (t, J=7.6 Hz, 3H); 1.72-1.78 (m, 2H); 4.17 (t, J=7.6 Hz, 2H); 4.48 (d, J=6.0 Hz, 2H); 5.21 (d, J=6.0 Hz, 1H); 5.40 (s, 2H); 7.16-7.20 (m, 2H); 7.24-7.34 (m, 3H); 7.68 (d, J=1.2 Hz, 1H); 8.14 (s, 1H); 8.49 (s, 1H); 13.93 (br s, 1H).

Example F1: 2-[1-[[3-(1-hydroxy-1-methyl-ethyl)phenyl]methyl]pyrazol-4-yl]-5-propyl-3H-imidazo[2,1-b]purin-4-one

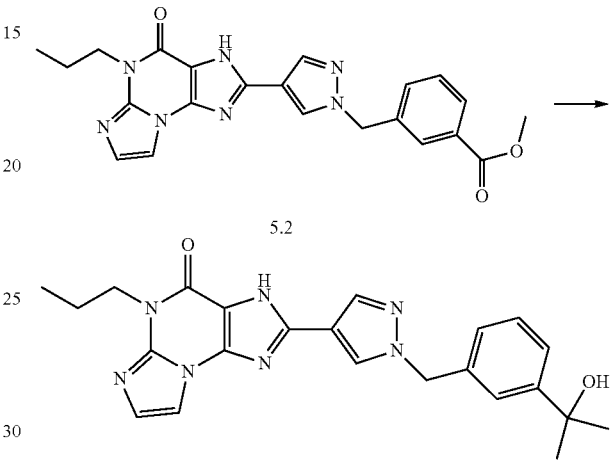

To a solution of 5.2 (0.05 g, 0.115 mmol) in THF (10 mL) was added methylmagnesium bromide (0.57 mL, 0.57 mmol, 1M solution in THF) at −50° C. and the reaction mixture was warm to 0° C. Reaction completion was confirmed by TLC then reaction mixture was quenched with ammonium chloride solution and extracted with 5% MeOH in DCM (3×20 mL). The combined organic layer was washed with brine and dried over $Na_2SO_4$ and concentrated under vacuo to obtain a crude product. The residue was purified by preparative TLC to obtain the title compound F1 as an off white solid (0.01 g, 20%).

MS(ESI) m/z: 432.2 (M+1); $^1$H NMR (400 MHz, DMSO-$d_6$): δ 0.92 (t, J=7.6 Hz, 3H); 1.40 (s, 6H); 1.71-1.77 (m, 2H); 4.17 (t, J=8.0 Hz, 2H); 5.02 (s, 1H); 5.40 (s, 2H); 7.11 (d, J=8.0 Hz, 1H); 7.16 (d, J=1.6 Hz, 1H); 7.29 (t, J=8.0 Hz, 1H); 7.39 (d, J=8.0 Hz, 1H); 7.49 (s, 1H); 7.68 (d, J=1.6 Hz, 1H); 8.15 (s, 1H); 8.49 (s, 1H); 13.86 (br s, 1H).

Example G1: 3-[[4-(4-oxo-5-propyl-3H-imidazo[2,1-b]purin-2-yl)pyrazol-1-yl]methyl]benzoic Acid

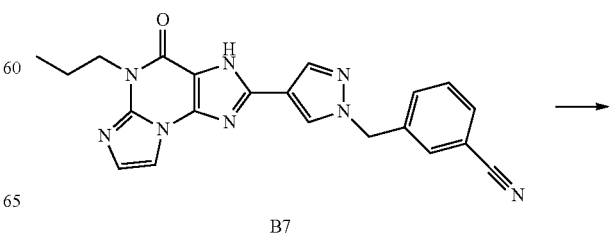

B7

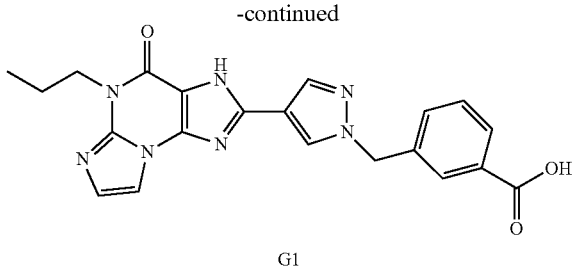

G1

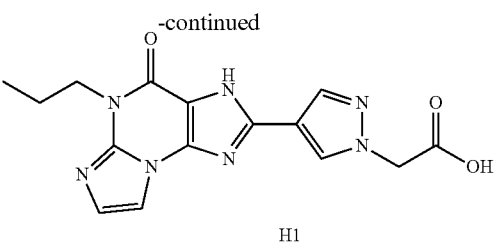

H1

To a solution of B7 (0.07 g, 0.175 mmol) in methanol:water (3:1.10 mL) was added NaOH (0.021 g, 0.527 mmol) and the reaction mixture was stirred at 80° C. for 16 hours. Reaction completion was confirmed by TLC then reaction mixture was cooled to room temperature and evaporated to dryness. Acidified with 2N HCl to pH (3-4) and solid obtained was filtered, washed with n-hexane and dried to obtain the title compound G1 as off white solid (0.02 g, 27%).

MS(ESI) m/z: 418.0 (M+1); $^1$H NMR (400 MHz, DMSO-$d_6$): δ 0.92 (t, J=7.2 Hz, 3H); 1.72-1.77 (m, 2H); 4.17 (t, J=7.6 Hz, 2H); 5.47 (s, 2H); 7.16 (d, J=1.6 Hz 1H); 7.39 (br s, 1H); 7.45-7.47 (m, 2H); 7.68 (d, J=1.6 Hz, 1H); 7.81-7.84 (m, 1H); 7.99 (br s, 1H); 8.16 (s, 1H); 8.53 (s, 1H); 13.92 (br s, 1H)

Example H1: 2-[4-(4-oxo-5-propyl-3H-imidazo[2,1-b]purin-2-yl)pyrazol-1-yl]acetic Acid Step 1: methyl 2-[4-[4-oxo-5-propyl-3-(2-trimethylsilylethoxymethyl)imidazo[2,1-b]purin-2-yl]pyrazol-1-yl]acetate The title compound 6.1 was obtained as an off-white solid (0.2 g, 83%) in a similar manner to that of example B1 step 4 using the compound 2.2 (0.2 g, 0.484 mmol), potassium carbonate (0.14 g, 1.06 mmol) and methyl bromoacetate (0.06 g, 0.58 mmol).

MS(ESI) m/z: 486.0 (M+1); $^1$H NMR (400 MHz, DMSO-$d_6$): δ −0.11 (s, 9H); 0.96-1.01 (m, 5H); 1.81-1.86 (m, 2H); 3.78-3.82 (m, 5H); 4.28 (t, J=6.8 Hz, 2H); 5.33 (s, 2H); 6.01 (s, 2H); 7.28 (d, J=1.6 Hz, 1H); 7.82 (d, J=1.6 Hz, 1H); 8.17 (s, 1H); 8.54 (s, 1H)

Step 2: methyl 2-[4-(4-oxo-5-propyl-3H-imidazo[2,1-b]purin-2-yl)pyrazol-1-yl]acetate The title compound 6.2 was obtained as an off-white solid (0.13 g, 88%) in a similar manner to that of Example B1 step 5 using the compound 6.1 (0.2 g, 0.4 mmol) and ethanol: 2N HCl (12 mL)

MS(ESI) m/z: 356.0 (M+1); $^1$H NMR (400 MHz, DMSO-$d_6$): Not recorded

Step 3: 2-[4-(4-oxo-5-propyl-3H-imidazo[2,1-b]purin-2-yl)pyrazol-1-yl]acetic Acid To a solution of 6.2 (0.2 g, 0.54 mmol) in ethanol:water (2:1) (10 mL) was added NaOH (0.065 g, 1.62 mmol) and the reaction mixture was stirred at 80° C. for 3 hours. Reaction completion was confirmed by TLC then reaction mixture was cooled to room temperature and evaporated to dryness. The residue was acidified with 2N HCl to pH 3 and solid obtained was filtered, washed n-hexane dried to obtain the title compound H1 as an off white solid (0.17 g, 92%).

MS(ESI) m/z: 342.2 (M+1); $^1$H NMR (400 MHz, DMSO-$d_6$): δ 0.93 (t, J=7.6 Hz, 3H); 1.75 (q, J=7.2 Hz, 2H); 4.18 (t, J=7.6 Hz, 2H); 5.08 (s, 2H); 7.18 (br s, 1H); 7.77 (br s, 1H); 8.14 (s, 1H); 8.43 (s, 1H); 13.22 (br s, 1H); 13.93 (br s, 1H)

Example I1: 2-[1-(2-hydroxy-2-methyl-propyl)pyrazol-4-yl]-5-propyl-3H-imidazo[2,1-b]purin-4-one

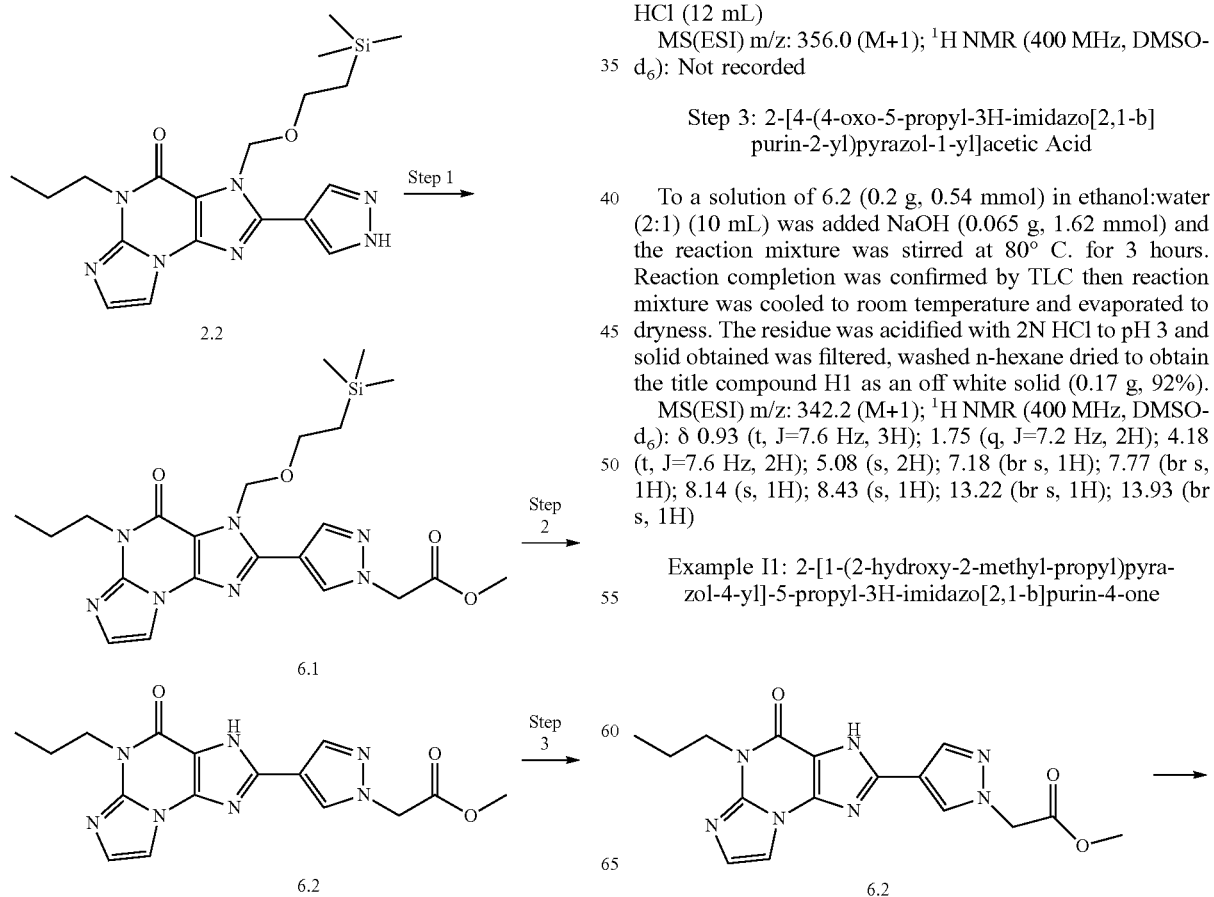

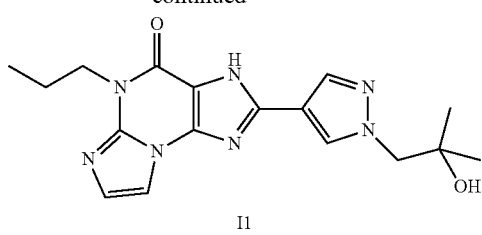

I1

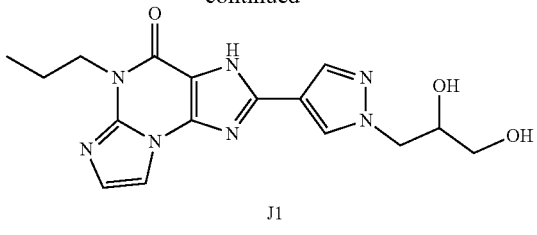

J1

The title compound I1 was obtained as an off-white solid (0.01 g, 21%) in a similar manner to that of example F1 using the compound 6.2 (0.05 g, 0.14 mmol), THF (10 mL) and methylmagnesium bromide (0.57 mL, 0.57 mmol, 1M solution in THF)

MS(ESI) m/z: 356.2 (M+1); $^1$H NMR (400 MHz, DMSO-$d_6$): δ 0.92 (t, J=7.6 Hz, 3H); 1.09 (s, 6H); 1.72-1.78 (m, 2H); 4.09 (s, 2H); 4.19 (t, J=7.6 Hz, 2H); 4.78 (s, 1H); 7.16 (s, 1H); 7.71 (s, 1H); 8.10 (s, 1H); 8.37 (s, 1H); 13.86 (br s, 1H).

Example J1: 2-[1-(2,3-dihydroxypropyl)pyrazol-4-yl]-5-propyl-3H-imidazo[2,1-b]purin-4-one

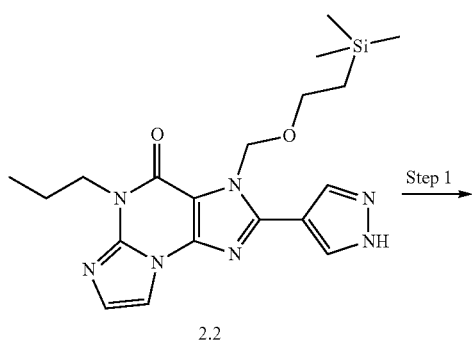

2.2

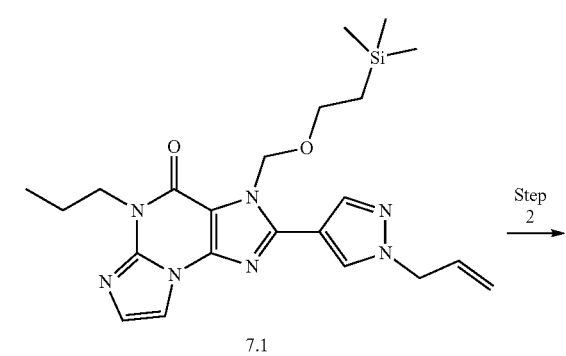

7.1

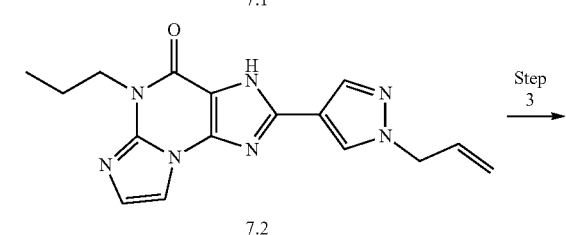

7.2

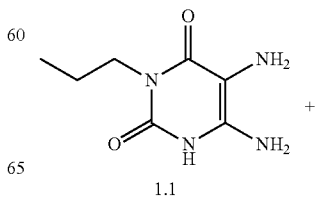

1.1

Step 1: 2-(1-allylpyrazol-4-yl)-5-propyl-3-(2-trimethylsilylethoxymethyl)imidazo[2,1-b]purin-4-one The title compound 7.1 was obtained as an off-white solid (0.15 g, 91%) in a similar manner to that of example B1 step 4 using the compound 2.2 (0.15 g, 0.36 mmol), potassium carbonate (0.12 g, 0.90 mmol) and allyl bromide (0.044 g, 0.36 mmol).

MS(ESI) m/z: 454.0 (M+1); $^1$H NMR (400 MHz, DMSO-$d_6$): δ −0.11 (s, 9H); 0.92-1.01 (m, 5H); 1.79-1.86 (m, 2H); 3.80 (t, J=8.0 Hz, 2H); 4.28 (t, J=6.8 Hz, 2H); 4.98 (d, J=5.2 Hz, 2H); 5.27-5.36 (m, 2H); 6.02 (s, 2H); 6.11-6.19 (m, 1H); 7.28 (s, 1H); 7.82 (s, 1H); 8.17 (s, 1H); 8.48 (s, 1H).

Step 2: 2-(1-allylpyrazol-4-yl)-5-propyl-3H-imidazo[2,1-b]purin-4-one

The title compound 7.2 was obtained as an off-white solid (0.088 g., 83%) in a similar manner to that of Example B1 step 5 using the compound 7.1 (0.15 g, 0.33 mmol).

MS(ESI) m/z: 324.0 (M+1); $^1$H NMR (400 MHz, DMSO-$d_6$): δ 0.94 (t, J=7.6 Hz, 3H); 1.72-1.75 (m, 2H); 4.17 (t, J=7.2 Hz, 2H); 4.86 (d, J=6.0 Hz, 2H); 5.18-5.27 (m, 2H); 6.01-6.09 (m, 1H); 7.38 (s, 1H); 7.84 (s, 1H); 8.15 (s, 1H); 8.42 (s, 1H); 14.12 (br s, 1H).

Step 3: 2-[1-(2,3-dihydroxypropyl)pyrazol-4-yl]-5-propyl-3H-imidazo[2,1-b]purin-4-one Osmium tetraoxide (0.005 g, 0.019 mmol) and N-methylmorpholine N-oxide (0.047 g, 0.40 mmol) was added to the suspended mixture of 7.2 (0.088 g, 0.27 mmol) in acetone-water (1:1, 10 mL) at room temperature and the reaction mixture was stirred for overnight. Reaction completion was confirmed by TLC. The solid obtained was filtered and purified using preparative TLC method to obtain the title compound J1 as an off white solid (0.018 g, 33%).

MS(ESI) m/z: 358.2 (M+1); $^1$HNMR (400 MHz, DMSO-d6): 0.93 (t, J=7.6 Hz, 3H); 1.73-1.79 (m, 2H); 3.32-3.40 (m, 2H); 3.80-3.82 (m, 1H); 4.04-4.09 (m, 1H); 4.18 (t, J=7.2 Hz, 2H); 4.28-4.32 (m, 1H); 4.79 (t, J=6.0 Hz, 1H); 5.07 (d, J=5.2 Hz, 1H); 7.17 (d, J=1.6 Hz, 1H); 7.71 (d, J=1.6 Hz, 1H); 8.11 (s, 1H); 8.37 (s, 1H); 13.86 (s, 1H)

Example K1: 2-(3,4-dimethoxyphenyl)-5-propyl-3H-imidazo[2,1-b]purin-4-one

+

-continued

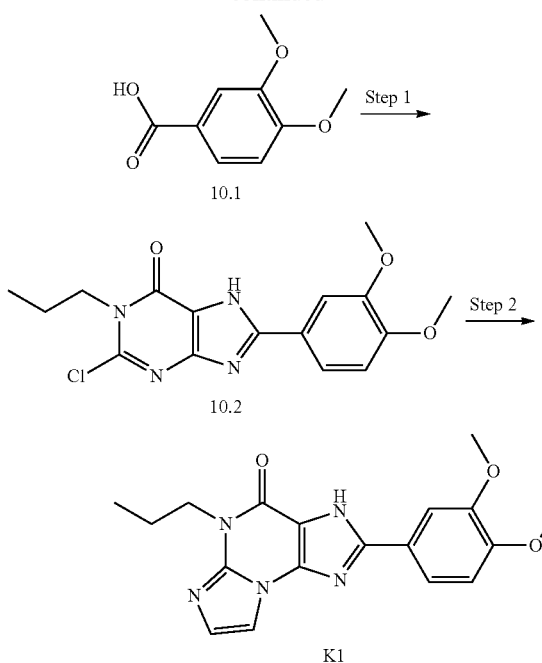

Step 1: 2-chloro-8-(3,4-dimethoxyphenyl)-1-propyl-7H-purin-6-one

A mixture of 1.1 (1.0 g, 5.43 mmol), 10.1 (0.99 g, 5.43 mmol) and POCl₃ (10 mL) were heated at 120-125° C. for 72 hours. Reaction completion was confirmed by TLC, mixture was cooled to 20-25° C. It was then concentrated under vacuo and to the residue cold water was added slowly and solid material was separated. It was filtered off and washed with cold water, dried under vacuo. The crude product was purified by column chromatography using silica gel (230-400 mesh) and 0.5 to 4% methanol in DCM as an eluent to obtain 10.2 as a pale yellow solid. (1.1 g, 58%)

ESI-MS (m/z): 349.2 (M+1); ¹HNMR Not recorded

Step 2: 2-(3,4-dimethoxyphenyl)-5-propyl-3H-imidazo[2,1-b]purin-4-one

The title compound was obtained as an yellow solid (0.11 g, 20%) in a similar manner to that of Example A1 step 4 using the compound 8.2 (0.2 g, 0.575 mmol), NMP (5 mL), DIPEA (0.38 mL, 2.30 mmol), and aminoacetaldehyde dimethyl acetal (0.25 mL, 2.29 mmol).

MS(ESI) m/z: 354.2 (M+1); ¹HNMR (400 MHz, DMSO-d₆): δ 0.91 (t, J=7.2 Hz, 3H); 1.73-1.75 (m, 2H); 3.79 (s, 3H); 3.85 (s, 3H); 4.17 (t, J=7.2 Hz, 2H); 7.08 (d, J=8.4 Hz, 1H); 7.14 (s, 1H); 7.72-7.78 (m, 3H); 13.96 (br s, 1H.

Following examples as shown in Table were prepared according to similar sequence of procedures as used for the synthesis of Example K1

| Ex. No. | Structure IUPAC Name | ¹H NMR(400 MHz) data | MS(ESI)m/z: (M + 1) |
|---|---|---|---|
| K2 | 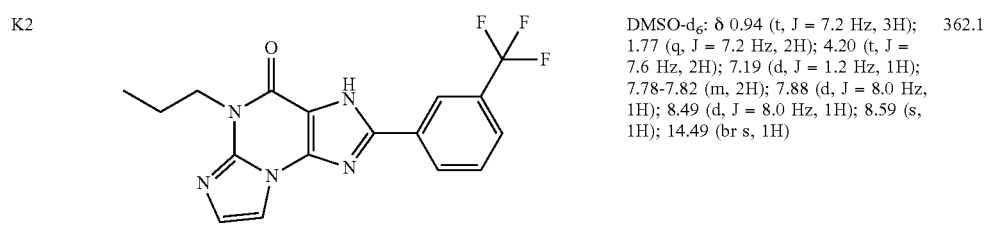<br>5-propyl-2-[3-(trifluoromethyl)phenyl]-3H-imidazo[2,1-b]purin-4-one | DMSO-d₆: δ 0.94 (t, J = 7.2 Hz, 3H); 1.77 (q, J = 7.2 Hz, 2H); 4.20 (t, J = 7.6 Hz, 2H); 7.19 (d, J = 1.2 Hz, 1H); 7.78-7.82 (m, 2H); 7.88 (d, J = 8.0 Hz, 1H); 8.49 (d, J = 8.0 Hz, 1H); 8.59 (s, 1H); 14.49 (br s, 1H) | 362.1 |
| K3 | 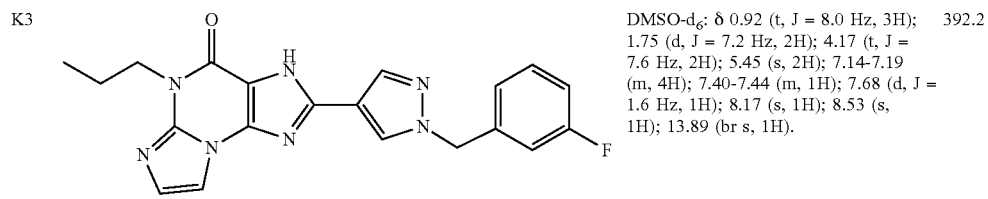<br>2-[1-[(3-fluorophenyl)methyl]]pyrazol-4-yl]-5-propyl-3H-imidazo[2,1-b]purin-4-one | DMSO-d₆: δ 0.92 (t, J = 8.0 Hz, 3H); 1.75 (d, J = 7.2 Hz, 2H); 4.17 (t, J = 7.6 Hz, 2H); 5.45 (s, 2H); 7.14-7.19 (m, 4H); 7.40-7.44 (m, 1H); 7.68 (d, J = 1.6 Hz, 1H); 8.17 (s, 1H); 8.53 (s, 1H); 13.89 (br s, 1H). | 392.2 |
| K4 | 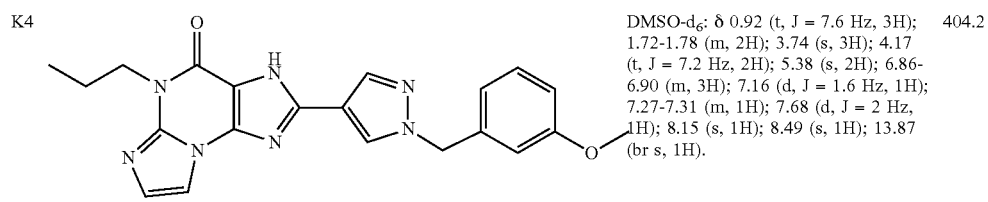 | DMSO-d₆: δ 0.92 (t, J = 7.6 Hz, 3H); 1.72-1.78 (m, 2H); 3.74 (s, 3H); 4.17 (t, J = 7.2 Hz, 2H); 5.38 (s, 2H); 6.86-6.90 (m, 3H); 7.16 (d, J = 1.6 Hz, 1H); 7.27-7.31 (m, 1H); 7.68 (d, J = 2 Hz, 1H); 8.15 (s, 1H); 8.49 (s, 1H); 13.87 (br s, 1H). | 404.2 |

| Ex. No. | Structure IUPAC Name | $^1$H NMR(400 MHz) data | MS(ESI)m/z: (M + 1) |
|---|---|---|---|
| K5 | 2-[1-[(3-methoxyphenyl)methyl]pyrazol-4-yl]-5-propyl-3H-imidazo[2,1-b]purin-4-one | DMSO-d$_6$: δ 0.92 (t, J = 7.6 Hz, 3H); 1.38-1.39 (m, 2H); 1.48-1.53 (m, 4H); 1.73-1.79 (m, 2H); 2.45 (br s, 4H); 2.69 (t, J = 6.0 Hz, 2H); 4.13-4.20 (m, 4H); 7.09 (d, J = 8.8 Hz, 2H); 7.17 (d, J = 0.8 Hz, 1H); 7.74 (d, J = 1.2 Hz, 1H); 8.14 (d, J = 8.8 Hz, 2H); 13.58 (br s, 1H) | 421.3 |
| | 2-[4-[2-(1-piperidyl)ethoxy]phenyl]-5-propyl-3H-imidazo[2,1-b]purin-4-one | | |
| K6 | 2-(5-methoxy-2-pyridyl)-5-propyl-3H-imidazo[2,1-b]purin-4-one | DMSO-d$_6$: δ 0.92 (t, J = 8.0 Hz, 3H); 1.75-1.75 (m, 2H); 3.75 (s, 3H); 4.11-4.19 (m, 2H); 7.16 (br s, 1H); 7.72 (br s, 1H); 7.78 (d, J = 8.8 Hz, 1H); 7.99 (br s, 1H); 8.20 (d, J = 8.4 Hz, 1H) | 325.2 |
| K7 | 2-(4-ethoxyphenyl)-5-propyl-3H-imidazo[2,1-b]purin-4-one | DMSO-d$_6$: δ 0.93 (t, J = 7.2 Hz, 3H); 1.36 (t, J = 6.8 Hz, 3H); 1.74-1.80 (m, 2H); 4.09-4.14 (m, 2H); 4.19 (t, J = 7.6 Hz, 2H); 7.08 (d, J = 8.4 Hz, 2H); 7.18 (br s, 1H); 7.74 (br s, 1H); 8.14 (d, J = 8.4 Hz, 2H); 13.95 (br s, 1H) | 338.2 |

Example L1: N-isopropyl-2-[4-(4-oxo-5-propyl-3H-imidazo[2,1-b]purin-2-yl)pyrazol-1-yl]acetamide

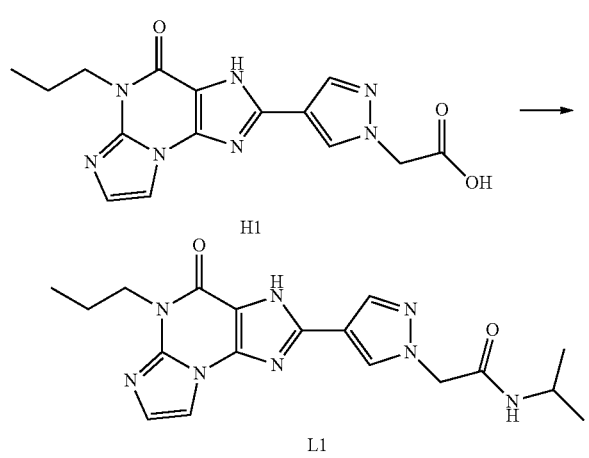

To a solution H1 (0.05 g, 0.14 mmol) in DMF (2 mL) was added DIPEA (0.071 mL, 0.42 mmol), isopropyl amine (0.013 mL, 0.15 mmol), EDCl.HCl (0.04 g, 0.21 mmol) and hydroxyl benzotriazole (0.028 g, 0.21 mmol). The mixture was stirred at 25° C. for 16 hours. Reaction completion was confirmed by TLC and added water (20 mL). Solid material precipitated was filtered off and washed with cold water, dried under vacuo. The crude product was purified by combiflash column chromatography to obtain the title compound O1 as off white solid. (0.015 g, 27%).

MS(ESI) m/z: 383.2 (M+1); $^1$H NMR (400 MHz, DMSO-d$_6$): δ 0.92 (t, J=7.6 Hz, 3H); 1.09 (d, J=6.8 Hz, 6H); 1.72-1.78 (m, 2H); 3.84-3.86 (m, 1H); 4.18 (t, J=8.0 Hz, 2H); 4.84 (s, 2H); 7.17 (br s, 1H); 7.70 (br s, 1H); 8.11 (s, 1H); 8.15 (d, J=6.8 Hz, 1H); 8.39 (s, 1H); 13.50 (br s, 1H)

Following examples as shown in Table were prepared according to similar sequence of procedures as used for the synthesis of Example L1

| Ex. No. | Structure IUPAC Name | ¹H NMR(400 MHz) data | MS(ESI)m/z: (M + 1) |
|---|---|---|---|
| L2 | 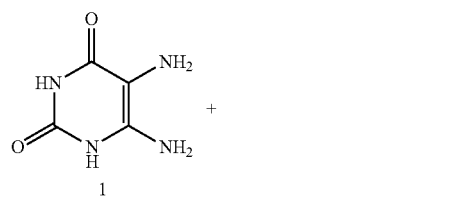  N-(oxetan-3-yl)-2-[4-(4-oxo-5-propyl-3H-imidazo[2,1-b]purin-2-yl)pyrazol-1-yl]acetamide | DMSO-d₆: δ 0.92 (t, J = 7.2 Hz, 3H); 1.72-1.78 (m, 2H); 4.18 (t, J = 7.2 Hz, 2H); 4.45 (t, J = 6.4 Hz, 2H); 4.73 (t, J = 6.4 Hz, 2H); 4.79-4.83 (m, 1H); 4.92 (s, 2H); 7.17 (d, J = 1.6 Hz, 1H); 7.70 (d, J = 1.6 Hz, 1H); 8.11 (s, 1H); 8.40 (s, 1H); 9.04 (d, J = 6.8 Hz, 1H); 13.50 (br s, 1H) | 397.2 |

Example: 4-propyl-2-[1-[[3-(trifluoromethyl)phenyl]methyl]pyrazol-4-yl]-1H-imidazo[2,1-f]purin-5-one

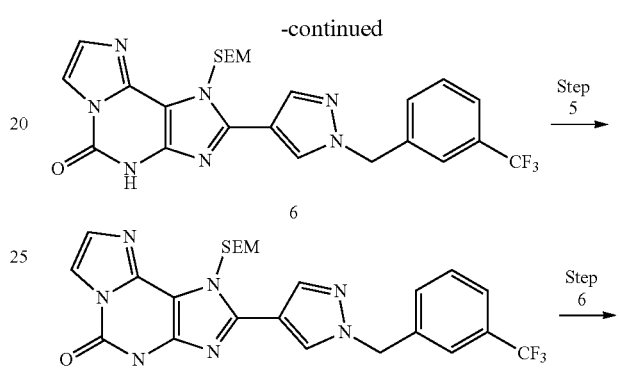

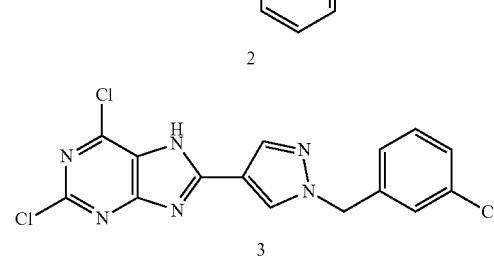

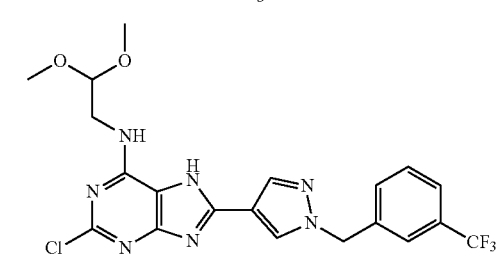

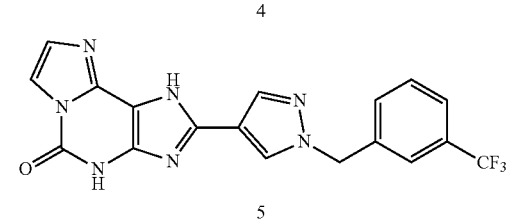

Step 1: 2,6-dichloro-8-[1-[[3-(trifluoromethyl)phenyl]methyl]pyrazol-4-yl]-7H-purine A mixture of 1 (3.94 g, 27.80 mmol), 2 (5 g, 18.52 mmol) and POCl₃ (50 mL) were heated at 120-125° C. for 72 hours. Reaction completion was confirmed by TLC, mixture was cooled to 20-25° C. It was then concentrated under vacuo and to the residue cold water was added slowly and the mixture was extracted with ethyl acetate (3×200 mL). The combined organic layer was washed with brine (300 mL), dried over Na₂SO₄ and concentrated under vacuo to obtain a crude product. The crude product was purified by combi-flash column chromatography using 30-35% ethylacetate in hexane as an eluent to obtain 3 as a pale yellow solid. (3.5 g, 46%)

ESI-MS (m/z): 412.9 (M+1); ¹H NMR (400 MHz, CDCl₃): 5.54 (s, 2H); 7.45-7.54 (m, 3H); 7.60-7.62 (m, 1H); 8.15 (s, 1H); 8.21 (s, 1H).

Step 2: 2-chloro-N-(2,2-dimethoxyethyl)-8-[1-[[3-(trifluoromethyl) phenyl]methyl]pyrazol-4-yl]-7H-purin-6-amine To a solution of 3 (0.5 g, 1.21 mmol) in NMP (10 mL) was added DIPEA (0.20 mL, 1.21 mmol), and aminoacetaldehyde dimethyl acetal (0.16 mL, 1.45 mmol). The mixture was stirred at 130° C. for 1 h. Reaction completion was confirmed by TLC, then cooled to room temperature and the reaction mixture was slowly poured into water (25 mL) with vigorous stirring. Solid material separated was filtered off, and washed with cold water (20 mL), followed by n-hexane and dried to obtain 4 as a off white solid (0.4 g, 68%).

MS(ESI) m/z: 481.9 (M+1); $^1$H NMR (400 MHz, DMSO-$d_6$): δ 3.30 (s, 6H); 3.53 (br s, 2H); 4.62 (br s, 1H); 5.56 (s, 2H); 7.58-7.70 (m, 4H); 8.06 (s, 1H); 8.41 (s, 1H); 13.30 (br s, 1H).

Step 3: 2-[1-[[3-(trifluoromethyl)phenyl]methyl]pyrazol-4-yl]-1,4-dihydroimidazo[2,1-f]purin-5-one
(5)

A mixture of 4 (0.1 g, 0.20 mmol) in conc. $H_2SO_4$ (0.033 mL, 0.60 mmol) was stirred at 70° C. for 16 h. Reaction completion was confirmed by TLC, then cooled to room temperature and the reaction mixture was slowly poured into water (25 mL) with vigorous stirring. Solid material separated was filtered off, and washed with cold water (20 mL), followed by n-hexane and dried to obtain 5 as white solid (0.05 g, 60%)

MS(ESI) m/z: 400.2 (M+1); $^1$H NMR (400 MHz, DMSO-$d_6$): δ 5.53 (s, 2H), 7.31 (d, J=1.6 Hz, 1H); 7.59-7.64 (m, 2H), 7.69-7.71 (m, 2H), 7.73 (d, J=1.2 Hz, 1H), 8.08 (s, 1H), 8.44 (s, 1H), 12.40 (s, 1H), 13.60 (s, 1H).

Step 4: 2-[1-[[3-(trifluoromethyl)phenyl]methyl]pyrazol-4-yl]-1-(2-trimethylsilylethoxymethyl)-4H-imidazo[2,1-f]purin-5-one (6)

To a solution of 5 (1.5 g, 3.75 mmol) in DMF (15 mL) was added $K_2CO_3$ (1.55 g, 11.27 mmol), and 2-(chloromethoxy) ethyl-trimethyl-silane (4 mL, 22.55 mmol). The mixture was stirred at room temperature for 16 h. Reaction completion was confirmed by TLC then dissolved in water (100 mL), and the mixture was extracted with ethyl acetate (3×100 mL). The combined organic layers were washed with brine (100 mL), dried over $Na_2SO_4$ and concentrated under vacuo to obtain a crude product (1.5 g).

MS(ESI) m/z: 530.2 (M+1); $^1$H NMR: Not recorded

Step 5: 4-propyl-2-[1-[[3-(trifluoromethyl)phenyl]methyl]pyrazol-4-yl]-1-(2-trimethylsilylethoxymethyl)imidazo[2,1-f]purin-5-one (7)

To a solution 6 (1.5 g, 0.605 mmol) in DMF (15 mL) was added potassium carbonate (0.39 g, 3.83 mmol) and n-propyliodide (0.28 g, 2.83 mmol). The mixture was stirred at 80° C. for 16 hours. Reaction completion was confirmed by TLC then dissolved in water (100 mL), and the mixture was extracted with ethyl acetate (3×100 mL). The combined organic layers were washed with brine (100 mL), dried over $Na_2SO_4$ and concentrated under vacuo to obtain a crude product. The residue was purified by column chromatography using 30-35% ethyl acetate in hexane as a mobile phase to obtain the title compound 7 (0.5 g).

MS(ESI) m/z: 572.0 (M+1); $^1$H NMR: Not recorded

Step 6: 4-propyl-2-[1-[[3-(trifluoromethyl)phenyl]methyl]pyrazol-4-yl]-1H-imidazo[2,1-f]purin-5-one
(8)

A solution of 7 (0.5 g, 0.87 mmol) in ethanol:2N HCl (30 mL) was heated at 80° C. for 16 hours. Reaction completion was confirmed by TLC then cooled to room temperature and concentrated under vacuo to obtain a crude product. The residue was basified by aqueous $NaHCO_3$ solution up to PH (7-8) then extracted with ethyl acetate (3×100 mL). The combined organic layers were washed with brine (100 mL), dried over $Na_2SO_4$ and concentrated under vacuo to obtain a crude product. The residue was purified by column chromatography using 2-4% methanol in DCM as a mobile phase to obtain the title compound 8 as a off white solid (0.012 g, 8%).

MS(ESI) m/z: 442.2 (M+1); $^1$H NMR (400 MHz, DMSO-$d_6$): δ 0.92 (t, J=7.2 Hz, 3H); 1.81 (q, J=6.8 Hz, 2H); 4.18 (t, J=7.2 Hz, 2H); 5.53 (s, 2H); 7.33 (d, J=1.6 Hz, 1H); 7.60-7.70 (m, 4H); 7.76 (d, J=1.2 Hz, 1H); 8.11 (s, 1H); 8.51 (s, 1H); 13.80 (br s, 1H).

The following compounds can also be prepared according to Schemes 1-5 or in the same manner as in the above-mentioned examples 2-[1-(2-furylmethyl)pyrazol-4-yl]-5-propyl-3H-imidazo[2,1-b]purin-4-one (III), 5-propyl-2-[1-(2-thienylmethyl)pyrazol-4-yl]-3H-imidazo[2,1-b]purin-4-one (IV), 2-[1-(oxazol-2-ylmethyl)pyrazol-4-yl]-5-propyl-3H-imidazo[2,1-b]purin-4-one (V), 2-[1-(isoxazol-5-ylmethyl)pyrazol-4-yl]-5-propyl-3H-imidazo[2,1-b]purin-4-one (VI), 2-[1-1[(5-methyl-2-thienyl)methyl]pyrazol-4-yl]-5-propyl-3H-imidazo[2,1-b]purin-4-one (VII), 2-[1-[(3,5-difluorophenyl)methyl]pyrazol-4-yl]-5-propyl-3H-imidazo[2,1-b]purin-4-one (VIII), 5-propyl-2-[1-(4-pyridylmethyl)pyrazol-4-yl]-3H-imidazo[2,1-b]purin-4-one (IX), 5-propyl-2-[1-(3-pyridylmethyl)pyrazol-4-yl]-3H-imidazo[2,1-b]purin-4-one (X), 5-propyl-2-[1-(2-pyridylmethyl)pyrazol-4-yl]-3H-imidazo[2,1-b]purin-4-one (XI), 5-propyl-2-[1-(pyrimidin-5-ylmethyl)pyrazol-4-yl]-3H-imidazo[2,1-b]purin-4-one (XII), 5-propyl-2-[1-(pyridazin-4-ylmethyl)pyrazol-4-yl]-3H-imidazo[2,1-b]purin-4-one (XIII), 2-[1-[(1-oxoisoindolin-5-yl)methyl]pyrazol-4-yl]-5-propyl-3H-imidazo[2,1-b]purin-4-one (XIV), 2-[1-[(2-methyl-1-oxo-isoindolin-5-yl)methyl]pyrazol-4-yl]-5-propyl-3H-imidazo[2,1-b]purin-4-one (XV), 2-[1-[(1-oxo-3,4-dihydro-2H-isoquinolin-6-yl)methyl]pyrazol-4-yl]-5-propyl-3H-imidazo[2,1-b]purin-4-one (XVI), 2-[1-[(2-oxo-3,4-dihydro-1H-quinolin-6-yl)methyl]pyrazol-4-yl]-5-propyl-3H-imidazo[2,1-b]purin-4-one (XVII), 5-propyl-2-[1-(quinoxalin-6-ylmethyl)pyrazol-4-yl]-3H-imidazo[2,1-b]purin-4-one (XVIII), 2-[1-(2-naphthylmethyl)pyrazol-4-yl]-5-propyl-3H-imidazo[2,1-b]purin-4-one (XIX), 2-[1-[[3-(azetidin-3-yl)phenyl]methyl]pyrazol-4-yl]-5-propyl-3H-imidazo[2,1-b]purin-4-one (XX), 2-[1-[[3-(2-methoxyethoxy)phenyl]methyl]pyrazol-4-yl]-5-propyl-3H-imidazo[2,1-b]purin-4-one (XXI), 2-[1-[[4-(2-methoxyethoxy)phenyl]methyl]pyrazol-4-yl]-5-propyl-3H-imidazo[2,1-b]purin-4-one (XXII), 5-propyl-2-[1-[3-[3-(trifluoromethyl)phenyl]prop-2-ynyl]pyrazol-4-yl]-3H-imidazo[2,1-b]purin-4-one (XXIII), 2-[1-[3-(3-fluorophenyl)prop-2-ynyl]pyrazol-4-yl]-5-propyl-3H-imidazo[2,1-b]purin-4-one (XXIV), 2-[1-[3-(4-fluorophenyl)prop-2-ynyl]pyrazol-4-yl]-5-propyl-3H-imidazo[2,1-b]purin-4-one (XXV), 5-propyl-2-[1-[3-[4-(trifluoromethyl)phenyl]prop-2-ynyl]pyrazol-4-yl]-3H-imidazo[2,1-b]purin-4-one (XXVI), 2-[1-[[1-(3-fluorophenyl)-5-oxo-pyrrolidin-3-yl]methyl]pyrazol-4-yl]-5-propyl-3H-imidazo[2,1-b]purin-4-one (XXVII), 2-[1-[[1-(m-tolyl)-5-oxo-pyrrolidin-3-yl]methyl]pyrazol-4-yl]-5-propyl-3H-imidazo[2,1-b]purin-4-one (XXVIII), 2-[1-[(3-chloro-5-fluoro-phenyl)methyl]pyrazol-4-yl]-5-propyl-3H-imidazo[2,1-b]purin-4-one (XXIX), 2-[[4-(4-oxo-5-propyl-3H-imidazo[2,1-b]purin-2-yl)pyrazol-1-yl]methyl]benzonitrile (XXX), 2-[1-[(2-fluorophenyl)methyl]pyrazol-4-yl]-5-propyl-3H-imidazo[2,1-b]purin-4-one (XXXI), 4-[[4-(4-oxo-5-propyl-3H-imidazo[2,1-b]purin-2-yl)pyrazol-1-yl]methyl]benzonitrile (XXXII), 2-[1-[[3-(4-methylpiperazin-1-yl)phenyl]methyl]pyrazol-4-yl]-5-propyl-3H-imidazo[2,1-b]purin-4-one (XXXIII), 2-[1-[1-(3-fluorophenyl)ethyl]pyrazol-4-yl]-5-propyl-3H-imidazo[2,1-b]purin-4-one (XXXIV), 2-[1-[(4-isopropylphenyl)methyl]pyrazol-4-yl]-5-propyl-3H-imidazo[2,1-b]purin-4-one (XXXV), 5-propyl-2-[1-(2,2,2-trifluoroethyl)pyrazol-4-yl]-3H-imidazo[2,1-b]purin-4-one (XXXVI), 2-[1-(2-aminoethyl)pyrazol-4-yl]-5-propyl-3H-imidazo[2,1-b]purin-4-one (XXXVII), 5-propyl-2-(1-tetrahydropyran-4-ylpyrazol-4-yl)-3H-imidazo[2,1-b]purin-4-one (XXXVIII), 2-(1-cyclopentylpyrazol-4-yl)-5-propyl-3H-imidazo[2,1-b]purin-4-one (XXXIX), 7-methyl-5-propyl-2-[1-[[3-(trifluoromethyl)phenyl]methyl]pyrazol-4-yl]-3H-imidazo[2,1-b]purin-4-one (XL), 8-methyl-5-propyl-2-[1-[[3-(trifluoromethyl)phenyl]methyl]pyrazol-4-yl]-3H-imidazo[2,1-b]purin-4-one (XLI), 7-methyl-5-propyl-2-(1-propylpyrazol-4-yl)-3H-imidazo[2,1-b]purin-4-one (XLII), 2-(1-ethylpyrazol-4-yl)-7-methyl-5-propyl-3H-imidazo[2,1-b]purin-4-one (XLIII), 7-methyl-2-(1-methylpyrazol-4-yl)-5-propyl-3H-imidazo[2,1-b]purin-4-one (XlV), 5-propyl-2-(1-propylpyrazol-4-yl)-7-(trifluoromethyl)-3H-imidazo[2,1-b]purin-4-one (XLV), 5-propyl-7-(trifluoromethyl)-2-[1-[[3-(trifluoromethyl)phenyl]methyl]pyrazol-4-yl]-3H-imidazo[2,1-b]purin-4-one (XLVI), 2-[1-(m-tolylmethyl)pyrazol-4-yl]-4-propyl-1H-imidazo[2,1-f]purin-5-one (XLVII), 2-[1-[(3-fluorophenyl)methyl]pyrazol-4-yl]-4-propyl-1H-imidazo[2,1-f]purin-5-one (XLVIII), 3-[[4-(5-oxo-4-propyl-1H-imidazo[2,1-f]purin-2-yl)pyrazol-1-yl]methyl]benzonitrile (XLIX), 3-[[4-(4-ethyl-5-oxo-1H-imidazo[2,1-f]purin-2-yl)pyrazol-1-yl]methyl]benzonitrile (L), 3-[1-methyl-1-[4-(4-oxo-5-propyl-3H-imidazo[2,1-b]purin-2-yl)pyrazol-1-yl]ethyl]benzonitrile (LI), 5-propyl-2-[3-[[3-(trifluoromethyl)phenyl]methoxy]isoxazol-5-yl]-3H-imidazo[2,1-b]purin-4-one (LII).

The compounds of the disclosure may be prepared by a variety of methods, including standard synthetic chemistry. Any previously defined variable will continue to have the previously defined meaning unless otherwise indicated. Illustrative general synthetic methods are set out in the schemes and can be readily adapted to prepare other compounds of the disclosure.

Example 4

Biological Assay
Radioligand Binding for $A_{2A}$ Adenosine Receptor

Human $A_{2A}$ adenosine receptor cDNA was stably transfected into HEK-293 cells. HEK-A2B cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM (Tris pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4) supplemented with 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 2 nM [$^3$H]-ZM-241385 with various concentrations of test compounds and 5 µg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non-specific binding was determined in presence of 200 µM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.
Radioligand Binding for $A_{2B}$ Adenosine Receptor Human $A_{2B}$ adenosine receptor cDNA was stably transfected into HEK-293 cells. HEK-A2B cells were harvested by trypsinization with 0.25% Trypsin-EDTA (Sigma) and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 second each and centrifuged at 1000×g for 10 minutes at 4° C. The pellet was discarded, and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 1.6 nM [$^3$H]-MRS-1754 with various concentrations of test compounds and 10 μg membrane protein in Reaction buffer (50 mM Tris pH 6.5, 5 mM MgCl$_2$, 1 mM EDTA) supplemented with 1 U/ml Adenosine deaminase. The assay reactions were incubated for 90 minutes at room temperature and stopped by filtration using 96 well-plate harvester (Molecular Devices) and washed four times with ice cold 50 mM Tris (pH 7.4). Non-specific binding was determined in presence of 200 μM NECA. Radioligand binding was read at Liquid scintillation counter (Perkin Elmer) and the affinities of compounds (i.e. K$_i$ values) were calculated using GraphPad software.

Compounds tested had micromolar to nanomolar activity.

cAMP Assay for Adenosine Receptor.

The functional activity of test compounds on A$_{2A}$ and A$_{2B}$ adenosine receptors and selectivity over A$_1$ adenosine was determined using HTRF based cAMP assay (Cisbio). Briefly, overnight seeded cultures (HEK-A1, HEK-A$_{2A}$, HEK-A$_{2B}$) were treated with 1 U/ml ADA for 90 minutes at 37° C. and 5% CO$_2$. Cell suspensions were treated with increasing concentrations of test compounds for 15 minutes followed by treatment with agonists for 15 minutes (1 nM CPA for HEK-A1 and 70 nM NECA for HEK-A$_{2B}$) or 30 min (10 nM CGS-21680 for HEK-A$_{2A}$) at room temperature with continuous mixing in incomplete DMEM supplemented with 1 U/ml ADA. Rolipram (20 μM) was included in the assay for A$_1$ and A$_{2A}$ adenosine receptors. For functional activity of HEK-A$_1$, cell suspensions were further treated with forskolin for 30 minutes at room temperature with constant mixing. cAMP levels were quantified using a Flex Station III (Molecular Devices) at an excitation maximum of 313 nm and emission maxima of 620 nm and 665 nm. Data was analyzed using GraphPad Prism to generate IC$_{50}$ and K$_i$. The biological activity data is provided in the Table below. <10 nM are represented as ++++, 10-30 nM as +++, 30-100 nM ++ and the K$_i$ value >100 nM as +.

| Ex. No. | A2A Functional K$_i$ nM | A2B Functional K$_i$ nM |
| --- | --- | --- |
| A1 | ++++ | ++++ |
| A2 | ND | ND |
| A3 | +++ | ++++ |
| A4 | ND | ND |
| A5 | ++ | ND |
| A6 | + | ND |
| A7 | ++++ | ++++ |
| B2 | +++ | ++++ |
| B3 | +++ | ++++ |
| B6 | ++ | ++++ |
| B7 | ++++ | ++++ |
| B8 | +++ | ++++ |
| B9 | +++ | ++++ |
| B10 | +++ | ++++ |
| B11 | + | +++ |
| B12 | + | +++ |
| B13 | ++++ | ++++ |
| B14 | + | ++++ |
| B16 | ++++ | ++++ |
| B17 | +++ | ++++ |
| B19 | ++++ | ++++ |
| B20 | ++++ | ++++ |
| C2 | ++ | ++++ |
| D1 | ++ | ++++ |
| E1 | ++++ | ++++ |
| F1 | +++ | ++++ |
| G1 | +++ | ++++ |
| H1 | + | ++ |
| J1 | ++ | ++ |
| N3 | ++++ | ++++ |
| N4 | ++++ | ++++ |
| N5 | ++ | +++ |

ND = NOT DETERMINED

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A compound of Formula I, or its stereoisomers, pharmaceutically acceptable salts, tautomers, racemic mixtures, optically active forms and thereof,

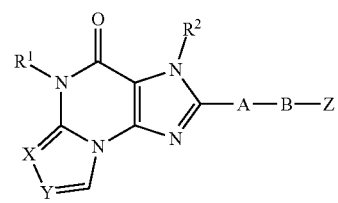

Formula I wherein wherein R$^1$ is selected from alkyl, cycloalkyl, cycloalkylalkyl, aryl, arylalkyl, heterocyclyl, heterocyclylalkyl, heteroaryl, or heteroarylalkyl;

R$^2$ is selected from hydrogen, alkyl, alkenyl, alkynyl, alkoxyalkyl, cycloalkyl, cycloalkylalkyl, aryl, arylalkyl, heteroaryl, or heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxyl, alkoxy, halogen, haloalkyl, haloalkoxy, amino, substituted amino, cyano or —S(O)$_p$R$^d$;

X and Y are independently selected from CR' or N, wherein R' is selected from hydrogen, halogen, alkyl and haloalkyl;

A is selected from an arylene or an optionally substituted heteroarylene;

B is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^cR^c$, —$NR^cS(O)_2R^c$ or —$S(O)_pR^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —$S(O)_2NR^bR^b$, —$NR^bS(O)_2R^b$ or —$S(O)_pR^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —$S(O)_pR^d$;

$R^a$ is selected from hydrogen, or alkyl;

$R^b$ is selected from hydrogen, alkyl, acyl, carboxyalkyl, carbonylamino, cycloalkyl, cycloalkylalkyl, aryl, arylalkyl, heteroaryl, heteroarylalkyl, heterocyclyl, or heterocyclylalkyl;

$R^c$ is selected from hydrogen, alkyl, aryl, heteroaryl, or heterocyclyl;

$R^d$ is selected from alkyl, cycloalkyl, aryl, heterocyclyl, or heteroaryl; and p is 0, 1, or 2.

2. The compound of Formula I as claimed in claim 1, wherein wherein $R^1$ is selected from alkyl, cycloalkyl, aryl, arylalkyl, heterocyclyl, heteroaryl, or heteroarylalkyl;

$R^2$ is selected from hydrogen, alkyl, alkenyl, alkynyl, cycloalkyl, aryl, arylalkyl, heteroaryl, or heteroarylalkyl, wherein alkyl, alkenyl, alkynyl, cycloalkyl, aryl, arylalkyl, heteroaryl, and heteroarylalkyl are unsubstituted or substituted independently with alkyl, alkenyl, alkynyl, cycloalkyl, cycloalkenyl, acyl, acylamino, amino, monoalkylamino, dialkylamino, arylamino, cycloalkylamino, heteroarylamino, heterocyclylamino, aminocarbonyl, azido, cyano, halogen, hydroxy, hydroxyalkyl, keto, thiocarbonyl, carboxy, alkylcarboxy, carboxyalkyl, —$SO_3H$, aryl, cycloalkyloxy, heteroaryl, aminocarbonylamino, heterocyclyl, heterocyclyloxy, hydroxyamino, nitro, $S(O)_2NR^cR^c$, —$NR^cS(O)_2R^c$ or —$S(O)_pR^d$;

wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —$S(O)_pR^d$;

X and Y are independently selected from CR' or N, wherein R' is selected from hydrogen, halogen, or alkyl;

A is selected from an arylene or an optionally substituted heteroarylene;

B is selected from a bond, $(C_1-C_6)$alkylene, or $(C_2-C_6)$alkynylene group, wherein 1 to 3 methylene groups are optionally replaced by groups independently selected from O, —$S(O)_p$—, or —$C(O)$—;

wherein alkylene, and alkynylene are unsubstituted or substituted independently with alkyl, alkenyl, alkynyl, alkoxy, cycloalkyl, cycloalkenyl, acyl, acyloxy, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, heteroaryloxy, heterocyclyl, heterocyclyloxy, hydroxyamino, nitro, $S(O)_2NR^cR^c$, or —$S(O)_pR^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, cyano, halogen, hydroxy, hydroxyalkyl, keto, thiocarbonyl, carboxy, alkylcarboxy, carboxyalkyl, carboxyalkyloxy, alkylcarboxyalkyloxy, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, —$S(O)_2NR^bR^b$, —$NR^bS(O)_2R^b$ or —$S(O)_pR^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;

$R^a$ is selected from hydrogen, or alkyl;

$R^b$ is selected from hydrogen, alkyl, acyl, carboxyalkyl, carbonylamino, cycloalkyl, cycloalkylalkyl, aryl, arylalkyl, heteroaryl, heteroarylalkyl, heterocyclyl, or heterocyclylalkyl;

$R^c$ is selected from hydrogen, alkyl, aryl, heteroaryl, or heterocyclyl;

$R^d$ is selected from alkyl, cycloalkyl, aryl, heterocyclyl, or heteroaryl; and p is 0, 1, or 2.

3. The compound of Formula I as claimed in claim 1, wherein $R^1$ is selected from alkyl, cycloalkyl, aryl, or arylalkyl, $R^2$ is selected from hydrogen, alkyl, alkenyl, alkynyl, cycloalkyl, or aryl, wherein alkyl, alkenyl, alkynyl, cycloalkyl, aryl, are unsubstituted or substituted independently with alkyl, alkenyl, alkynyl, cycloalkyl, cycloalkenyl, acyl, acylamino, amino, monoalkylamino, dialkylamino, arylamino, cycloalkylamino, heteroarylamino, heterocyclylamino, aminocarbonyl, azido, cyano, halogen, hydroxy, hydroxyalkyl, keto, thiocarbonyl, carboxy, alkylcarboxy, carboxyalkyl, —$SO_3H$, aryl, cycloalkyloxy, heteroaryl, aminocarbonylamino, heterocyclyl, heterocyclyloxy, hydroxyamino, nitro, $S(O)_2NR^cR^c$, —$NR^cS(O)_2R^c$ or —$S(O)_pR^d$;

wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —$S(O)_pR^d$;

X and Y are independently selected from CR' or N, wherein R' is selected from hydrogen, halogen, or alkyl;

A is selected from an arylene or an optionally substituted heteroarylene;

B is selected from a bond, $(C_1-C_6)$alkylene, or $(C_2-C_6)$ alkynylene group, wherein 1 to 3 methylene groups are optionally replaced by groups independently selected from O, —S(O)$_p$—, or —C(O)—;

wherein alkylene, and alkynylene are unsubstituted or substituted independently with alkyl, alkenyl, alkynyl, alkoxy, cycloalkyl, cycloalkenyl, acyl, acyloxy, azido, cyano, halogen; hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, heteroaryloxy, heterocyclyl, heterocyclyloxy, hydroxyamino, nitro, S(O)$_2$NR$^c$R$^c$, or —S(O)$_p$R$^d$;

Z is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, cyano, halogen, hydroxy, hydroxyalkyl, keto, thiocarbonyl, carboxy, alkylcarboxy, carboxyalkyl, carboxyalkyloxy, alkylcarboxyalkyloxy, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;

R$^a$ is selected from hydrogen, or alkyl;

R$^b$ is selected from hydrogen, alkyl, aryl, arylalkyl, heteroaryl, or heterocyclylalkyl;

R$^c$ is selected from hydrogen, alkyl, aryl, heteroaryl, or heterocyclyl;

R$^d$ is selected from alkyl, cycloalkyl, aryl, heterocyclyl, or heteroaryl; and p is 1, or 2.

4. The compound of Formula I as claimed in claim 1, wherein R$^1$ is selected from alkyl;

R$^2$ is selected from hydrogen, or alkyl, wherein alkyl, is unsubstituted or substituted independently with alkyl, alkenyl, alkynyl, cycloalkyl, cycloalkenyl, acyl, acylamino, amino, monoalkylamino, dialkylamino, cycloalkylamino, heteroaryl, aminocarbonylamino, heterocyclyl, heterocyclyloxy, hydroxyamino, nitro, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;

X and Y are independently selected from CR' or N, wherein R' is selected from hydrogen, halogen, or alkyl;

A is selected from an arylene or an optionally substituted heteroarylene;

B is selected from a bond, $(C_1-C_6)$alkylene, or $(C_2-C_6)$ alkynylene group, wherein 1 to 3 methylene groups are optionally replaced by groups independently selected from O, —S(O)$_p$—, or —C(O)—;

wherein alkylene, and alkynylene are unsubstituted or substituted independently with alkyl, alkenyl, alkynyl, alkoxy, cycloalkyl, cycloalkenyl, acyl, acyloxy, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, heteroaryloxy, heterocyclyl, heterocyclyloxy, hydroxyamino, nitro, S(O)$_2$NR$^c$R$^c$, or —S(O)$_p$R$^d$;

Z is selected from hydrogen, heterocyclyl, aryl or heteroaryl;

wherein heterocyclyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, halogen, hydroxy, hydroxyalkyl, keto, thiocarbonyl, carboxy, aryl, arylalkyl, aryloxy, cycloalkyloxy, heteroaryl, heteroarylalkyl, heteroaryloxy, heterocyclyl, heterocyclylalkyl, heterocyclyloxy, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino;

R$^a$ is selected from hydrogen, or alkyl;

R$^b$ is selected from hydrogen, alkyl, aryl, arylalkyl, heteroaryl, or heterocyclylalkyl;

R$^c$ is selected from hydrogen, alkyl, aryl, heteroaryl, or heterocyclyl;

R$^d$ is selected from alkyl, cycloalkyl, aryl, heterocyclyl, or heteroaryl; and p is 0, 1, or 2.

5. The compound of Formula as claimed in claim 1, wherein the compound of Formula I is selected from the group consisting of:

5-propyl-2-[1-[[3-(trifluoromethyl)phenyl]methyl]pyrazol-4-yl]-3H-imidazo[2,1-b]purin-4-one (A1), 2-(1-benzylpyrazol-4-yl)-5-propyl-3H-imidazo[2,1-b]purin-4-one (A2), 5-methyl-2-[1-[[3-(trifluoromethyl)phenyl]methyl]pyrazol-4-yl]-3H-imidazo[2,1-b]purin-4-one (A3), 5-propyl-2-[1-[2-[3-(trifluoromethyl)phenyl]ethyl]pyrazol-4-yl]-3H-imidazo[2,1-b]purin-4-one (A4), 2-[1-[2-(3-fluorophenyl)ethyl]pyrazol-4-yl]-5-propyl-3H-imidazo[2,1-b]purin-4-one (A5), 2-(1-methylpyrazol-4-yl)-5-propyl-3H-imidazo [2, 1-b]purin-4-one (A6), 2-[1-(1,1-dimethylpropyl)pyrazol-4-yl]-5-propyl-3H-imidazo[2,1-b]purin-4-one (A7), N-isopropyl-3-[3-[4-(4-oxo-5-propyl-3H-imidazo[2,1-b]purin-2-yl)pyrazol-1-yl]prop-1-ynyl]benzamide (B1), Ethyl 3-[3-[4-(4-oxo-5-propyl-3H-imidazo[2,1-b]purin-2-yl)pyrazol-1-yl]prop-1-ynyl]benzoate (B2), 5-propyl-2-[1-[3-[3-(trifluoromethoxy)phenyl]prop-2-ynyl]pyrazol-4-yl]-3H-imidazo[2,1-b]purin-4-one (B3), Ethyl 4-methyl-3-[3-[4-(4-oxo-5-propyl-3H-imidazo[2,1-b]purin-2-yl)pyrazol-1-yl]prop-1-ynyl]benzoate (B6), 3-[[4-(4-oxo-5-propyl-3H-imidazo[2,1-b]purin-2-yl)
pyrazol-1-yl]methyl]benzonitrile (B7),
2-(1-isopropylpyrazol-4-yl)-5-propyl-3H-imidazo[2,1-b]
purin-4-one (B8),
2-(1-butylpyrazol-4-yl)-5-propyl-3H-imidazo[2,1-b]purin-4-one (B9),
2-(1-ethylpyrazol-4-yl)-5-propyl-3H-imidazo[2,1-b]purin-4-one (B10),
2-[1-(2-methoxyethyl)pyrazol-4-yl]-5-propyl-3H-imidazo[2,1-b]purin-4-one (B11),
2-[1-(2-dimethylaminoethyl)pyrazol-4-yl]-5-propyl-3H-imidazo[2,1-b]purin-4-one (B12),
5-propyl-2-(1-propylpyrazol-4-yl)-3H-imidazo[2,1-b]purin-4-one (B13),
N,N-dimethyl-2-[4-(4-oxo-5-propyl-3H-imidazo[2,1-b]purin-2-yl)pyrazol-1-yl]acetamide (B14),
2-[1-(2-morpholinoethyl)pyrazol-4-yl]-5-propyl-3H-imidazo[2,1-b]purin-4-one (B15),
2-[1-(cyclobutylmethyl)pyrazol-4-yl]-5-propyl-3H-imidazo[2,1-b]purin-4-one (B16),
2-(1-isobutylpyrazol-4-yl)-5-propyl-3H-imidazo[2,1-b]purin-4-one (B17),
2-[1-(cyclopropylmethyl)pyrazol-4-yl]-5-propyl-3H-imidazo[2,1-b]purin-4-one (B18),
2-[1-(2,2-dimethylpropyl)pyrazol-4-yl]-5-propyl-3H-imidazo[2,1-b]purin-4-one (B19),
5-propyl-2-(1-sec-butylpyrazol-4-yl)-3H-imidazo[2,1-b]purin-4-one (B20),
5-propyl-2-[1-(tetrahydrofuran-2-ylmethyl)pyrazol-4-yl]-3H-imidazo[2,1-b]purin-4-one (B21),
2-[1-[[5-oxo-1-[2-(trifluoromethyl)-4-pyridyl]pyrrolidin-3-yl]methyl]pyrazol-4-yl]-5-propyl-3H-imidazo[2,1-b]purin-4-one (C1),
2-[1-[[5-oxo-1-[5-(trifluoromethyl)-3-pyridyl]pyrrolidin-3-yl]methyl]pyrazol-4-yl]-5-propyl-3H-imidazo[2,1-b]purin-4-one (C2),
2-[1-[[5-oxo-1-[3-(trifluoromethyl)phenyl]pyrrolidin-3-yl]methyl]pyrazol-4-yl]-5-propyl-3H-imidazo[2,1-b]purin-4-one (C3),
2-[1-[2-(1-piperidyl)ethyl]pyrazol-4-yl]-5-propyl-3H-imidazo[2,1-b]purin-4-one (D1),
2-[1-[[3-(hydroxymethyl)phenyl]methyl]pyrazol-4-yl]-5-propyl-3H-imidazo[2,1-b]purin-4-one (E1),
2-[1-[[3-(1-hydroxy-1-methyl-ethyl)phenyl]methyl]pyrazol-4-yl]-5-propyl-3H-imidazo[2,1-b]purin-4-one (F1),
3-[[4-(4-oxo-5-propyl-3H-imidazo[2,1-b]purin-2-yl)pyrazol-1-yl]methyl]benzoic acid (G1),
2-[4-(4-oxo-5-propyl-3H-imidazo[2,1-b]purin-2-yl)pyrazol-1-yl]acetic acid (H1),
2-[1-(2-hydroxy-2-methyl-propyl)pyrazol-4-yl]-5-propyl-3H-imidazo[2,1-b]purin-4-one (I1),
2-[1-(2,3-dihydroxypropyl)pyrazol-4-yl]-5-propyl-3H-imidazo[2,1-b]purin-4-one (J1),
2-(3,4-dimethoxyphenyl)-5-propyl-3H-imidazo[2,1-b]purin-4-one (K1),
5-propyl-2-[3-(trifluoromethyl)phenyl]-3H-imidazo[2,1-b]purin-4-one (K2),
2-[1-[(3-fluorophenyl)methyl]pyrazol-4-yl]-5-propyl-3H-imidazo[2,1-b]purin-4-one (K3),
2-[1-[(3-methoxyphenyl)methyl]pyrazol-4-yl]-5-propyl-3H-imidazo[2,1-b]purin-4-one (K4),
2-[4-[2-(1-piperidyl)ethoxy]phenyl]-5-propyl-3H-imidazo[2,1-b]purin-4-one (K5),
2-(5-methoxy-2-pyridyl)-5-propyl-3H-imidazo[2,1-b]purin-4-one (K6),
2-(4-ethoxyphenyl)-5-propyl-3H-imidazo[2,1-b]purin-4-one (K7),
N-isopropyl-2-[4-(4-oxo-5-propyl-3H-imidazo[2,1-b]purin-2-yl)pyrazol-1-yl]acetamide (L1),
N-(oxetan-3-yl)-2-[4-(4-oxo-5-propyl-3H-imidazo[2,1-b]purin-2-yl)pyrazol-1-yl]acetamide (L2),
4-propyl-2-[1-[[3-(trifluoromethyl)phenyl]methyl] pyrazol-4-yl]-1H-imidazo[2,1-f]purin-5-one (II),
2-[1-(2-furylmethyl)pyrazol-4-yl]-5-propyl-3H-imidazo[2,1-b]purin-4-one

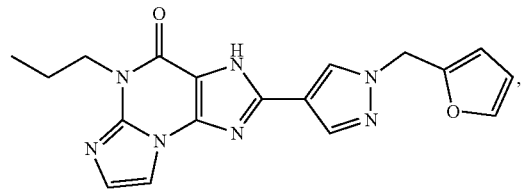

(III)

5-propyl-2-[1-(2-thienylmethyl)pyrazol-4-yl]-3H-imidazo[2,1-b]purin-4-one

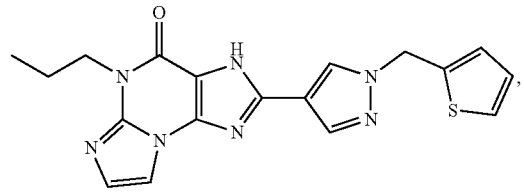

(IV)

2-[1-(oxazol-2-ylmethyl)pyrazol-4-yl]-5-propyl-3H-imidazo[2,1-b]purin-4-one

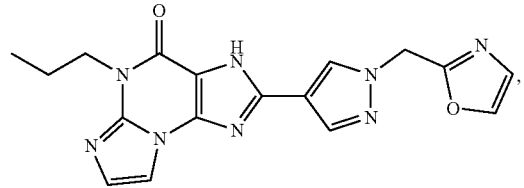

(V)

2-[1-(isoxazol-5-ylmethyl)pyrazol-4-yl]-5-propyl-3H-imidazo[2,1-b]purin-4-one

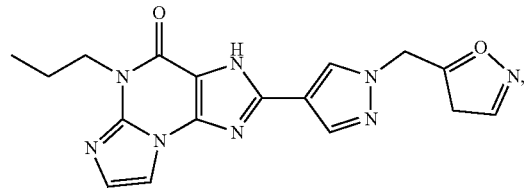

(VI)

2-[1-[(5-methyl-2-thienyl)methyl]pyrazol-4-yl]-5-pro-
pyl-3H-imidazo[2,1-b]purin-4-one (VII)

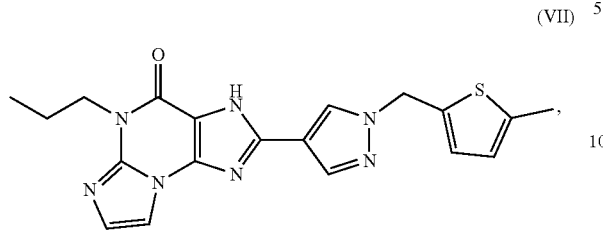

2-[1-[(3,5-difluorophenyl)methyl]pyrazol-4-yl]-5-pro-
pyl-3H-imidazo[2,1-b]purin-4-one (VIII)

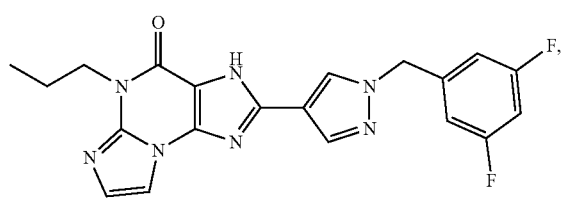

5-propyl-2-[1-(4-pyridylmethyl)pyrazol-4-yl]-3H-imi-
dazo[2,1-b]purin-4-one (IX)

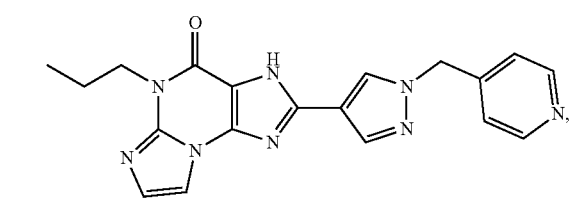

5-propyl-2-[1-(3-pyridylmethyl)pyrazol-4-yl]-3H-imi-
dazo[2,1-b]purin-4-one (X)

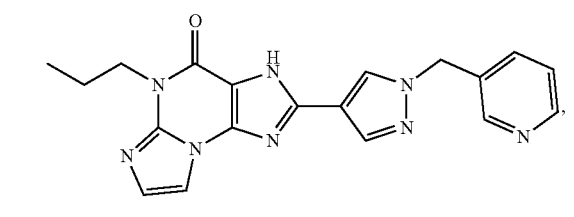

5-propyl-2-[1-(2-pyridylmethyl)pyrazol-4-yl]-3H-imi-
dazo[2,1-b]purin-4-one (XI)

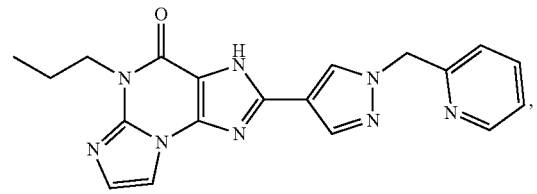

5-propyl-2-[1-(pyrimidin-5-ylmethyl)pyrazol-4-yl]-3H-
imidazo[2,1-b]purin-4-one (XII)

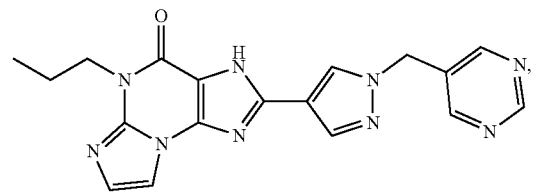

5-propyl-2-[1-(pyridazin-4-ylmethyl)pyrazol-4-yl]-3H-
imidazo[2,1-b]purin-4-one (XIII)

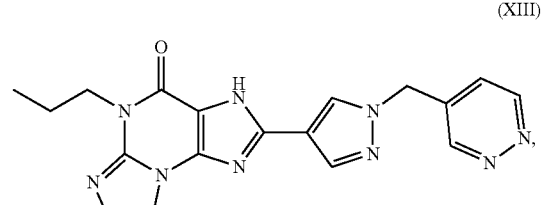

2-[1-[(1-oxoisoindolin-5-yl)methyl]pyrazol-4-yl]-5-pro-
pyl-3H-imidazo[2,1-b]purin-4-one (XIV)

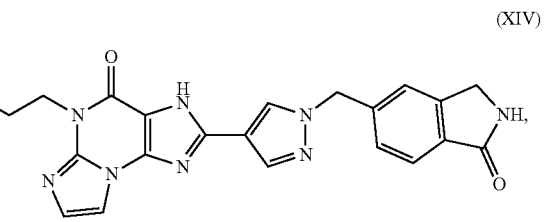

2-[1-[(2-methyl-1-oxo-isoindolin-5-yl)methyl]pyrazol-4-
yl]-5-propyl-3H-imidazo[2,1-b]purin-4-one (XV)

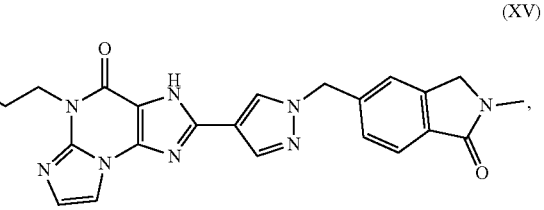

2-[1-[(1-oxo-3,4-dihydro-2H-isoquinolin-6-yl)methyl]
pyrazol-4-yl]-5-propyl-3H-imidazo[2,1-b]purin-4-one 2-[1-[[3-(azetidin-3-yl)phenyl]methyl]pyrazol-4-yl]-5-
propyl-3H-imidazo[2,1-b]purin-4-one

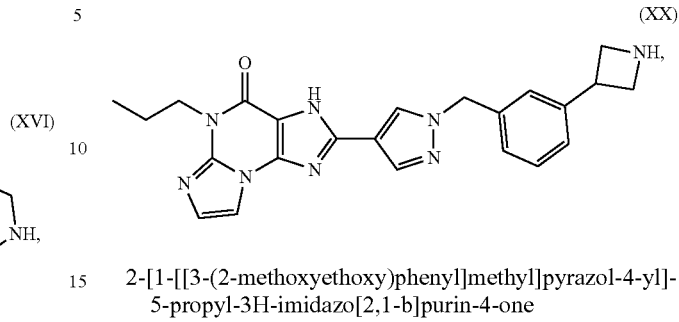

(XVI)

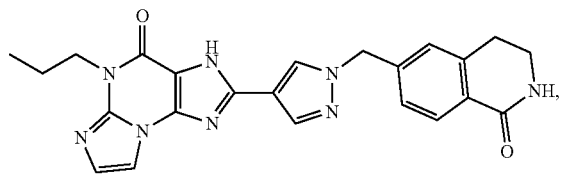

2-[1-[(2-oxo-3,4-dihydro-1H-quinolin-6-yl)methyl]pyra-
zol-4-yl]-5-propyl-3H-imidazo[2,1-b]purin-4-one 2-[1-[[3-(2-methoxyethoxy)phenyl]methyl]pyrazol-4-yl]-
5-propyl-3H-imidazo[2,1-b]purin-4-one

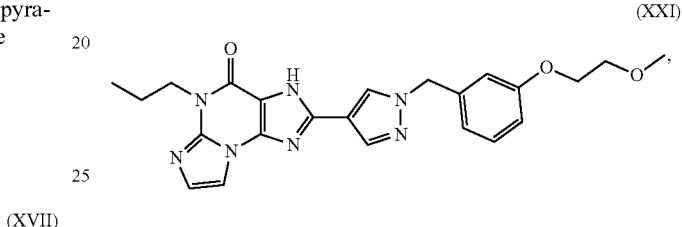

2-[1-[[4-(2-methoxyethoxy)phenyl]methyl]pyrazol-4-yl]-
5-propyl-3H-imidazo[2,1-b]purin-4-one (XVII)

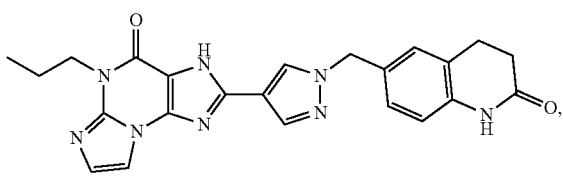

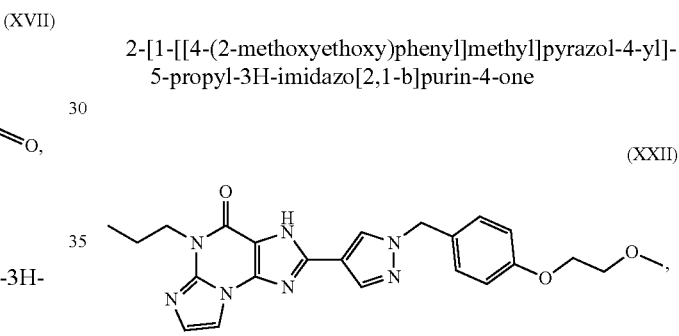

5-propyl-2-[1-(quinoxalin-6-ylmethyl)pyrazol-4-yl]-3H-
imidazo[2,1-b]purin-4-one 5-propyl-2-[1-[3-[3-(trifluoromethyl)phenyl]prop-2-
ynyl]pyrazol-4-yl]-3H-imidazo[2,1-b]purin-4-one (XVIII)

(XXIII)

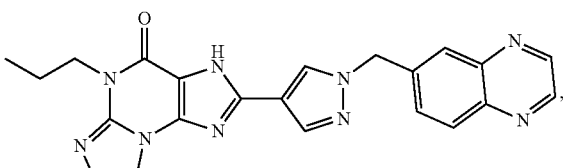

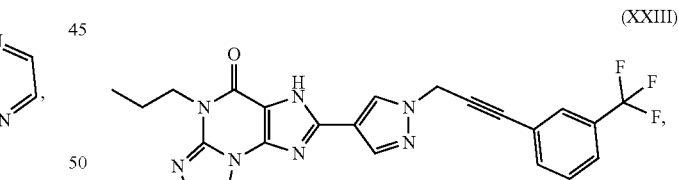

2-[1-(2-naphthylmethyl)pyrazol-4-yl]-5-propyl-3H-imi-
dazo[2,1-b]purin-4-one

2-[1-[3-(3-fluorophenyl)prop-2-ynyl]pyrazol-4-yl]-5-
propyl-3H-imidazo[2,1-b]purin-4-one (XIX)

(XXIV)

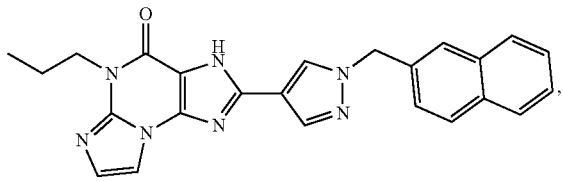

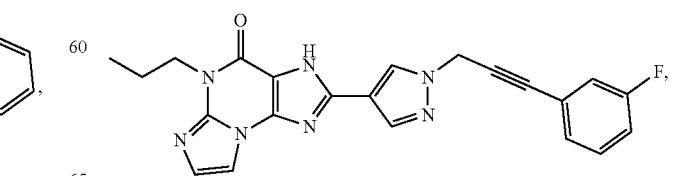

2-[1-[3-(4-fluorophenyl)prop-2-ynyl]pyrazol-4-yl]-5-propyl-3H-imidazo[2,1-b]purin-4-one (XXV)

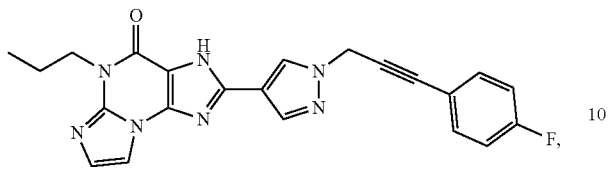

5-propyl-2-[1-[3-[4-(trifluoromethyl)phenyl]prop-2-ynyl]pyrazol-4-yl]-3H-imidazo[2,1-b]purin-4-one (XXVI)

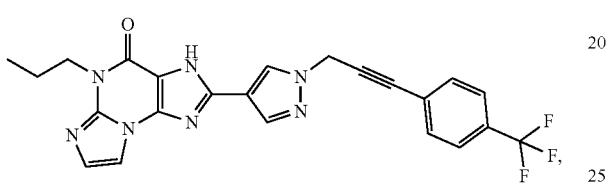

2-[1-[[1-(3-fluorophenyl)-5-oxo-pyrrolidin-3-yl]methyl]pyrazol-4-yl]-5-propyl-3H-imidazo[2,1-b]purin-4-one (XXVII)

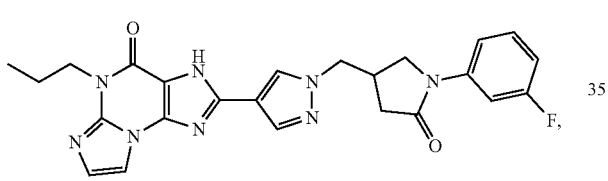

2-[1-[[1-(m-tolyl)-5-oxo-pyrrolidin-3-yl]methyl]pyrazol-4-yl]-5-propyl-3H-imidazo[2,1-b]purin-4-one (XXVIII)

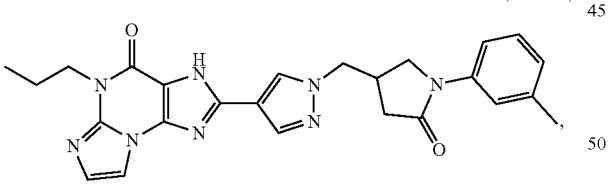

2-[1-1[(3-chloro-5-fluoro-phenyl)methyl]pyrazol-4-yl]-5-propyl-3H-imidazo[2,1-b]purin-4-one (XXIX)

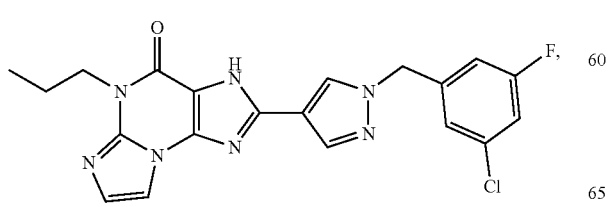

2-[[4-(4-oxo-5-propyl-3H-imidazo[2,1-b]purin-2-yl)pyrazol-1-yl]methyl]benzonitrile (XXX)

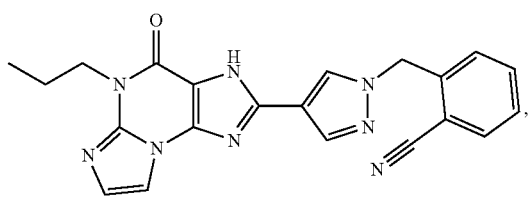

2-[1-[(2-fluorophenyl)methyl]pyrazol-4-yl]-5-propyl-3H-imidazo[2,1-b]purin-4-one (XXXI)

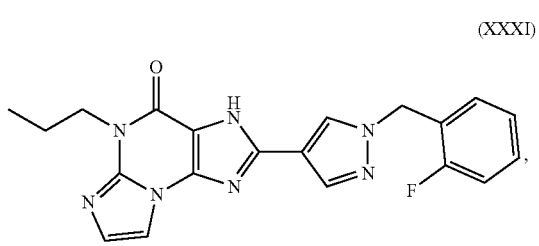 [SMILES: CCCn1c(=O)c2[nH]c(-c3cnn(Cc4ccccc4F)c3)nc2n2ccnc12]

4-[[4-(4-oxo-5-propyl-3H-imidazo[2,1-b]purin-2-yl)pyrazol-1-yl]methyl]benzonitrile (XXXII)

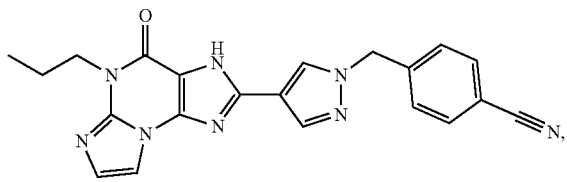

2-[1-[[3-(4-methylpiperazin-1-yl)phenyl]methyl]pyrazol-4-yl]-5-propyl-3H-imidazo[2,1-b]purin-4-one (XXXIII)

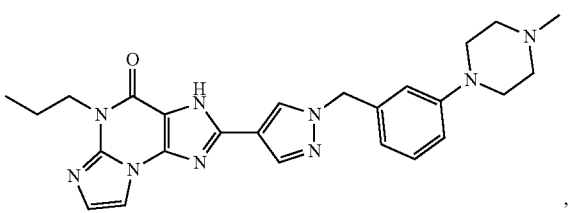

2-[1-[1-(3-fluorophenyl)ethyl]pyrazol-4-yl]-5-propyl-
3H-imidazo[2,1-b]purin-4-one 5-propyl-2-(1-tetrahydropyran-4-ylpyrazol-4-yl)-3H-imi-
dazo[2,1-b]purin-4-one

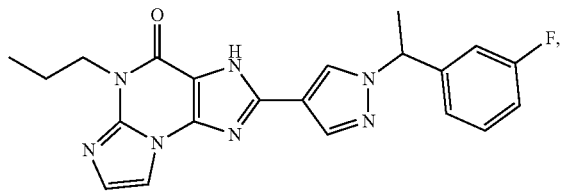

(XXXIV)

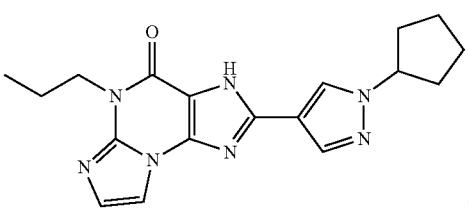

(XXXVIII)

2-[1-[(4-isopropylphenyl)methyl]pyrazol-4-yl]-5-propyl-
3H-imidazo[2,1-b]purin-4-one 2-(1-cyclopentylpyrazol-4-yl)-5-propyl-3H-imidazo[2,1-
b]purin-4-one

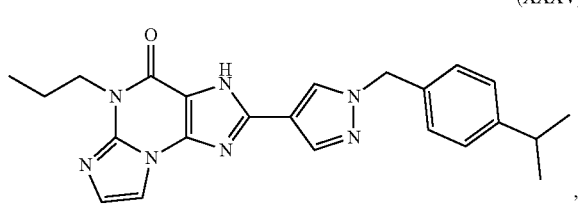

(XXXV)

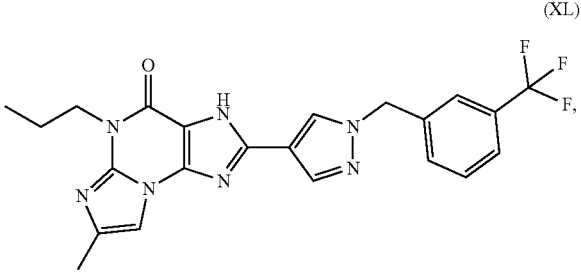 [SMILES: CCCn1c(=O)c2[nH]c(-c3cnn(Cc4cccc(C(F)(F)F)c4)c3)nc2n2cc(C)nc12]

(XXXIX)

5-propyl-2-[1-(2,2,2-trifluoroethyl)pyrazol-4-yl]-3H-imi-
dazo[2,1-b]purin-4-one 7-methyl-5-propyl-2-[1-[[3-(trifluoromethyl)phenyl]
methyl]pyrazol-4-yl]-3H-imidazo[2,1-b]purin-4-one

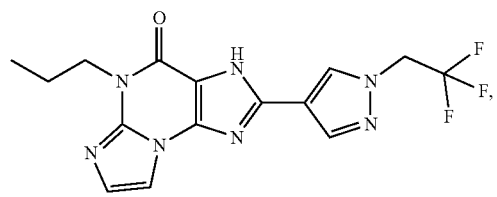

(XXXVI)

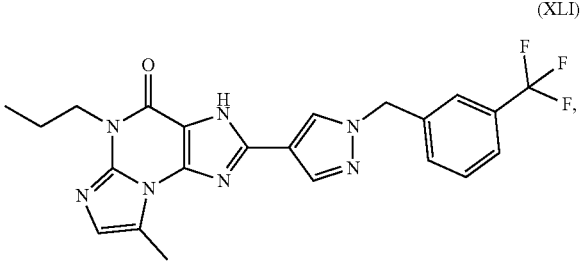 [SMILES: CCCn1c(=O)c2[nH]c(-c3cnn(Cc4cccc(C(F)(F)F)c4)c3)nc2n2c(C)cnc12]

(XL)

2-[1-(2-aminoethyl)pyrazol-4-yl]-5-propyl-3H-imidazo
[2,1-b]purin-4-one 8-methyl-5-propyl-2-[1-[[3-(trifluoromethyl)phenyl]
methyl]pyrazol-4-yl]-3H-imidazo[2,1-b]purin-4-one

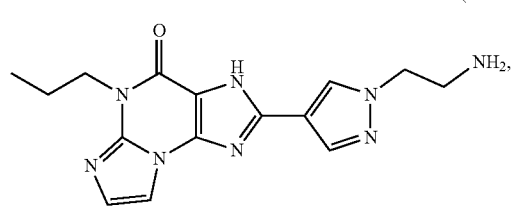

(XXXVII)

(XLI)

7-methyl-5-propyl-2-(1-propylpyrazol-4-yl)-3H-imidazo[2,1-b]purin-4-one 5-propyl-7-(trifluoromethyl)-2-[1-[[3-(trifluoromethyl)phenyl]methyl]pyrazol-4-yl]-3H-imidazo[2,1-b]purin-4-one

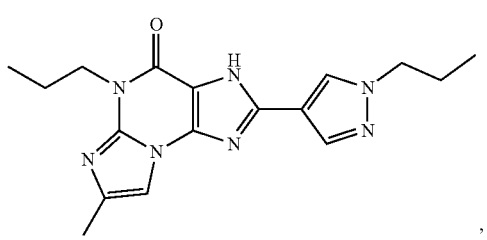

(XLII)

2-(1-ethylpyrazol-4-yl)-7-methyl-5-propyl-3H-imidazo[2,1-b]purin-4-one

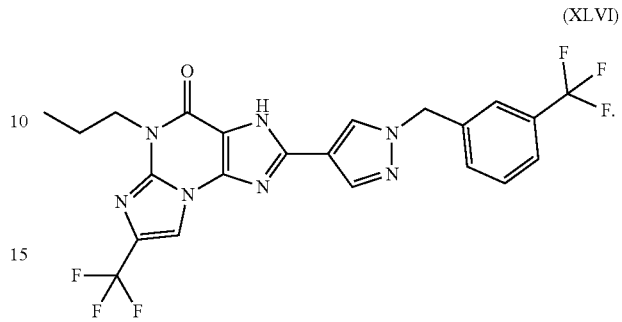

(XLVI)

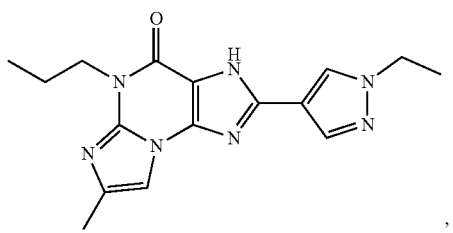

(XLIII)

7-methyl-2-(1-methylpyrazol-4-yl)-5-propyl-3H-imidazo[2,1-b]purin-4-one

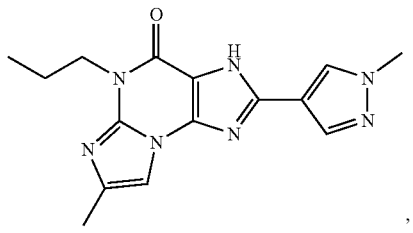

(XLIV)

5-propyl-2-(1-propylpyrazol-4-yl)-7-(trifluoromethyl)-3H-imidazo[2,1-b]purin-4-one

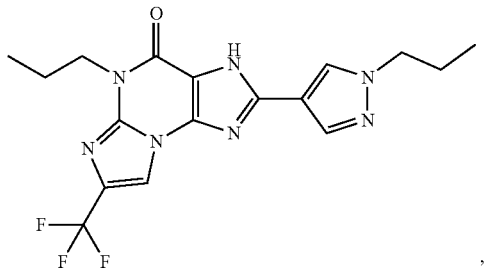

(XLV)

6. The compound of Formula I as claimed in claim 1 or its stereoisomers, pharmaceutically acceptable salts, tautomers, racemic mixtures, and optically active forms thereof for use as a medicament.

7. The compound of Formula I as claimed in claim 1 or its stereoisomers, pharmaceutically acceptable salts, tautomers, racemic mixtures, and optically active forms thereof, for use in treating conditions and diseases that are mediated by adenosine receptor (AR) activity.

8. The compound of Formula I as claimed in claim 1 or its stereoisomers, pharmaceutically acceptable salts, tautomers, racemic mixtures, and optically active forms thereof, for use in methods for treating or lessening the severity of immunotherapies or radiotherapy or chemotherapy.

9. A pharmaceutical composition comprising a compound of Formula I as claimed in claim 1 or its stereoisomers, pharmaceutically acceptable salts, tautomers, racemic mixtures, and optically active forms thereof, together with a pharmaceutically acceptable carrier, or a pharmaceutically acceptable excipient or a pharmaceutically acceptable diluent.

10. The pharmaceutical composition as claimed in claim 9, for treating or lessening the severity of immunotherapies or radiotherapy or chemotherapy.

11. A method for treatment of cancer in a subject comprising:
administering to the subject an effective amount of the compound as claimed in claim 1.

12. The method for treatment as claimed in claim 11, wherein cancer is a disorder or condition selected from melanoma, triple negative breast cancer, colon cancer, colorectal cancer, lung cancer, prostate cancer, renal cell cancer, non-small cell lung cancer, bladder cancer, cervical, vulvar or anal cancer, esophageal cancer, metastatic head and neck cancer, liver cancer, lymphoma, multiple myeloma, ovarian cancer, pancreatic cancer, acute myeloid leukemia, or Kaposi sarcoma.

* * * * *